US009757437B2

(12) United States Patent
Blair et al.

(10) Patent No.: US 9,757,437 B2
(45) Date of Patent: *Sep. 12, 2017

(54) KALLIKREIN INHIBITORS AND ANTI-THROMBOLYTIC AGENTS AND USES THEREOF

(71) Applicant: DYAX CORP., Cambridge, MA (US)

(72) Inventors: Henry Blair, Boston, MA (US); Thomas Beck, Concord, MA (US); Robert Charles Ladner, Ijamsville, MD (US)

(73) Assignee: Dyax Corp., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/271,105

(22) Filed: May 6, 2014

(65) Prior Publication Data

US 2014/0288001 A1 Sep. 25, 2014

Related U.S. Application Data

(60) Division of application No. 13/458,086, filed on Apr. 27, 2012, now Pat. No. 8,716,225, which is a continuation of application No. 11/804,388, filed on May 18, 2007, now Pat. No. 8,188,045, which is a division of application No. 11/125,639, filed on May 9, 2005, now Pat. No. 7,235,530, which is a continuation-in-part of application No. 10/953,902, filed on Sep. 27, 2004, now Pat. No. 7,153,829.

(51) Int. Cl.
*A61K 38/55* (2006.01)
*A61K 38/57* (2006.01)
*A61K 31/195* (2006.01)
*A61K 45/06* (2006.01)

(52) U.S. Cl.
CPC ............ *A61K 38/55* (2013.01); *A61K 31/195* (2013.01); *A61K 38/57* (2013.01); *A61K 45/06* (2013.01)

(58) Field of Classification Search
None
See application file for complete search history.

(56) References Cited

U.S. PATENT DOCUMENTS

| | | |
|---|---|---|
| 3,682,776 A | 8/1972 | Grundmann et al. |
| 3,691,016 A | 9/1972 | Patel |
| 3,969,287 A | 7/1976 | Jaworek et al. |
| 4,118,481 A | 10/1978 | Schnabel et al. |
| 4,153,687 A | 5/1979 | Schnabel et al. |
| 4,179,337 A | 12/1979 | Davis et al. |
| 4,195,128 A | 3/1980 | Hildebrand et al. |
| 4,229,537 A | 10/1980 | Hodgins |
| 4,247,642 A | 1/1981 | Hirohara et al. |
| 4,330,440 A | 5/1982 | Ayers et al. |
| 4,377,572 A | 3/1983 | Schwarz et al. |
| 4,399,216 A | 8/1983 | Axel et al. |
| 4,447,224 A | 5/1984 | DeCant |
| 4,447,233 A | 5/1984 | Mayfield |
| 4,595,674 A | 6/1986 | Tschesche et al. |
| 4,609,725 A | 9/1986 | Brady et al. |
| 4,634,665 A | 1/1987 | Axel et al. |
| 4,657,893 A | 4/1987 | Krantz et al. |
| 4,845,242 A | 7/1989 | Powers et al. |
| 4,881,175 A | 11/1989 | Ladner |
| 4,931,385 A | 6/1990 | Block et al. |
| 4,946,778 A | 8/1990 | Ladner et al. |
| 4,966,852 A | 10/1990 | Wun et al. |
| 5,106,833 A | 4/1992 | Broze et al. |
| 5,118,668 A | 6/1992 | Auerswald et al. |
| 5,166,133 A | 11/1992 | Houston et al. |
| 5,179,017 A | 1/1993 | Axel et al. |
| 5,212,091 A | 5/1993 | Diaz-Collier et al. |
| 5,223,409 A | 6/1993 | Ladner et al. |
| 5,260,203 A | 11/1993 | Ladner et al. |
| 5,278,144 A | 1/1994 | Wolf |
| 5,278,285 A | 1/1994 | Ebbers et al. |
| 5,312,736 A | 5/1994 | Rasmussen et al. |
| 5,372,933 A | 12/1994 | Zamarron et al. |
| 5,373,090 A | 12/1994 | Norris et al. |
| 5,378,614 A | 1/1995 | Petersen et al. |
| 5,407,915 A | 4/1995 | Fritz et al. |
| 5,409,895 A | 4/1995 | Morishita et al. |
| 5,426,224 A | 6/1995 | Lee et al. |
| 5,441,931 A | 8/1995 | Sprecher et al. |
| 5,444,156 A | 8/1995 | Veloso et al. |
| 5,446,090 A | 8/1995 | Harris |
| 5,455,338 A | 10/1995 | Sprecher et al. |
| 5,466,783 A | 11/1995 | Wun et al. |
| 5,563,123 A | 10/1996 | Innis et al. |
| 5,576,294 A | 11/1996 | Norris et al. |
| 5,583,107 A | 12/1996 | Wolf et al. |

(Continued)

FOREIGN PATENT DOCUMENTS

| | | |
|---|---|---|
| AT | E275583 T1 | 4/2005 |
| CA | 2180950 A1 | 3/2005 |

(Continued)

OTHER PUBLICATIONS

U.S. Appl. No. 10/016,329, filed Oct. 26, 2001, Markland, William.
U.S. Appl. No. 11/860,853, filed Sep. 25, 2007, Ladner et al.
U.S. Appl. No. 11/930,700, filed Oct. 31, 2007, Ladner et al.
U.S. Appl. No. 11/931,695, filed Oct. 31, 2007, Ladner, Robert C.
U.S. Appl. No. 12/471,875, filed May 26, 2009, Ley et al.
U.S. Appl. No. 13/571,138, filed Aug. 9, 2012, Markland et al.
A.F. Williams; A.N. Barclay, Ann. Rev Immunol., 1988, vol. 6, pp. 381-405.
Abuchowski et al., "Alteration of immunological properties of bovine serum albumin by covalent attachment of polyethylene glycol," J. Bio. Chem., 1977, vol. 252, pp. 3578-3581.

(Continued)

*Primary Examiner* — Marsha Tsay
(74) *Attorney, Agent, or Firm* — Wolf, Greenfield & Sacks, P.C.

(57) ABSTRACT

Methods, kits and compositions are described that include a non-naturally occurring kallikrein inhibitor and an anti-thrombolytic agent, e.g., an anti-fibrinolytic agent, for preventing or reducing blood loss and/or ischemia, e.g., ischemia associated with perioperative blood loss and cerebral ischemia, the onset of systemic inflammatory response, and/or reperfusion injury, e.g., reperfusion injury associated with cerebral ischemia or a focal brain ischemia, e.g., in patients subjected to invasive surgical procedures, especially procedures requiring cardiopulmonary bypass.

12 Claims, 4 Drawing Sheets

(56) References Cited

U.S. PATENT DOCUMENTS

| | | |
|---|---|---|
| 5,585,089 A | 12/1996 | Queen et al. |
| 5,589,359 A | 12/1996 | Innis et al. |
| 5,618,696 A | 4/1997 | Norris et al. |
| 5,629,176 A | 5/1997 | Bjorn et al. |
| 5,635,187 A | 6/1997 | Bathurst et al. |
| 5,648,331 A | 7/1997 | Koudsi et al. |
| 5,663,143 A | 9/1997 | Ley et al. |
| 5,672,662 A | 9/1997 | Harris et al. |
| 5,677,146 A | 10/1997 | Sprecher et al. |
| 5,693,761 A | 12/1997 | Queen et al. |
| 5,693,762 A | 12/1997 | Queen et al. |
| 5,695,760 A | 12/1997 | Faanes et al. |
| 5,696,088 A | 12/1997 | Innis et al. |
| 5,719,041 A | 2/1998 | Lazarus et al. |
| 5,736,364 A | 4/1998 | Kelley et al. |
| 5,739,208 A | 4/1998 | Harris |
| 5,747,449 A | 5/1998 | Lasters et al. |
| 5,770,568 A | 6/1998 | Auerswald et al. |
| 5,780,265 A | 7/1998 | Dennis et al. |
| 5,786,328 A | 7/1998 | Dennis et al. |
| 5,795,865 A | 8/1998 | Markland et al. |
| 5,795,954 A | 8/1998 | Lazarus et al. |
| 5,800,385 A | 9/1998 | Demopulos et al. |
| 5,804,376 A | 9/1998 | Braxton et al. |
| 5,824,870 A | 10/1998 | Baszczynski et al. |
| 5,834,244 A | 11/1998 | Dennis et al. |
| 5,843,895 A | 12/1998 | Lazarus et al. |
| 5,849,992 A | 12/1998 | Meade et al. |
| 5,853,723 A | 12/1998 | Jacobs et al. |
| 5,863,893 A | 1/1999 | Dennis et al. |
| 5,869,637 A | 2/1999 | Au-Young et al. |
| 5,874,407 A | 2/1999 | Kelley et al. |
| 5,880,256 A | 3/1999 | Dennis et al. |
| 5,900,461 A | 5/1999 | Harris |
| 5,914,316 A | 6/1999 | Brown et al. |
| 5,932,462 A | 8/1999 | Harris et al. |
| 5,951,974 A | 9/1999 | Gilbert et al. |
| 5,962,266 A | 10/1999 | White et al. |
| 5,990,237 A | 11/1999 | Bentley et al. |
| 5,994,125 A | 11/1999 | Markland et al. |
| 6,001,596 A | 12/1999 | Hillman et al. |
| 6,004,579 A | 12/1999 | Bathurst et al. |
| 6,008,196 A | 12/1999 | Curran et al. |
| 6,010,880 A | 1/2000 | Markland et al. |
| 6,013,448 A | 1/2000 | Braxton et al. |
| 6,013,763 A | 1/2000 | Braisted et al. |
| 6,017,723 A | 1/2000 | Rao et al. |
| 6,057,287 A | 5/2000 | Markland et al. |
| 6,063,764 A | 5/2000 | Creasey et al. |
| 6,071,723 A | 6/2000 | Markland et al. |
| 6,087,473 A | 7/2000 | Conklin et al. |
| 6,090,916 A | 7/2000 | Vlasuk et al. |
| 6,103,499 A | 8/2000 | Markland et al. |
| 6,103,500 A | 8/2000 | Innis et al. |
| 6,113,896 A | 9/2000 | Lazarus et al. |
| 6,126,933 A | 10/2000 | Warne et al. |
| 6,159,938 A | 12/2000 | Gyorkos et al. |
| 6,171,587 B1 | 1/2001 | Wun et al. |
| 6,174,721 B1 | 1/2001 | Innis et al. |
| 6,180,607 B1 | 1/2001 | Davies et al. |
| 6,214,966 B1 | 4/2001 | Harris |
| 6,242,414 B1 | 6/2001 | Johnson et al. |
| 6,258,351 B1 | 7/2001 | Harris |
| 6,261,279 B1 | 7/2001 | Demopulos et al. |
| 6,306,884 B1 | 10/2001 | Buckman et al. |
| 6,333,402 B1 | 12/2001 | Markland et al. |
| 6,348,558 B1 | 2/2002 | Harris et al. |
| 6,362,254 B2 | 3/2002 | Harris et al. |
| 6,362,276 B1 | 3/2002 | Harris et al. |
| 6,376,604 B2 | 4/2002 | Kozlowski |
| 6,407,213 B1 | 6/2002 | Carter et al. |
| 6,413,507 B1 | 7/2002 | Bentley et al. |
| 6,423,498 B1 | 7/2002 | Markland et al. |
| 6,432,397 B1 | 8/2002 | Harris |
| 6,455,639 B1 | 9/2002 | Yasukohchi et al. |
| 6,472,195 B2 | 10/2002 | Hillman et al. |
| 6,515,100 B2 | 2/2003 | Harris |
| 6,534,276 B1 | 3/2003 | Wun et al. |
| 6,548,262 B2 | 4/2003 | Gentz et al. |
| 6,576,235 B1 | 6/2003 | Williams et al. |
| 6,583,108 B1 | 6/2003 | Tamburini et al. |
| 6,610,281 B2 | 8/2003 | Harris |
| 6,624,246 B2 | 9/2003 | Kozlowski |
| 6,664,331 B2 | 12/2003 | Harris et al. |
| 6,689,582 B1 | 2/2004 | Davies et al. |
| 6,710,125 B2 | 3/2004 | Kozlowski |
| 6,774,180 B2 | 8/2004 | Kozlowski et al. |
| 6,783,960 B2 | 8/2004 | Innis et al. |
| 6,783,965 B1 | 8/2004 | Sherman et al. |
| 6,806,360 B2 | 10/2004 | Wun et al. |
| 6,814,982 B2 | 11/2004 | Poncin et al. |
| 6,914,135 B2 | 7/2005 | Sheppard et al. |
| 6,953,674 B2 | 10/2005 | Markland et al. |
| 6,989,369 B2 | 1/2006 | Ladner et al. |
| 7,064,107 B2 | 6/2006 | Ladner et al. |
| 7,067,144 B2 | 6/2006 | Demopulos et al. |
| 7,078,383 B2 | 7/2006 | Ley et al. |
| 7,153,829 B2 | 12/2006 | Ladner et al. |
| 7,166,576 B2 | 1/2007 | Cicardi et al. |
| 7,235,530 B2 | 6/2007 | Blair et al. |
| 7,276,480 B1 | 10/2007 | Ladner et al. |
| 7,550,427 B2 | 6/2009 | Ley et al. |
| 7,628,983 B2 | 12/2009 | Markland et al. |
| 7,704,949 B2 | 4/2010 | Ladner et al. |
| 7,718,617 B2 | 5/2010 | Cicardi et al. |
| 7,811,991 B2 | 10/2010 | Ladner et al. |
| 7,851,442 B2 | 12/2010 | Ladner et al. |
| 7,919,462 B2 | 4/2011 | Markland et al. |
| 8,034,775 B2 | 10/2011 | Ladner et al. |
| 8,124,586 B2 | 2/2012 | Ladner et al. |
| 8,188,045 B2 | 5/2012 | Blair et al. |
| 8,283,321 B2 | 10/2012 | Markland et al. |
| 8,710,007 B2 | 4/2014 | Ladner et al. |
| 8,716,225 B2 | 5/2014 | Blair et al. |
| 8,828,703 B2 | 9/2014 | Ladner |
| 9,107,928 B2 | 8/2015 | Belichard |
| 9,114,144 B2 | 8/2015 | Ladner et al. |
| 9,480,733 B2 | 11/2016 | Ladner et al. |
| 2001/0027180 A1 | 10/2001 | Isaacs |
| 2002/0102703 A1 | 8/2002 | Sheppard et al. |
| 2002/0111460 A1 | 8/2002 | Holloway |
| 2003/0012969 A1 | 1/2003 | Clark |
| 2003/0096733 A1 | 5/2003 | Ny et al. |
| 2003/0100070 A1 | 5/2003 | Holloway |
| 2003/0113726 A1 | 6/2003 | Tsuchihashi et al. |
| 2003/0114372 A1 | 6/2003 | White et al. |
| 2003/0153046 A1 | 8/2003 | Jensen et al. |
| 2003/0175919 A1 | 9/2003 | Ley et al. |
| 2003/0223977 A1 | 12/2003 | Ley et al. |
| 2004/0038893 A1 | 2/2004 | Ladner et al. |
| 2004/0044075 A1 | 3/2004 | Staveski et al. |
| 2004/0049018 A1 | 3/2004 | Bailon et al. |
| 2004/0053206 A1 | 3/2004 | Cicardi et al. |
| 2004/0062746 A1 | 4/2004 | Martinez et al. |
| 2004/0062748 A1 | 4/2004 | Martinez et al. |
| 2004/0106747 A1 | 6/2004 | Bailon et al. |
| 2004/0126361 A1 | 7/2004 | Saifer et al. |
| 2004/0152633 A1 | 8/2004 | Jorgensen et al. |
| 2004/0171794 A1 | 9/2004 | Ladner et al. |
| 2004/0180827 A1 | 9/2004 | Chen et al. |
| 2004/0209243 A1 | 10/2004 | Nixon et al. |
| 2005/0004021 A1 | 1/2005 | Sprecher et al. |
| 2005/0075665 A1 | 4/2005 | Brenzel et al. |
| 2005/0089515 A1 | 4/2005 | Ley et al. |
| 2005/0164928 A1 | 7/2005 | Ladner et al. |
| 2005/0164945 A1 | 7/2005 | Nixon et al. |
| 2005/0180977 A1 | 8/2005 | Nixon et al. |
| 2006/0069020 A1 | 3/2006 | Blair et al. |
| 2006/0194727 A1 | 8/2006 | Ladner et al. |
| 2006/0205671 A1 | 9/2006 | Vinten-Johansen |
| 2006/0228331 A1 | 10/2006 | Peschke et al. |
| 2006/0264603 A1 | 11/2006 | Markland et al. |
| 2007/0020252 A1 | 1/2007 | Ladner et al. |
| 2007/0041959 A1 | 2/2007 | Ley et al. |

(56) References Cited

U.S. PATENT DOCUMENTS

| | | |
|---|---|---|
| 2007/0049522 A1 | 3/2007 | Ladner et al. |
| 2007/0065407 A1 | 3/2007 | Patten et al. |
| 2007/0079096 A1 | 4/2007 | Chen |
| 2007/0100133 A1 | 5/2007 | Beals et al. |
| 2007/0117752 A1 | 5/2007 | Larsen et al. |
| 2007/0213275 A1 | 9/2007 | Clark et al. |
| 2007/0249807 A1 | 10/2007 | Ladner et al. |
| 2007/0253949 A1 | 11/2007 | Golz et al. |
| 2007/0270344 A1 | 11/2007 | Belichard |
| 2008/0031426 A1 | 2/2008 | Weeks |
| 2008/0038276 A1 | 2/2008 | Sinha et al. |
| 2008/0050716 A1 | 2/2008 | Cicardi et al. |
| 2008/0064637 A1 | 3/2008 | Ladner et al. |
| 2008/0076712 A1 | 3/2008 | Ladner et al. |
| 2008/0131426 A1 | 6/2008 | Ladner et al. |
| 2008/0139473 A1 | 6/2008 | Ladner et al. |
| 2008/0152656 A1 | 6/2008 | Ladner et al. |
| 2008/0182283 A1 | 7/2008 | Markland et al. |
| 2008/0188409 A1 | 8/2008 | Blair et al. |
| 2008/0200646 A1 | 8/2008 | Ladner et al. |
| 2008/0221031 A1 | 9/2008 | Blair et al. |
| 2008/0226655 A1 | 9/2008 | Ladner et al. |
| 2008/0255025 A1 | 10/2008 | Ladner |
| 2008/0260752 A1 | 10/2008 | Ladner et al. |
| 2008/0299050 A1 | 12/2008 | Bortz et al. |
| 2009/0023651 A1 | 1/2009 | Markland et al. |
| 2009/0062195 A1 | 3/2009 | Ladner et al. |
| 2009/0075887 A1 | 3/2009 | McPherson |
| 2009/0082267 A1 | 3/2009 | Ladner et al. |
| 2009/0105142 A1 | 4/2009 | Moscicki |
| 2009/0117130 A1 | 5/2009 | Ladner et al. |
| 2009/0123475 A9 | 5/2009 | Siegel |
| 2009/0215119 A1 | 8/2009 | Ladner |
| 2009/0221480 A1 | 9/2009 | Blair et al. |
| 2009/0227494 A1 | 9/2009 | Blair et al. |
| 2009/0227495 A1 | 9/2009 | Blair et al. |
| 2009/0233852 A1 | 9/2009 | Blair et al. |
| 2009/0234009 A1 | 9/2009 | Blair et al. |
| 2009/0247452 A1 | 10/2009 | Ellis et al. |
| 2009/0247453 A1 | 10/2009 | Blair et al. |
| 2009/0264350 A1 | 10/2009 | Blair et al. |
| 2010/0034805 A1 | 2/2010 | Ladner et al. |
| 2010/0183625 A1 | 7/2010 | Sternlicht |
| 2010/0273721 A1 | 10/2010 | Belichard |
| 2010/0286061 A1 | 11/2010 | Devy et al. |
| 2011/0008762 A1 | 1/2011 | Cicardi et al. |
| 2011/0086801 A1 | 4/2011 | Ladner et al. |
| 2011/0136746 A1 | 6/2011 | Markland et al. |
| 2011/0172140 A1 | 7/2011 | Ley et al. |
| 2011/0200611 A1 | 8/2011 | Sexton |
| 2012/0015881 A1 | 1/2012 | Ladner et al. |
| 2012/0201756 A1 | 8/2012 | Sexton |
| 2012/0322744 A1 | 12/2012 | Ley et al. |
| 2012/0328517 A1 | 12/2012 | Markland et al. |
| 2013/0012438 A1 | 1/2013 | Blair et al. |
| 2014/0349940 A1 | 11/2014 | Ladner et al. |
| 2015/0368359 A1 | 12/2015 | Belichard |

FOREIGN PATENT DOCUMENTS

| | | |
|---|---|---|
| DE | 695 33 472 T2 | 1/2006 |
| EP | 0 132 732 A2 | 2/1985 |
| EP | 0 255 011 A2 | 2/1988 |
| EP | 0 274 826 A1 | 7/1988 |
| EP | 0 285 123 A2 | 10/1988 |
| EP | 0 301 122 A1 | 2/1989 |
| EP | 0 307 592 A2 | 3/1989 |
| EP | 0 318 451 A2 | 5/1989 |
| EP | 0 401 508 A2 | 12/1990 |
| EP | 0 486 001 A1 | 5/1992 |
| EP | 0 401 508 B1 | 11/1994 |
| EP | 0 621 870 B1 | 5/1997 |
| EP | 0 621 871 B1 | 7/1997 |
| EP | 0 739 355 B1 | 9/2004 |
| EP | 1 484 339 A2 | 12/2004 |
| JP | 07-504891 T | 6/1995 |
| JP | 09-059838 A | 3/1997 |
| JP | 09-509048 | 9/1997 |
| JP | 09-511131 T | 11/1997 |
| JP | 10-503375 A | 3/1998 |
| JP | 10-510996 | 10/1998 |
| JP | 2002-524076 A | 8/2002 |
| JP | 2002-543147 | 12/2002 |
| WO | WO-89/10374 A1 | 11/1989 |
| WO | WO-90/02809 A1 | 3/1990 |
| WO | WO-92/06111 A1 | 4/1992 |
| WO | WO-93/09233 A2 | 5/1993 |
| WO | WO-93/14120 A1 | 7/1993 |
| WO | WO-93/14121 A1 | 7/1993 |
| WO | WO-93/14122 A1 | 7/1993 |
| WO | WO-95/18830 A2 | 7/1995 |
| WO | WO-95/21601 A2 | 8/1995 |
| WO | WO-95/23860 A3 | 9/1995 |
| WO | WO-96/04377 A1 | 2/1996 |
| WO | WO-96/04378 A3 | 2/1996 |
| WO | WO-96/20278 A2 | 7/1996 |
| WO | WO-96/35788 A2 | 11/1996 |
| WO | WO-97/33996 A2 | 9/1997 |
| WO | WO-98/52976 A1 | 11/1998 |
| WO | WO 99/21558 | 5/1999 |
| WO | WO-99/63090 A2 | 12/1999 |
| WO | WO-00/14235 A1 | 3/2000 |
| WO | WO-00/34317 A2 | 6/2000 |
| WO | WO-01/09968 A1 | 2/2001 |
| WO | WO-01/14424 A2 | 3/2001 |
| WO | WO-01/68707 A1 | 9/2001 |
| WO | WO-01/79480 A1 | 10/2001 |
| WO | WO-02/06334 A1 | 1/2002 |
| WO | WO-02/06539 A1 | 1/2002 |
| WO | WO 02/20569 | 3/2002 |
| WO | WO 02/30393 | 4/2002 |
| WO | WO-02/092147 A2 | 11/2002 |
| WO | WO-02/094200 A2 | 11/2002 |
| WO | WO-03/006860 A1 | 1/2003 |
| WO | WO-03/066824 A2 | 8/2003 |
| WO | WO-03/103475 A2 | 12/2003 |
| WO | WO-2004/019968 A1 | 3/2004 |
| WO | WO-2004/062646 A1 | 7/2004 |
| WO | WO-2004/062657 A | 7/2004 |
| WO | WO-2004/062689 A1 | 7/2004 |
| WO | WO-2005/021556 A2 | 3/2005 |
| WO | WO-2005/021557 A2 | 3/2005 |
| WO | WO-2005/075665 A2 | 8/2005 |
| WO | WO-2006/017538 A2 | 2/2006 |
| WO | WO-2006/036860 A2 | 4/2006 |
| WO | WO-2006/066878 A1 | 6/2006 |
| WO | WO-2006/089005 A2 | 8/2006 |
| WO | WO-2007/079096 A2 | 7/2007 |
| WO | WO-2007/106746 A2 | 9/2007 |
| WO | WO-2008/000833 A1 | 1/2008 |
| WO | WO-2009/026334 A2 | 2/2009 |
| WO | WO-2009/026539 A1 | 2/2009 |
| WO | WO-2009/102927 A1 | 8/2009 |
| WO | WO-2010/003475 A2 | 1/2010 |
| WO | WO-2010/006746 | 1/2010 |
| WO | WO-2011/085103 A2 | 7/2011 |
| WO | WO-2012/094587 A1 | 7/2012 |

OTHER PUBLICATIONS

Abuchowski et al., "Cancer therapy with chemically modified enzymes, I., Antitumor properties of polyethylene glycol-asparaginase conjugates," Cancer Biochem. Biophys., 1984, vol. 7, pp. 175-186.

Abuchowski et al., "Effect of covalent attachment of polyethylene glycol on immunogenicity and circulating life of bovine," J. Biol. Chem., 1977, vol. 252, pp. 3582-3586.

Adams et al: "The role of viscosupplementation with hylan G-F 20 (Synvisc(R)) in the treatment of osteoarthritis of the knee: a Canadian multicenter trial comparing hylan G-F 20 alone, hylan G-F 20 with non-steroidal anti-inflammatory drugs (NSAIDs) and NSAIDs alone", Osteoarthritis and Cartilage, Bailliere Tindall, London, GB, vol. 3, No. 4, pp. 213-225, (Dec. 1, 1995).

(56) References Cited

OTHER PUBLICATIONS

Adelman, et al., Proteolysis of Platelet Glycoprotein lb by Plasmin Is Facilitated by Plasmin Lysine-Binding Regions. Blood, vol. 68 (6): 1280-1284, (Dec. 1986).

Albrecht, et al., Elastase Inhibition by the Inter-a-Trypsin Inhibitor and Derived Inhibitors of Man and Cattle, Hoppe-Seyler's Z. Physiol. Chem., vol. 364: 1703-1708, (Dec. 1983).

Albrecht, et al., Kunitz-Type Proteinase Inhibitors Derived by Limited Proteolysis of the Inter-a-Trypsin Inhibitors From several Mammalian Sera, Hoppe-Seyler's Z. Physiol. Chem., vol. 364: 1697-1702, (Dec. 1983).

Altschul et al., "Gapped BLAST and PSI-BLAST: a new generation of protein database search programs," Nucleic Acids Research, 1997, vol. 25, pp. 3389-3402, Oxford University Press.

Anba, et al., Improving the Stability of a Foreign Protein in the Periplasmic Space of *Escherichia coli*, Biochimie, vol. 70(6): 727-733, (1988).

Angliker, et al., The Synthesis of Lysylflouromethanes and their Properties as Inhibitors of Trypsin, Plasmin and Cathepsin B, Biochemistry, 241:871-875, (1987).

Asano M. et al., "Effects of a nonpeptide bradykinin B2 receptor antagonist, FR167344, on different in vivo animal models of inflammation", Br J Pharmacol, vol. 122, p. 1436-1440 (1997).

Asano M. et al., Br J Pharmacol, vol. 122, p. 1436-1440 (1997).

Atherton, et al., Peptide Synthesis. Part 2. Procedures for Solid Phase Synthesis using Na-Fluorenylmethycarbonylamino-acids on Polyamide Supports. Synthesis of Substance P and of Acyl Carrier Protein 65-74 Decapeptide, J. Chem. Soc. Perkins Trans, 1:538-546, (1981).

Attwood, The Babel of Bioinformatics; Science, vol. 290, pp. 471-473 (2000).

Auerswald et al., Expression, Isolation and Characterization of Recombinant [Arg15, Glu52] Aprotinin, Bio. Chem. Hoppe-Seyler, 369:(Suppl)27-35 (1988).

Baba, M et al., States of Tyrosyl Residues and Circular Dichroism of Kunitz Trypsin Inhibitor, J. Biochem 65 (1):113-121 (1969).

Balduyck, et al., Human Urinary Proteinase Inhibitor: Inhibitory Properties and Interaction with Bovine Trypsin, Bio. Chem. Hoppe-Seyler, vol. 366: 9-14, (1985).

Baneyx et al., Construction and Characterization of *Escherichia coli* Strains Deficient in Multiple Secreted Proteases: Protease III Degrades High-Molecular-Weight Substrates In Vivo, J Bacteriol., 173:2696-2703 (1991).

Baneyx et al., "In Vivo Degradation of Secreted Fusion Proteins by the *Escherichia coli* Outer Membrane Protease OmpT", J. Bacteriol., 172:491-494, (1990).

Basu et al., "Structure-function engineering of interferon-b-1 b for improving stability, solubility, potency, immunogenicity, and pharmacokinetic properties by site-selective mono-PEGylation," Bioconjugate Chemistry, 2006, vol. 17, pp. 618-630.

Bayes et al., "Gateways to Clinical Trials" Methods Find Exp. Clin. Pharmacol., vol. 28(3): pp. 185-206 (2006).

Beckmann et al., "Preparation of chemically 'mutated' aprotinin homologues by semisynthesis-P1 substitutions change inhibitory specificity," Eur. J. Biochem., vol. 176, pp. 675-682 (1988).

Berge, S.M., et al., "Pharmaceutical salts", J. Pharm. Sci. 66:1-19 (1977).

Bergthorsdotiir et al., "Signals that initiate somatic hypermutation of B cell in vitro", J. Immunol., p. 166:2228 (2001).

Berndt, et al., "Designed Replacement of an Internal Hydration Water Molecule in BPTI: Structural and Functional Implications of a Glycine-to-Serine Mutation," Biochemistry, 32: 4564-4570 (1993).

Bhoola et al., "Bioregulation of Kinins: Kallikreins, Kininogens and Kininases," Pharmacological Reviews, 44 :1-80 (1992).

Blaber et al., "Targeting kallikrein 6-proteolysis attenuates CNS inflammatory disease," The FASEB Journal, express article published online Mar. 19, 2004.

Blijlevens et al: "Palifermin (recombinant keratinocyte growth factor-1 ): a pleiotropic growth factor with multiple biological activities in preventing chemotherapy- and radiotherapy-induced mucositis", Annals of Oncology, vol. 18, No. 5, Jan. 1, 2007 (Jan. 1, 2007 ), pp. 817-826.

Bork, "Powers and pitfalls in sequence analysis: the 70% hurdle," Genome Research, vol. 10, pp. 398-400 (2000).

Borregaard et al., "Granules of the human neutrophilic polymorphonuclear leukocyte," Blood, 1997, vol. 89, No. 10, pp. 3503-3521.

Bowdish K, et. al., "Yeast expression of a catalytic antibody with chorismate mutase activity.", J Biol Chem.; 266 (18):11901-8 (Jun. 25 1991).

Branden et al., "Prediction, Engineering, and Design of Protein," Introduction to Protein Structure, 1991, pp. 247, Garland Publishing Inc., New York.

Brenner, "Errors in genome annotation," Trends in Genetics, vol. 15, No. 4, pp. 132-133 (1999).

Brinkmann et al., "Design of an aprotinin variant with inhibitory activity against chymotrypsin and cathepsin G by recombinant DNA technology," Biol. Chem. Hoppe-Seyler, vol. 371, pp. 43-52 (1990).

Browne et al., "Expression of Recombinant Human Plasminogen and Aglycoplasminogen in HeLa Cells," GeneBank, Accession No. M74220 (1991).

Broze et al., "Regulation of Coagulation by a Multivalent Kunitz-Type Inhibitor," Biochemistry, 29:7539-7546, (1990).

Brus et al., "Disease Severity Is Correlated with Plasma Clotting and Fibrinolytic and Kinin-Kallikrein Activity in Neonatal Respiratory Distress Syndrome," Pediatric Research, 41 :120-127, (1997).

Buchan et al., "A new model of temporary focal neocortical ischemia in the rat", Stroke 23 (2): 273-9 (1992).

Budavari, ed., Merck index, 11th ed., ISBN 911910-28-X, entries 923, 1745, 2740, 7425, (1989).

Burrage et al., "Matrix metalloproteinases: role in arthritis," Frontiers in Bioscience, 2006, vol. 11, pp. 529-543.

Cantor, J.O., et al., "Elastin and Elastases in Lung Disease", Elastin and Elastases, Chapter 16, vol. 11, pp. 159-168 (1989).

Carey et al., Advanced Organic Chemistry, 3rd Edition, Part B: Reactions and Synthesis, Plenum Press, New York: 678-686 (1990).

Carlson et al., "The Determination of Recombinant Human Tissue-Type Plasminogen Activator Activity by Turbidimetry Using a Microcentrigual Analyzer," Anal. Biochem., 1988, vol. 168, pp. 428-435.

Carmichael, "Rodent models of focal stroke: size, mechanism, and purpose", NeuroRx 2: 396-409 (2005).

Carpenter et al., "Rational design of stable lyophilized protein formulations: theory and practice," Pharmaceutical Biotechnology, vol. 13, pp. 109-133 (2002).

Casati et al., "Cardiopulmonary support and physiology—tranexamic acid compared with high-dose aprotinin in primary elective heart operations: effects on perioperative bleeding and allogeneic transfusions," The Journal of Thoracic and Cardiovascular Surgery, vol. 120, pp. 520-527 (2000).

Cassim et al., "Kallikrein cascade and cytokines in inflamed joints," Pharmacology and Therapeutics, 2002, vol. 94, pp. 1-34.

Cernak, "Animal models of head trauma", NeuroRx. 2(3): 410-422 (2005).

Chen et al., "A model of focal ischemic stroke in the rat: reproducible extensive cortical infarction", Stroke 17 (4): 738-43 (1986).

Chen et al., "Establishment of an animal model of oral mucositis induced by conditioning regimen of hematopoietic stem cell transplantation" Zhonghua Kou Qiang Yi Xue Za Zhi. 42(11 ):672-6 (2007). (Abstract only).

Chen et al., Solution Structure of a Kunitz-type Chymotrypsin Inhibitor Isolated from the Elapid Snake Bungarus Fasciatus, J. Biological Chemistry 276:45079-45087 (2001).

Chen, et al. "Refined 2-5 A X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol. vol. 164, pp. 283-311 (1983).

(56) References Cited

OTHER PUBLICATIONS

Chothia, Cyrus et al., "Canoical Structures for the Hypervariable Regions of Immunoglobins" J. Mol. Biol., (1987), vol. 196, pp. 901-917.
Chung et al., "Human plasma prekallikrein, a zumogen to a serine protease that contains four tandem repeats," GenBank, Accession #P03952 (1986).
Churg et al., "Proteases and emphysema," Curr. Opin. Pulm. Med., 2005, vol. 11, pp. 153-159.
Colman et al., "Activation of the Kallikrein-Kinin System in Arthritis and Enterocolitis in Genetically Susceptible Rats: Modulation by a Selective Plasma Kallikrein Inhibitor," Proc. Assoc. Am. Physicians, 109:10-22 ( 1997).
Colman et al., Hemostasis and Thrombosis Basic Principles and Clinical Practice, Chapter 1, 2nd Edition, 3-17 (1987).
Colman et al., "The Plasma Kallikrein-Kinin System in Sepsis, Inflammatory Arthritis, and Enterocolitis" Clinical Reviews in Allergy and Immunology, vol. 16, pp. 365-384 (1998).
Colman R. W., "Plasma and tissue Kallikrein in Arthritis and Inflammatory Bowel Disease", Immunopharmacology, Jan. 1, 1999, pp. 103-108, vol. 43, No. 2/03, Elsevier Science Publishers, BV.
Colman, et al., "Contact System: A Vascular Biology Modulator With Anticoagulant, Profibrinolytic, Antiadhesive, and Proinflammatory Attributes" Blood, 90, 3819-3843 (1997).
Communication from the European Patent Office for EP Application No. 10180484.7 dated Dec. 11, 2013, 3 pages.
Communication received in EP Patent Application 03791557.6, dated Nov. 20, 2008.
Communication received in EP Patent No. 1 484 339 (App. No. 04019920.0), dated Sep. 29, 2005.
Corpet et al., "Recent improvements of the ProDom database of protein domain families," Nucl. Acids Res., 1999, vol. 27, pp. 263-267.
Cumming et al., "Hemodynamic, Renal, and Hormonal Aprotinin in an Ovine Model of Septic Shock," Critical Care Medicine, 20:1134-1139 (1992).
Cunningham et al., "Structural and functional characterization of tissue factor pathway inhibitor following degradation by matrix metalloproteinase-8," Biochem. J., 2002, vol. 367, pp. 451-458.
Currie, B. "Design and Synthesis of a Bicyclic Non-Peptide β-Bend Mimetic of Enkephalin," Tetrahedron, 49:3489-3500 (1993).
De Campos, et al., "Antioedematogenic and antinociceptive actions of NPC 18521, a novel bradykinin B2 receptor antagonist", Eur J Pharmacol316, 277-286 (1996).
De Haard, et al. "A large non-immunized human Fab fragment phage library that permits rapid isolation and kinetic analysis of high affinity antibodies". J. Biol. Chem 274:18218-30, (1999).
De Wildt, et al. "Antibody arrays for high-throughput screening of antibody-antigen interactions", Nat. Biotechnol. 18:989-994 (2000).
De Wildt, et al., "Characterization of human variable domain antibody fragments against the U1 RNA-associated a protein, selected from a synthetic and patient-derived combinatorial V gene library" Eur J Immunol. 26(3):629-39 (1996).
Debiopharm Brochure, "Engineered protein inhibitor of human neutrophil elastase EPIO-hNE4 (DX-890)," Dated Oct. 2004, printed from www.debio.com/e/pdf/fiche_epi_hne4_e.pdf.
Dela Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).
Dela Cadena, et al., "Inhibition of Plasma Kallikrein Prevents Peptidoglycan-Induced Arthritis in the Lewis Rat," FASEB Journal, 9:446-452 (1995).
Delacourt et al., "Protection against acute lung injury by intravenous or intratracheal pretreatment with EPI-HNE-4, a new potent neutrophil elastase inhibitor," Am. J. Respir. Cell Mol. Biol., Mar. 26, 2002, vol. 26, No. 3, pp. 290-297.
Delaria et al., "Characterization of placental bikunin, a novel human serine protease inhibitor," J. Biological Chemistry, May 2, 1997, vol. 272, No. 18, pp. 12209-12214.

Delgado et al., "The uses and properties of PEG-linked proteins," Critical Review in Therapeutic Drug Carrier Systems, 1992, vol. 9, No. 3,4, pp. 249-304.
Deng , et. al., "Production of recombinant humanized anti-HBsAg Fab antibody by fermentation" Sheng Wu Gong Cheng Xue Bao, 20(5):800-4 (Sep. 2004) (Abstract Only).
Dennis & Lazarus, "Kunitz Domain Inhibitors of Tissue Factor-Factor VIIa (I. Potent Inhibitors Selected from Libraries by Phage Display)," Journal of Biological Chemistry 269:22129-22136 (1994).
Dennis & Lazarus, "Kunitz Domain Inhibitors of Tissue Factor-Factor VIIa (II. Potent and Specific Inhibitors by Competitive Phage Selection)," Journal of Biological Chemistry, 269:22137-22144 (1994).
Dennis et al., "Potent and Selective Kunitz Domain Inhibitors of Plasma Kallikrein Designed by Phage Display," J. Biol. Chem., 270:25411-25417 (1995).
Devani et al., "Kallikrein-kinin system in inflammatory bowel disease: intestinal involvement and correlation with the degree of tissue inflammation," Digestive and Liver Disease, 2005, vol. 37, pp. 665-673.
Dhalluin et al., "Structural, kinetic, and thermodynamic analysis of the binding of the 40kDa PEG-interferon-α-2a and its individual positional isomers to the extracellular domain of the receptor IFNAR2," Bioconjugate Chemistry, 2005, vol. 16, pp. 518-527.
Diaz et al., "The Design of Water Soluble β-Sheet Structure Based on a Nucleation Strategy," Tetrahedron, 49:3533-3534 (1993).
Dimaio et al., "A New Class of Potent Thrombin Inhibitors That Incorporates a Scissile Pseudopeptide Bond," FEBS Lett., 282(1):47-52 (1991).
Dittmar et al., "External carotid artery territory ischemia impairs outcome in the endovascular filament model of middle cerebral artery occlusion in rats" Stroke 34: 2252-7 (2003).
Dittmar et al.. "Fischer-344 rats are unsuitable for the MCAO filament model due to their cerebrovascular anatomy" J Neurosci Methods 156: 50 (2006).
Doerks, et al., "Protein annotation: detective work for function prediction", Trends in Genetics, vol. 14 (6), pp. 248-250. (1998).
Donnelly et al., "Therapy for chronic obstructive pulmonary disease in the 21st century," Drugs, 2003, vol. 63, pp. 1973-1998.
Dragosits, el. al., "The response to unfolded protein is involved in osmotolerance of Pichia pastoris" BMC Genomics. 2010 Mar 26;11 :207.
Dufton, "Proteinase inhibitors and dendrotoxins," Eur. J. Biochem., vol. 153, pp. 647-654. (1985).
Eigenbrot et al. "Structural Effects Induced by Removal of a Disulfide-Bridge: The X-ray Structure of the C30A/ C51A Mutant of Basic Pancreatic Trypsin Inhibitor at 1.6 A," Protein Engineering, 3:591-598 (1990).
Ellis et al., "The Urokinase Receptor: Involvement in Cell Surface Proteolysis and Cancer Invasion," Ann. NY. Acad. Sci., 667:13-31 (1992).
English Translation of Final Office Action for Japanese Application No. 2004-510605 dated Apr. 28, 2010, 3 pages.
English Translation of Office Action for Japanese Application No. 2010-004265 dated May 1, 2012, 3 pages.
English Translation of Office Action for Japanese Patent Application No. 2004-510605 dated Jul. 10, 2009, 6 pages.
English Translation of Office Action for JP 2011-164650 mailed Oct. 2, 2013, 5 pages.
English Translation of Official Action for Japanese Application No. 2007-533689 dated Apr. 27, 2011, 6 pages.
English Translation of Official Action for Japanese Application No. 2007-533689, mail date Nov. 18, 2011, 8 pages.
English Translation of Official Action for Japanese Application No. 2007-533689, mail date Sep. 18, 2012, 5 pages.
English Translation of Official Action for Japanese Application No. 2011-164650, mail date Mar. 21, 2013, 5 pages.
English Translation of Official Action for Japanese Application No. 2012-242083 dated May 26, 2014, 2 pages.
Enzon Pharmaceuticals, Macromolecular Engineering Technologies, 2004, pp. 1-14.

(56) References Cited

OTHER PUBLICATIONS

European Search Report for EP Application No. 07023364.8, mail date Jun. 6, 2008, 7 pages.
European Search Report for EP Application No. 10180484.7, mail date Mar. 9, 2011, 7 pages.
European Search Report for EP Application No. 10180486.2, mail date Feb. 15, 2011, 6 pages.
Examination Report for Canadian Application No. 2581680 dated Feb. 17, 2012, 5 pages.
Examination Report No. 1 for Australian Patent Application No. 2011201811 dated Feb. 11, 2013, 7 pages.
Examination Report No. 2 on Australian Patent Application No. 2008202377 dated Oct. 4, 2010, 2 pages.
Examination Report No. 2 on Australian Patent Application No. 2011201811 dated Feb. 13, 2013, 3 pages.
Examiner's First Report on Australian Patent Application No. 2003243394 dated Sep. 6, 2006, 2 pages.
Examiner's First Report on Australian Patent Application No. 2005289621 dated Apr. 29, 2010, 2 pages.
Examiner's First Report on Australian Patent Application No. 2008202377 dated Aug. 12, 2009, 2 pages.
Examiner's First Report on Australian Patent Application No. 2011218732 dated Apr. 30, 2012, 1 page.
Examiner's Report for Canadian Application No. 2488558 dated Mar. 7, 2012, 2 pages.
Examiner's Report for Canadian Application No. 2488558 dated Nov. 12, 2010, 3 pages.
Examiner's Report No. 2 on Australian Patent Application No. 2003243394 dated Sep. 26, 2007, 3 pages.
Examiner's Report No. 3 on Australian Patent Application No. 2008202377 dated Jan. 31, 2011, 2 pages.
Extended European Search Report and Search Opinion from European Application No. 10180486.2 dated Feb. 9, 2011.
Extended European Search Report and Search Opinion from European Application No. 10180486.2 dated Feb. 23, 2011.
Extended European Search Report and Search Opinion from European Application No. 10180484.7, mail date Mar. 9, 2011.
Extended European Search Report and Search Opinion from European Application No. 08018863.4, mail date Apr. 1, 2009.
Extended European Search Report and Search Opinion from European Application No. 10164197.5 dated Oct. 1, 2010.
Extended European Search Report and Search Opinion from European Application No. 8798517.2 dated Oct. 26, 2010.
Extended European Search Report for EP Application No. 13174097.9 dated Nov. 15, 2013, 16 pages.
Extended European Search Report from European Application No. 10 72 9465 dated Jan. 18, 2013.
Extended European Search Report from European Application Serial No. 07758271.6 dated Jun. 24, 2010.
Falquet et al., "The Prosite database, its status in 2002," Nucleic Acids Res., 2002, vol. 30, pp. 235-238.
Fidler & Ellis, "The Implications of Angiogenesis for the Biology and Chemistry of Cancer Metastasis," Cell, 79:185-188 (1994).
Fields & Noble, "Solid Phase Peptide Synthesis Utilizing 9-fluorenylmethocarbonyl Amino Acids," Int. J. Peptide Protein Research, 35:161-214 (1990).
Fife, et al, "Cartilage matrix glycoprotein is present in serum in experimental canine osteoarthritis" J Clin Invest. 84(5): 1432-1439 (1989).
Final Office Action for U.S. Appl. No. 11/931,373 dated Jan. 4, 2010, 14 pages.
Final Office Action for U.S. Appl. No. 10/456,986 dated May 18, 2005, 9 pages.
Final Office Action for U.S. Appl. No. 11/804,388 dated Nov. 17, 2011, 9 pages.
Final Office Action for U.S. Appl. No. 11/929,729 dated Aug. 22, 2011, 7 pages.
Final Office Action for U.S. Appl. No. 12/951,543 dated Jul. 18, 2013.
Final Office Action on U.S. Appl. No. 11/930,018 dated Jan. 11, 2010, 12 pages.
Final Office Action on U.S. Appl. No. 13/228,300 dated May 21, 2014, 9 pages.
Final Office Action on U.S. Appl. No. 13/458,086 dated Aug. 7, 2013, 7 pages.
Fraedrich et al., "Reduction of Blood Transfusion Requirement in Open Heart Surgery by Administration of High Doses of Aprotinin-Preliminary Results," Thorac. Cardiovasc. Surg., 37:89-91 (1989).
Freidinger, et al., "Protected Lactam-Bridged Dipeptides for Use as Conformational Constraints in Peptides," Journal of Organic Chemistry, 47:104-109 (1982).
Fries et al., "Inter-a-inhibitor, hyaluronan and inflammation," Acta Biochimica Polonica, 2003, vol. 50, No. 3, pp. 735-742.
Frisbie, "An animal model for venous thrombosis and spontaneous pulmonary embolism." Spinal Cord 43, 635-639 (2005).
G Yetkin et al: "The healing effect of TGF-[alpha] on gastric ulcer induced by acetylsalicylic acid in rats", International Journal of Pharmaceutics, vol. 277, No. 1-2, Jun. 1, 2004 (Jun. 1, 2004), pp. 163-172.
Galeffi, et. al., "Functional expression of a single-chain antibody to ErbB-2 in plants and cell-free systems" J Transl Med. 2006 Sep 29;4:39.
Gardell, et al., "The Search for the Ideal Thrombolytic Agent: Maximize the Benefit and Minimize the Risk," Toxicologic Pathology, 21(2):190-198 (1993).
Gerriets et al., "Complications and pitfalls in rat stroke models for middle cerebral artery occlusion: a comparison between the suture and the macrosphere model using magnetic resonance angiography", Stroke 35: 2372-2377 (2004).
Girard et al., "Functional Significance of the Kunitz-type Inhibitory Domains of Lipoprotein-Associated Coagulation Inhibitor," Nature, 338:518-520 (1989).
Girard et al., "Structure of the Human Lipoprotein-associated Coagulation Inhibitor Gene," J. Biol. Chem., 266:5036-5041 (1991).
Goldenberg et al., "Circular and circularly permuted forms of bovine pancreatic trypsin inhibitor," J. Mol. Biol., vol. 165, pp. 407-413 (1983).
Gonzalez-Quevedo et al., The Synthetic Kunitz Domain Protein DX88 to Treat Angioedema in Patients with Hereditary Angioedema, International Immunopharmacology 2(9):1318 Abstract 205 (2002).
Goodson et al., "Site-directed PEGylation of recombinant interleukin-2 at its glycosylation site," Bio Technology, 1990, vol. 8, pp. 343-346.
Gouzy et al., "Whole genome protein domain analysis using a new method for domain clustering," Computers and Chemistry, 1999, vol. 23, pp. 333-340.
Graham et al., "Animal models of ischemic stroke: balancing experimental aims and animal care", Comp Med 54: 486-496 (2004).
Greilich et al., "Antifibrinolytic therapy during cardiopulmonary bypass reduces proinflammatory cytokine levels: a randomized, double-blind, placebo-controlled study of x-aminocaproic acid and aprotinin," J. Thorac. Cardiovasc. Surg., 2003, vol. 126, pp. 1498-1503.
Gribskov et al., "Profile analysis: Detection of distantly related proteins," Proc. Natl. Acad. Sci. USA, 1987, vol. 84, pp. 4355-4358.
Gribskov et al., "Profile Analysis", Meth. Enzymol., 1990, vol. 183, pp. 146-159.
Grimaldi et al., "Trasylol in the treatment of acute arthritis due to microcrystals," Reumatismo, vol. 23, No. 5, pp. 217-221, (1971) (Abstract only).
Gulberg et al., "Biosynthesis, processing and sorting of neutrophil proteins: insight into neutrophil granule development," Eur. Journal of Hematology, 1997, vol. 58, pp. 137-153.
Guzman et al. "Mono-iodoacetate-induced histologic changes in subchondral bone and articular cartilage of rat femorotibial joints: an animal model of osteoarthritis." Toxicol Pathol. 31(6):619-24 (2003).
Hagihara et al., "Screening for stable mutants with amino acid pairs substituted for the disulfide bond between residues 14 and 38 of

(56) References Cited

OTHER PUBLICATIONS bovine pancreatic trypsin inhibitor (BPTI)," The Journal of Biological Chemistry, 2002, vol. 277, No. 52, pp. 51043-51048.
Han, Eun D. et al., Increased Vascular Permeability in C1 Inhibitor-Deficient Mice Mediated by the Bradykinin Type 2 Receptor, J. Clinical Investigation 109(8):1057-1063 (2002).
Han, Eun D. Reversal of the Increased Vascular Permeability in C1 Inhibitor Deficient Mice: Therapeutic Approaches, International Immunopharmacology 2(9):1315 Abstract 176 (2002).
Hanes et al., "Picomolar affinity antibodies from a fully synthetic naive library selected and evolved by ribosome display" Nat Biotechnol. 18:1287-92 (2000).
Herter et al., "Hepatocyte growth factor is a preferred in vitro substrate for the human hepsin, a membrane-anchored serine protease implicated in prostate and ovarian cancers," Biochem. J., 2005, vol. 390, pp. 125-136.
Hoet, et al., "Generation of high-affinity human antibodies by combining donor-derived and synthetic complementarity-determining-region diversity" Nat Biotechnol. 23(3)344-8 (2005).
Hoogenboom et al. "Natural and designer binding sites made by phage display technology" Immunol Today 2:371-8 (2000).
Hoogenboom et al., "Antibody phage display technology and its applications" Immunotechnology 4:1-20 (1998).
Hoover et al., "Amino Acids of the Recombinant Kringle 1 Domain of Human Plasminogen That Stabilize Its Interaction with ω-Amino Acids," Biochemistry, 32: 10936-10943 (1993).
Hortin, et al., "Allosteric Changes in Thrombin's Activity Produced by peptides Corresponding to Segments of Natural Inhibitors and Substrates," The Journal of Biological Chemistry, 266:6866-6871 (1991).
Horwitz, et. al., "Secretion of functional antibody and Fab fragment from yeast cells.", Proc Natl Acad Sci U S A. 85 (22):8678-82 (Nov. 1988).
Hostomsky, et al., "Solid Phase Assembly of Cow Colostrum Trypsin Inhibitor Gene," Nucleic Acids Research, 15:4849-4856 (1987).
Huang et al., "Kinetics of factor Xa inhibition by tissue factor pathway inhibitor," The Journal of Biological Chemistry, 1993, vol. 268, No. 36, pp. 26950-26955.
Huang et al., "Novel peptide inhibitors of angiotensin-converting enzyme 2," The Journal of Biological Chemistry, 2003, vol. 278, No. 18, pp. 15532-15540.
Huge et al. "A model to investigate postoperative ileus with strain gauge transducers in awake rats" J Surg Res. 74 (2):112-8 (1998). (Abstract Only).
Hwang I K et al: "Copper chaperone for Cu,Zn-SOD supplement potentiates the Cu,Zn-SOD function of neuroprotective effects against ischemic neuronal damage in the gerbil hippocampus", Free Radical Biology and Medicine, Elsevier Science, US, vol. 39, No. 3, Aug. 1, 2005, pp. 392-402.
Hynes et al., "X-ray crystal structure of the protease inhibitor domain of alzheimer's amyloid B-protein precursor," Biochemistry, 1990, vol. 29, pp. 10018-10022.
International Preliminary Examination Report for International Application No. PCT/US2003/017665 dated Mar. 30, 2005, 10 pages.
International Preliminary Report on Patentability for International Application No. PCT/US2005/034335 dated Mar. 3, 2009, 7 pages.
International Preliminary Report on Patentability from International Application No. PCT/US11/20377, mail date Jul. 19, 2012.
International Preliminary Report on Patentability from International Application No. PCT/US2008/073665, mail date Mar. 4, 2010.
International Preliminary Report on Patentability from International Application No. PCT/US2008/074061 dated Mar. 4, 2010.
International Search Report for Application No. PCT/US2003/017665, mail date Jan. 6, 2005, 2 pages.
International Search Report from International Application No. PCT/US05/34335 dated Jul. 21, 2008.
International Search Report from International Application No. PCT/US07/63703 dated Dec. 21, 2007.
International Search Report from International Application No. PCT/US12/20470 dated Apr. 30, 2012.
International Search Report from International Application No. PCT/US2008/074061 dated Dec. 29, 2008.
International Search Report from International Application No. PCT/US2010/020257 dated Jun. 1, 2010.
International Search Report from International Application No. PCT/US03/17802, dated Oct. 30, 2003.
International Search report from International Application No. PCT/US2004/028256 dated Jun. 22, 2005.
International Search Report from International Application No. PCT/US11/20377 dated Jun. 28, 2011.
International Search Report including Written Opinion from International Application No. PCT/08/73665 dated Feb. 5, 2008.
International Search Report of International Application No. PCT/US06/49322 mailed Dec. 7, 2007.
Invitation to Correct Deficiencies for EP Application No. 05799587.0 dated Dec. 17, 2012, 1 page.
Kabat, E.A. et al., "Sequences of Proteins of Immunological Interest", NIH Publication No. 91-3242, (1991).
Kaplan, et. al., "A Prealbumin Activator of Preallirrein. 3. Appearance of Chemotactic Activity for Human Neutrophils by the conversion of Human Prekallikrein", J. Exp. Med. vol. 135(1), p. 81-97; P. 92 Fig 10, p. 93 (1972).
Katre et al., "Chemical modification of recombinant interleukin 2 by polyethylene glycol increases its potency in the murine Meth A sarcoma model," PNAS USA, 1987, vol. 84, pp. 1487-1491.
Katre et al., "Immunogenicity of recombinant IL-2 modified by covalent attachment of polyethylene glycol," J. Immunol., 1990, vol. 144, pp. 209-213.
Kaufman, et al., "Amplification and expression of sequences cotransfected with a modular dihydrofolate reductase complementary dna gene", Mol. Biol. 159:601 621 (1982).
Kelly et al., "Diabetes insipidus in uricase-deficient mice: a model for evaluating therapy with poly(ethylene glycol)-modified," J. Am. Soc. Nephroi., 2001, vol. 12, pp. 1001-1009.
Kemp et al., "Synthesis of Peptide-Functionalized Daicylaminoepinodolidiones," Tetrahedron Letters, 29:5077-5080 (1988).
Kido et al., "Kunitz-type Protease Inhibitor Found in Rat Mast Cells," J. Biol. Chem., 263:18104-18107 (1988).
Kido et al., "Protease Specificity of Kunitz Inhibitor Domain of Alzheimer's Disease Amyloid Protein Precursor," Biochemical and Biophysical Research Communications, 167:716-721 (1990).
Kirchhofer et al., "Hepsin activates pro-hepatocyte growth factor and is inhibited by hepatocyte growth factor activator-1 B (HAI-1B) and HAI-2," FEBS Letters, 2005, vol. 579, pp. 1945-1950.
Kirchhoff, et al., "A Major Human Epididymis-Specific cDNA Encodes a Protein with Sequence Homology to Extracellular Proteinase Inhibitors," Biology of Reproduction, 45:350-357 (1991).
Kline, et al., "Hirulog Peptides with Scissile Bond Replacements Resistant to Thrombin Cleavage," Biochem. Biophys. Res. Comm., 177:1049-1055 (1991).
Knappik et al., "Fully synthetic human combinatorial antibody libraries (HuCAL) based on modular consensus frameworks and CDRs randomized with trinucleotides", J. Mol. Biol. 296:57-86 (2000).
Krogh et al., "Hidden Markov Models in Computational Biology," J. Mol. Biol., 1994, vol. 235, pp. 1501-1531.
Kuno et al., "Possible involvement of neutrophil elastase in impaired mucosal repair in patients with ulcerative colitis," Journal of Gastroenterology, 2002, vol. 37, Supple XIV, pp. 22-32.
Kurjan et al., "Structure of a Yeast Pheromone Gene (MFα): A Putative α-Factor Precursor Contains Four Tandem Copies of Mature α-Factor," Cell, (1982), vol. 30, pp. 933-943.
L. Bergamaschini et al: "Abstracts from the XXth International Complement Workshop: Abstract 16: Neuroprotective effect of plasma kallikrein inhibitor DX-88 on brain ischemia/reperfusion brain injury", Molecular Immunology, vol. 41, No. 2-3, 16, Jun. 2004, pp. 201-333.
Laskowski, et al., "Inhibitors with Class-Specific Reactive Sites," Ann. Rev. Biochem., 49:593-626 (1980).

(56) References Cited

OTHER PUBLICATIONS

Leatherbarrow, et al., "Design of a Small Peptide-Based Proteinase Inhibitor by Modeling the Active -Site Region of Barley Chymotrypsin Inhibitor 2," Biochemistry, 30:10717-10721 (1991).
Leeb-Lundberg et al. "International union of pharmacology. XLV. Classification of the kinin receptor family: from molecular mechanisms to pathophysiological consequences", (2005) Pharmacol Rev 57, 27-77.
Leonetti et al., "Increasing immunogenicity of antigens fused to Ig-binding proteins by cell surface targeting," The Journal of Immunology, 1998, vol. 160, pp. 3820-3827.
Levy Jerrold H et al: "The therapeutic potential of a kallikrein inhibitor for treating hereditary angioedema.", Expert Opinion on Investigational Drugs Sep 2006 LNKD-PUBMED:16916274, vol. 15, No. 9, Sep. 2006 (Sep. 2006), pp. 1077-1090.
Ley et al., "Obtaining a Family of High-Affinity, High Specificity Protein Inhibitors of Plasmin and Plasma Kallikrein," Molecular Diversity, 2:119-124, (1996).
Lilla et al., "Active plasma kallikrein localizes to mast cells and regulates epithelial cell apoptosis, adipocyte differentiation, and stromal remodeling during mammary gland involution" J Biol Chem. 284(20):13792-13803 (2009).
Lohmann, et al., Plasmin- and Plasminogen-Activator Inhibitors after Excimer Laser Photorefractive Keratectomy: New Concept in Prevention of Postoperative Myopic Regression and Haze, Refractive and Corneal Surgery, 9:300-302, (1993).
Longa et al., "Reversible middle cerebral artery occlusion without craniectomy in rats" Stroke 20 (1): 84-91 (1989).
Lucas, et al., "The Binding of Human Plasminogen to Fibrin and Fibrinogen," J. Biol. Chem., 258:4249-4256 (1983).
Lumry et al, Interim Results of EDEMA2, A Multicenter, Open-Label, Repeat-Dosing Study of Intravenous and Subcutaneous Administration of Ecallantide (DX-88) in Hereditary Angioedema. J. Allergy and Clinical Immunology 117(2)(Suppl. 1):s179 Abstract 699 (2006).
MacGilchrist et al., "Effect of the Serine Protease Inhibitor, Aprotinin, on Systemic Haemodynamics and Renal Function in Patients with Hepatic Cirrhosis and Ascites," Clin. Sci., 87:329-335 (1994).
Magklara et al., "Characterization of the enzymatic activity of human kallikrein 6: autoactivation, substrate specificity and regulation by inhibitors," Biochem. Biophys. Res. Commun., Aug. 8, 2003, vol. 307, No. 4, pp. 948-955, Abstract Only.
Mann et al., Hemostasis and Thrombosis, Chapter 10, 2nd Edition, Basic Principles and Clinical Practice: 148-161 (1987).
Mannucci, "Hemostatic Drugs" New England Journal of Medicine, Drug Therapy, 339(4):245-253 (1998).
March, Jerry, Advanced Organic Chemistry, 3rd Edition, Reactions, Mechanisms, and Structure, John Wiley and Sons, New York: 396-398; 1057-1060; 1099-1100 (1985).
Markland et al., "Iterative Optimization of High-Affinity Protease Inhibitors Using Phage Display. 1. Plasmin," Biochemistry, 35:8045-8057 (1996).
Markland et al., "Selection for Protease Inhibitors Using Bacteriophage Display," Methods Enzymol., 267:28-51 (1996).
Markland et al., Iterative optimization of high-affinity protease inhibitors using phage display. 2. Plasma kallikrein and thrombin. Biochemistry. Jun. 18, 1996;35(24):8058-67.
Mathews, C.K., et al., Biochemistry, The Benjamin Cummins Publishing Co., Inc., Redwood City, CA.: pp. 208-212, (1990).
Mattheakis, Larry C. et al. "An in vitro polysome display system for identifying ligands from very large peptide libraries" Proc. Natl. Acad. Sci. USA, (Sep. 1994), vol. 91, No. 19, pp. 9022-9026.
Maxfield et al., "Conformation of poly(ethylene oxide) in the solid state, melt and solution measured by Raman scattering," Polymer, 1975, vol. 16, pp. 505-509.
McCarty, "Crystal-induced inflammation of the joints," Annual Reviews of Medicine, vol. 21, pp. 357-366 (1970).
McConnell et al., "New Leupeptin Analogues: Synthesis and Inhibition Data," J. Med. Chem., 33:86-93 (1990).
Merriam-Webster reference for the term "prevent." web date: 2010. 2 pages.
Merrifield, B., "Solid Phase Synthesis," Science, 232:341-347 (1986).
Merrifield, R., "Solid Phase Peptide Synthesis. I. The Synthesis of a Tetrapeptide," J. Amer. Chem. Soc., 85:2149-2154 (1963).
Migliore, Alberto et al: "Open pilot study of ultrasound-guided intra-articular injection of hylan G-F 20 (Synvisc) in the treatment of symptomatic hip osteoarthritis", Clinical Rheumatology; Journal of the International League of Associations for Rheumatology, Springer-Verlag, LO, vol. 24, No. 3, pp. 285-289 (Jun. 1, 2005).
Mine et al., "Structural mechanism for heparin-binding of the third Kunitz domain of human tissue factor pathway inhibitor," Biochemistry, 2002, vol. 41, pp. 78-85.
Miyajima et al., "Secretion of Mature Mouse Interleukin-2 by Saccharomyces cerevisiae: Use of a General Secretion Vector Containing Promoter and Leader Sequences of the Mating Pheromone α-Factor," Gene, 37:155-161 (1985).
Molineux, Pegylation: "Engineering improved pharmaceuticals for enhanced therapy". Cancer Treatment Reviews, Apr. 2002. 28, Supplement A; 13-6.
Monteseirin. et al., "Plasma Kallikrein Amidolytic Activity in Bronchial Asthma," Allergol. Immunopathol., (Madr)., 20:211-214 (1992).
Moreland, "Intra-articular hyaluronan (hyaluronic acid) and hylans for the treatment of osteoarthritis: mechanisms of action," Arthritis Res. Ther., 2003, vol. 5, pp. 54-67.
Murkin et al., "Aprotinin significantly decreases bleeding and transfusion requirements in patients receiving aspirin and undergoing cardiac operations," J. Thorac. Cardiovasc. Surg., vol. 107, pp. 554-561 (1994).
Naess, et al., "Effects of a Combined Drug Regimen on Tumour Necrosis Factor and Plasma Kallikrein Activity in Experimental Endotoxaemia," Eur. J. Surg., 160:77-86 (1994).
Nagai and Sato, "Synthesis of a Bicyclic Dipeptide with the Shape of β-Turn Central Part ," Tetrahedron Lett., 26(5):647-650 (1985).
Nagai et al., "Bicyclic Turned Dipeptide (BTD) as a β-Turn Mimetic: its Design, Synthesis and Incorporation into Bioactive Peptides," Tetrahedron, 49:3577-3592 (1993).
Needleman; Wunsch, "A General Method Applicable to the Search for Similarities in the Amino Acid Sequence of Two Proteins". Mol. Biol., 1970, vol. 48, pp. 443-453.
Nektartm—Transforming Therapeutics, Nektar Advanced PEGylation: Polyethylene Glycol and Derivatives for Advanced PEGylation, pp. 1-24, catalogue 2004.
Nektartm—Transforming Therapeutics, Nektar Molecule Engineering: Polyethylene Glycol and Derivatives for Advanced PEGylation, pp. 1-20, catalogue—2003.
Neuhaus, et al., "Effect of Aprotinin on Intraoperative Bleeding and Fibrinolysis in Liver Transplantation," Lancet, 2: 924-925 (1989).
Ngo, et al., "Computational Complexity, Protein Structure Prediction, and the Levinthal Paradox", The Protein Folding Problem and Tertiary Structure Prediction, Chapter 14, pp. 433-440 and 492-495 only (1994).
Ning, el. al., "Production of recombinant humanized anti-HBsAg Fab fragment from Pichia pastoris by fermentation.", J Biochem Mol Biol. ;38(3):294-9. (May 31 2005).
NM_008455.2 (GI: 236465804): "Plasma kallikrein precursor", GenBank Record created on Dec. 29, 2010 GenBank [online] Bethesda, MD USA: United States National Library of Medicine, retrieved from internet using <URL: http://www.ncbi.nlm.nih.gov/nuccore/236465804?sat=14&satkey=4833839> GenBank Accession No. NM_008455.2 (GI: 236465804).
NM_012725.2 (GI:162138904): "Plasma kallikrein precursor", GenBank Record created on Dec. 26, 2010 GenBank [online] Bethesda, MD USA: United States National Library of Medicine, retrieved from internet using <URL: http://www.ncbi.nlm.nih.gov/nuccore/162138904?sat=14&satkey=5346361 > GenBank Accession No. NM_012725.2 (GI:162138904).
NOF Corporation, "PEG Derivatives, Phospholipid and Drug Delivery Materials for Pharmaceutical Products and Formulations," pp. 1-59, catalogue Ver. 8—Apr. 2006.

(56) References Cited

OTHER PUBLICATIONS

NOF Corporation, "PEG Derivatives, Phospholipid and Drug Delivery Materials for Pharmaceuticals," pp. 1-46, catalogue—2003, 1st.
NOF Corporation, "PEG Derivatives, Phospholipid and Drug Delivery Materials for Pharmaceuticals," pp. 1-50, catalogue—2003 2nd.
Non-Final Office Action for U.S. Appl. No. 11/931,635 dated Nov. 12, 2008, 8 pages.
Non-Final Office Action for U.S. Appl. No. 10/456,986 dated Oct. 21, 2004, 17 pages.
Non-Final Office Action for U.S. Appl. No. 10/953,902 dated Dec. 14, 2005, 10 pages.
Non-Final Office Action for U.S. Appl. No. 11/125,639 dated Jul. 5, 2006, 8 pages.
Non-Final Office Action for U.S. Appl. No. 11/322,960 dated Oct. 31, 2006, 9 pages.
Non-Final Office Action for U.S. Appl. No. 11/323,261 dated Aug. 2, 2006, 4 pages.
Non-Final Office Action for U.S. Appl. No. 11/323,261 dated Dec. 26, 2006, 5 pages.
Non-Final Office Action for U.S. Appl. No. 11/323,261 dated Mar. 22, 2007, 7 pages.
Non-Final Office Action for U.S. Appl. No. 11/466,979 dated Dec. 5, 2008, 8 pages.
Non-Final Office Action for U.S. Appl. No. 11/466,979 dated Jun. 12, 2008, 9 pages.
Non-Final Office Action for U.S. Appl. No. 11/796,272 dated Feb. 2, 2009, 11 pages.
Non-Final Office Action for U.S. Appl. No. 11/796,272 dated Jan. 13, 2010, 8 pages.
Non-Final Office Action for U.S. Appl. No. 11/804,388 dated Dec. 8, 2009, 9 pages.
Non-Final Office Action for U.S. Appl. No. 11/804,388 dated Jun. 10, 2011, 8 pages.
Non-Final Office Action for U.S. Appl. No. 11/804,388 dated Jun. 15, 2010, 12 pages.
Non-Final Office Action for U.S. Appl. No. 11/860,853 dated Apr. 17, 2009, 8 pages.
Non-Final Office Action for U.S. Appl. No. 11/929,685 dated Dec. 2, 2008, 13 pages.
Non-Final Office Action for U.S. Appl. No. 11/929,729 dated Aug. 26, 2009, 12 pages.
Non-Final Office Action for U.S. Appl. No. 11/929,729 dated Dec. 29, 2010, 9 pages.
Non-Final Office Action for U.S. Appl. No. 11/929,729 dated May 26, 2010, 9 pages.
Non-Final Office Action for U.S. Appl. No. 11/929,822 dated Feb. 9, 2010, 6 pages.
Non-Final Office Action for U.S. Appl. No. 11/929,822 dated Jan. 10, 2011, 5 pages.
Non-Final Office Action for U.S. Appl. No. 11/929,876 dated Dec. 1, 2009, 10 pages.
Non-Final Office Action for U.S. Appl. No. 11/930,012 dated Aug. 27, 2009, 9 pages.
Non-Final Office Action for U.S. Appl. No. 11/930,018 dated Nov. 12, 2008, 14 pages.
Non-Final Office Action for U.S. Appl. No. 11/930,700 dated Nov. 9, 2009, 8 pages.
Non-Final Office Action for U.S. Appl. No. 11/930,802 dated Jan. 8, 2010, 9 pages.
Non-Final Office Action for U.S. Appl. No. 11/930,897 dated Nov. 6, 2009, 9 pages.
Non-Final Office Action for U.S. Appl. No. 11/931,361 dated Dec. 8, 2009, 8 pages.
Non-Final Office Action for U.S. Appl. No. 11/931,361 dated Jun. 15 2010, 10 pages.
Non-Final Office Action for U.S. Appl. No. 11/931,373 dated Jun. 12, 2009, 7 pages.
Non-Final Office Action for U.S. Appl. No. 11/931,373 dated May 4, 2010, 11 pages.
Non-Final Office Action for U.S. Appl. No. 11/931,665 dated Dec. 2, 2009, 10 pages.
Non-Final Office Action for U.S. Appl. No. 11/931,665 dated Jun. 14, 2010, 12 pages.
Non-Final Office Action for U.S. Appl. No. 11/931,810 dated Dec. 9, 2009, 10 pages.
Non-Final Office Action for U.S. Appl. No. 11/931,810 dated Jul. 12, 2010, 17 pages.
Non-Final Office Action for U.S. Appl. No. 11/931,941 dated Oct. 28, 2009, 8 pages.
Non-Final Office Action for U.S. Appl. No. 11/932,015 dated Oct. 27, 2009, 7 pages.
Non-Final Office Action for U.S. Appl. No. 11/932,098 dated Mar. 5, 2010, 12 pages.
Non-Final Office Action for U.S. Appl. No. 11/932,184 dated Oct. 27, 2009, 8 pages.
Non-Final Office Action for U.S. Appl. No. 12/951,543 dated Feb. 12, 2013, 10 pages.
Non-Final Office Action on U.S. Appl. No. 11/796,272 dated Jul. 31, 2009, 11 pages.
Non-Final Office Action on U.S. Appl. No. 13/228,300 dated Dec. 11, 2013, 12 pages.
Non-Final Office Action on U.S. Appl. No. 13/458,086 dated Feb. 28, 2013, 15 pages.
Notice of Allowance for U.S. Appl. No. 10/456,986 dated Dec. 21, 2005, 6 pages.
Notice of Allowance for U.S. Appl. No. 10/953,902 dated May 31, 2006, 8 pages.
Notice of Allowance for U.S. Appl. No. 11/125,639 dated Mar. 19, 2007, 6 pages.
Notice of Allowance for U.S. Appl. No. 11/323,261 dated Jun. 27, 2007, 6 pages.
Notice of Allowance for U.S. Appl. No. 11/466,979 dated Aug. 13, 2009, 7 pages.
Notice of Allowance for U.S. Appl. No. 11/466,979 dated Dec. 4, 2009, 6 pages.
Notice of Allowance for U.S. Appl. No. 11/804,388 dated Feb. 16, 2012, 8 pages.
Notice of Allowance for U.S. Appl. No. 11/929,729 dated Dec. 12, 2011, 10 pages.
Notice of Allowance for U.S. Appl. No. 11/929,822 dated Jun. 10, 2011, 9 pages.
Notice of Allowance for U.S. Appl. No. 11/930,012 dated Jun. 3, 2010, 7 pages.
Notice of Allowance for U.S. Appl. No. 11/931,373 dated Sep. 22, 2010, 13 pages.
Notice of Allowance for U.S. Appl. No. 12/951,543 dated Dec. 12, 2013, 11 pages.
Notice of Allowance for U.S. Appl. No. 13/458,086 dated Dec. 20, 2013, 8 pages.
Novotny et al., "Purification and Characterization of the Lipoprotein-Associated Coagulation Inhibitor from Human Plasma," J Biol. Chem., 264:18832-18837 (1989).
NP_000217.2 (GI:55956899): "keratin, type I cytoskeletal 9", GenBank Record created on Dec. 27, 2010 GenBank [online] Bethesda, MD USA: United States National Library of Medicine, retrieved from internet using <URL: http://www.ncbi.nlm.nih.gov/protein/55956899?sat=14&satkey=4890700> GenBank Accession No. NP_000217.2 (GI:55956899).
NP_000418.2 (GI:109255251): "loricrin", GenBank Record created on Nov. 3, 2010 GenBank [online] Bethesda, MD USA: United States National Library of Medicine, retrieved from internet using <URL:http://www.ncbi.nlm.nih.gov/ protein/109255251?sat=14&satkey=6156833> GenBank Accession No. NP_000418.2 (GI:109255251).
NP_000883.2 (GI: 78191798): "Plasma kallikrein preproprotein". GenBank Record created on Nov. 21, 2010, GenBank [online] Bethesda, MD USA: United States National Library of Medicine, retrieved from internet using <URL: http://www.ncbi.nlm.nih.gov/protein/78191798?sat=14&satkey=4530481> GenBank Accession No. NP_000883.2 (GI: 78191798).

(56) References Cited

OTHER PUBLICATIONS

NP_000892 (GI: 158508572): "mineralocorticoid receptor isoform 1", GenBank Record created on Dec. 27, 2010, GenBank [online] Bethesda, MD USA: United States National Library of Medicine, retrieved from internet using <URL: http://www.ncbi.nlm.nih.gov/protein/158508572?sat=14&satkey=4536058> GenBank Accession No. NP_000892.2 (GI: 158508572).
NP_005850.1 (GI:5032007): "transcriptional activator protein Pur-alpha", GenBank Record created on Dec. 28, 2010, GenBank [online] Bethesda, MD USA: United States National Library of Medicine, retrieved from internet using <URL: http://www.ncbi.nlm.nih.gov/protein/5032007?sat=14&satkey=4526134> GenBank Accession No. NP_005850.1 (GI:5032007).
NP_006228.3 (GI:110347449): "POU domain, class 4, transcription factor 1", GenBank Record created on Dec. 27, 2010, GenBank [online] Bethesda, MD USA: United States National Library of Medicine, retrieved from internet using <URL:http://www.ncbi.nlm.nih.gov/protein/110347449?sat=14&satkey=4536081> GenBank Accession No. NP_006228.3 (GI:110347449).
NP_009060.2 (GI:22547197): "zinc finger protein ZIC 2", GenBank Record created on Dec. 24, 2010, GenBank [online] Bethesda, MD USA: United States National Library of Medicine, retrieved from internet using <URL: http://www.ncbi.nlm.nih.gov/protein/22547197?sat=14&satkey=4290853> GenBank Accession No. NP_009060.2 (GI:22547197).
NP_031393.2 (GI:21396480): "RNA-binding protein Raly isoform 2", GenBank Record created on Dec. 25, 2010, GenBank [online] Bethesda, MD USA: United States National Library of Medicine, retrieved from internet using <URL: http://www.ncbi.nlm.nih.gov/protein/21396480?sat=14&satkey=4835374> GenBank Accession No. NP_031393.2 (GI:21396480).
NP_032481.2 (GI: 236465805): "Plasma kallikrein precursor", GenBank Record created on Dec. 29, 2010 GenBank [online] Bethesda, MD USA: United States National Library of Medicine, retrieved from internet using <URL: http://www.ncbi.nlm.nih.gov/protein/236465805?sat=14&satkey=4833839> GenBank Accession No. NP_032481.2 (GI:236465805).
NP_036857.2 (GI:162138905): "Plasma kallikrein precursor", GenBank Record created on Dec. 26, 2010 GenBank [online] Bethesda, MD USA: United States National Library of Medicine, retrieved from internet using <URL: http://www.ncbi.nlm.nih.gov/protein/162138905?sat=14&satkey=5346361 > GenBank Accession No. NP_036857.2 (GI:162138905).
NP_056932.2 (GI:153791670): "Plasma kallikrein preproprotein", GenBank Record created on Dec. 27, 2010, GenBank [online] Bethesda, MD USA: United States National Library of Medicine, retrieved from internet using <URL: http://www.ncbi.nlm.nih.gov/protein/153791670?sat=14&satkey=4553701 > GenBank Accession No. NP_056932.2 (GI:153791670).
NP_061856.1 (GI:9506713): "H/ACA ribonucleoprotein complex subunit 1", GenBank Record created on Dec. 24, 2010, GenBank [online] Bethesda, MD USA: United States National Library of Medicine, retrieved from internet using <URL: http://www.ncbi.nlm.nih.gov/protein/9506713?sat=14&satkey=4524138> GenBank Accession No. NP_061856.1 (GI:9506713).
NP_065104.1 (GI:9966841 ): "cell death regulator Aven", GenBank Record created on Dec. 26, 2010, GenBank [online] Bethesda, MD USA: United States National Library of Medicine, retrieved from internet using <URL: http://www.ncbi.nlm.nih.gov/protein/9966841?sat=14&satkey=4843224> GenBank Accession No. NP_065104.1 (GI:9966841).
NP_115818.2 (GI:53829370): "neuralized-like protein 4 isoform 1", GenBank Record created on Dec. 27, 2010, GenBank [online] Bethesda, MD USA: United States National Library of Medicine, retrieved from internet using <URL: http://www.ncbi.nlm.nih.gov/protein/53829370?sat=14&satkey=4560911 > GenBank Accession No. NP_ 115818.2 (GI:53829370).
NP_476429.2 (GI:109148552): "keratin, type II cytoskeletal 3 ", GenBank Record created on Dec. 24, 2010 GenBank [online] Bethesda, MD USA: United States National Library of Medicine, retrieved from internet using <URL: http://www.ncbi.nlm.nih.gov/protein/109148552?sat=14&satkey=6358709> GenBank Accession No. NP_NP_476429.2 (GI:109148552).
NP_631961.1 (GI:21327701): "TATA-binding protein-associated factor 2N isoform 1", GenBank Record created on Dec. 25, 2010, GenBank [online] Bethesda, MD USA: United States National Library of Medicine, retrieved from internet using <URL: http://www.ncbi.nlm.nih.gov/protein/21327701 ?sat=14 &satkey=4528109> GenBank Accession No. NP_631961.1 (GI:21327701 ).
NP_787059.2 (GI:40068462): "AT-rich interactive domain-containing protein 1B isoform 3", GenBank Record created on Mar. 4, 2010, GenBank [online] Bethesda, MD USA: United States National Library of Medicine, retrieved from internet using <URL: http://www.ncbi.nlm.nih.gov/protein/NP_787059.2?report=genpept> GenBank Accession No. NP_787059.2 (GI:40068462).
Nwariaku, et al., "Effect of a bradykinin antagonist on the local inflammatory response following thermal injury" Burns, 22:324-327 (1996).
Office Action for European Application No. 03757339.1 dated Aug. 20, 2008, 5 pages.
Office Action for European Application No. 03757339.1 dated Dec. 8, 2008, 4 pages.
Office Action for European Application No. 03757339.1 dated May 11, 2009, 4 pages.
Office Action for European Application No. 07023364.8 dated Mar. 18, 2010, 5 pages.
Office Action for European Application No. 10180484.7 dated Feb. 16, 2012, 5 pages.
Office Action for European Application No. 10180486.2 dated Dec. 17, 2013, 4 pages.
Office Action for European Application No. 10180486.2 dated Feb. 16, 2012, 4 pages.
Office Action for European Application No. 10180486.2 dated Nov. 3, 2014, 4 pages.
Official Action for Japanese Patent Application No. 2013-114068 dated Jun. 25, 2014, 2 pages. (English translation not available).
Okamoto, et al., "A Finding of Highly Selective Synthetic Inhibitor of Plasma Kallikrein; Its Action to Bradykinin Generation, Intrinsic Coagulation and Experimental DIC," Agents Actions Suppl., 38(1):198-205 (1992).
O'Reilly et al., "Angiostatin: A Novel Angiogenesis Inhibitor That Mediates the Suppression of Metastases by a Lewis Lung Carcinoma," Cell, 79:315-328 (1994).
Pan et al., "Reperfusion injury following cerebral ischemia: pathophysiology, MR imaging, and potential therapies," Neuroradiology, 2007, vol. 49, pp. 93-102.
Park, et al., "Three Dimensional Structure of the Kringle Sequence: Structure of Prothrombin Fragment 1," Biochemistry, 25:3977-3982 (1986).
PCT International Search Report dated Jul. 21, 2008 and issued in PCT/US05/34335.
PCT Written Opinion dated Jul. 21, 2008 and issued in PCT/US05/34335.
Petersen et al., "Inhibitory properties of separate recombinant Kunitz-type-protease-inhibitor domains from tissue-factor-pathway inhibitor," Eur. J. Biochem., 1996, vol. 235, pp. 310-316.
Phillips, "The challenge of gene therapy and DNA dellicery," J. Pharm. Pharmacology, vol. 53, pp. 1169-1174 (2001).
Pintigny et al., "Aprotinin can inhibit the proteolytic activity of thrombin: a fluorescence and an enzymatic study," Eur. J. Biochem., 1992, vol. 207, pp. 89-95.
Piro et al., "Role for the Kunitz-3 domain of tissue factor pathway inhibitor-a in cell surface binding," Circulation, 2004, vol. 110, pp. 3567-3572.
Pirollo et al.. "Targeted delivery of small interfering RNA: approaching effective cancer therapies," Cancer Res., 2008, vol. 68, No. 5, pp. 1247-1250.
Pitt et al., "Rabbit monoarticular arthritis as a model for intra-articular drug injections. The local action of administered cortisol and alpha-1 proteinase inhibitor." Agents and Actions, vol. 15, No.

(56) References Cited

OTHER PUBLICATIONS 5-6, abstract online, retrieved from internet <URI:http://www.springerlink.com/content/j82860503948741/p> (Dec. 1984).
Polypure, Products; PEG amines; PEG acids and amino acids, PEG thiols and disulfides; Biotins, Apr. 2005.
Polypure, Products; PEG amines; PEG acids and amino acids; PEG thiols and disulfides; Biotins, Apr. 2004.
Poznansky et al., "Growth hormone-albumin-conjugates reduced renal toxicity and altered plasma clearance," 1988, vol. 239, pp. 18-22.
Putterman, C., "Aprotinin Therapy in Septic Shock," Acta Chir. Scand., 155:367 (1989).
Quanta Biodesign, Labeling, Derivatization and Crosslinking Reagents for Biological and Related Materials with dPEGTM, pp. 1-38, Mar. 12, 2004.
Quanta Biodesign, Labeling, Modification and Crosslinking Reagents incorporating our unique monodispersed dPEGTM, pp. 1-31, Nov. 5, 2004.
Quanta Biodesign, Leading innovator, producer and provider of monodisperse discrete PEGTM (dPEGTM) derivatives, Product Catalogue, pp. 1-51, Updated: Jul. 18, 2005.
Quanta Biodesign, Leading innovator, producer and provider of monodisperse discrete PEGTM (dPEGTM) derivatives, Product Catalogue, pp. 1-51, Updated: Nov. 17, 2005.
R. Durbin et al., "Biological sequence analysis: probabilistic models of proteins and nucleic acids", Cambridge University Press, 1998.
Rahman et al., "Identification and functional importance of plasma kallikrein in the synovial fluids of patients with rheumatoid, psoriatic, and osteoarthritis," Annals of the Rheumatic Diseases, vol. 54, pp. 345-350 (1995).
Reichert, "Technology evaluation: lumiliximab, Biogen Idec" Curr Opin Mol Ther., 6(6):675-83 (2004). (Abstract only).
Robbins, K.C. et al., Hemostasis and Thrombosis, Chapter 21, 2nd Edition, Basic Principles and Clinical Practice: 340-357 (1987).
Roberts et al., "Directed evolution of a protein: selection of potent neurtophil elastase inhibitor displayed on M13 fusion phage," PNAS USA, vol. 89, pp. 2429-2433 (1992).
Roberts et al., "Protease inhibitor display M13 phage: selection of high-affinity neurtophil elastase inhibitors," Gene, vol. 121, pp. 9-15 (1992).
Roberts, M.J. et al., "Chemistry for peptide and protein PEGylation", Advanced Drug Delivery Reviews, 54, pp. 459-476, 2002.
Rossi, E. et al., The Synthetic Peptide DX88 Binds to Endothelial Cells In Vitro and Retains the Inhibitory Activity on Kallikrein, International Immunopharmacology 2(9):1313, Abstract 142 (2002).
Sainz I.M. et al., "Fifty years of research on the plasma kallikrein-kinin system: from protein structure and function to cell biology and in-vivo pathophysiology" Thromb Haemost 98, 77-83, 2007.
Sartor, R.B., et al., "Selective Kallikrein-Kinin System Activation in Inbred Rats Differentially Susceptible to Granulomatous Enterocolitis," Gastroenterology, 110:1467-1481 (1996).
Scarff et al., "Targeted disruption of SP13/Serpinb6 does not result in development of growth defects, leukocyte dysfunction, or susceptibility to stroke," Molecular and Cellular Biology, May 2004, pp. 4075-4082.
Scatchard, George, The Attractions of Proteins for Small Molecules and Ions, Ann. NY Acad. Sci, 51:660-672 (1949).
Schechter, et al., On the Active Site of Proteases, III. Mapping the Active Site of Papain; Specific Peptide Inhibitors of Papain, Biochemical and Biophysical Research Communications, vol. 32 (5): 898-902, (1968).
Schechter, et al., On the Size of the Active Site on Proteases, I. Papain, Biochemical and Biophysical Research Communications, vol. 27 (2): 157-162, (1967).
Schmaier A.H."Assembly, activation, and physiologic influence of the plasma kallikrein/kinin system" (2008) Int Immunopharmacology, 161-165.
Schmaier et al., Hemostasis and Thrombosis, Chapter 2, 2nd Edition, Basic Principals and Clinical Practice: 18-38 (1987).
Schmid-Elsaesser, et al., "A critical reevaluation of the intraluminal thread model of focal cerebral ischemia: evidence of inadvertent premature reperfusion and subarachnoid hemorrhage in rats by laser-Doppler flowmetry" Stroke 29 (10): 2162-70 (1989).
Schmidt et al., "A male accessory gland peptide with protease inhibitory activity in Drosophila funebris," Swiss-Prot, Accession #P11424 (1992).
Schnabel et al., Aprotinin: Preparation by Partial Desulphurization of Aprotinin by Means of Raney Nickel and Comparison with Other Aprotinin Derivatives, Biol. Chem. Hoppe-Seyler, 367:1167-1176 (1986).
Schoonooghe, et. al., "Efficient production of human bivalent and trivalent anti-MUC1 Fab-scFv antibodies in Pichia pastoris", BMC Biotechnol. Aug. 11, 2009;9:70.
Schopf, "IDEC-114 (IDEC)" Curr Opin Investig Drugs, 2(5):635-8 (2001). (Abstract only).
Schultz et al., "Smart, a simple modular architecture research tool: Identification of signaling domains," Proc. Natl. Acad. Sci. USA, 1998, vol. 95, p. 5857.
Schultz et al., "Smart: a web-based tool for the study of genetically mobile domains," Nucl. Acids Res, 2000, vol. 28, p. 231-234.
Schwarz et al., "Stability studies on derivatives of the bovine trypsin inhibitor," Biochemistry, vol. 26, pp. 3544-3551 (1987).
Shearwater Polymers, Inc., Polyethylene Glycol and Derivatives, pp. 1-50, catalogue—Jul. 1997.
Shearwater Corporation, Polyethylene Glycol and Derivatives for Biomedical Applications, pp. 1-17, catalogue—2001.
Shearwater Polymers, Inc., Polyethylene Glycol Derivatives: Functionalized Biocompatible Polymers for Research and Pharmaceuticals, pp. 1-50, catalogue—2000.
Shearwater Polymers, Inc., pp. 2-49, catalogue—Mar. 1995.
Sheppard, et al., Acid-Labile Resin Linkage Agents for Use in Solid Phase Peptide Synthesis, Int. J. Peptide Protein Res., 20:451-454 (1982).
Sheridan, et al., A Multicenter Trial of the Use of the Proteolytic Enzyme Inhibitor Aprotinin in Colorectal Surgery, Dis. Colon Rectum, 32:505-508 (1989).
Sherman et al., "Chapter 11: Conjugation of high-molecular weight poly(ethylene glycol) to cytokines: granulocyte- macrophage colony-stimulating factors as model substrates," American Chemical Society, 1997, pp. 155-169.
Shibuya, et. al., "Primary Structure of Guinea Pig Plasma Prekallikrein", Immunopharmacology, vol. 45 (1-3), p. 127-34, Abstract p. 131, Fig 1, 2 (1999).
Siebeck et al., "Inhibition of plasma kallikrein with aprotinin in porcine endotoxin shock," J. Trauma, vol. 34, pp. 193-198 (1993).
Sik Eum Wet al: "In vivo protein transduction: biologically active intact pep-1-superoxide dismutase fusion protein efficiently protects against ischemic insult", Free Radical Biology and Medicine, Elsevier Science, US, vol. 37, No. 10, Nov. 15, 2004, pp. 1656-1669.
Silverberg, M. et al: "Blood: Principles and Practice of Hematology", 1995, JB Lippincott Co, article "The Contact System and its Disorders".
Skolnick and Fetrow, From Genes to Protein Structure and Function: Novel Applications of Computational Approaches in the Genomic Era; Trends in Biotechnology, vol. 18, pp. 34-39 (2000).
Skolnick et al. (Trends in Biotech. 18: 34-39, 2000).
Sonhammer et al., "Pfam: A Comprehensive Database of Protein Domain Families Based on Seed Alignments," Proteins, 1997, vol. 28 (3), pp. 405-420.
Sonis et al. "An animal model for mucositis induced by cancer chemotherapy" (1990) Oral Surg Oral Med Oral Pathol. 69:437-43.
Sonis et al. "Validation of a new scoring system for the assessment of clinical trial research of oral mucositis induced by radiation or chemotherapy. Mucositis Study Group." (1999) Cancer 85:2103-13.
Sprecher et al., "Molecular Cloning, Expression, and Partial Characterization of a Second Human Tissue-Factor-Pathway Inhibitor," Proc. Natl., Acad. Sci. USA, 91:3353-3357 (1994).

(56) References Cited

OTHER PUBLICATIONS

Stadnicki et al., "Activation of plasma contact and coagulation systems and neutrophils in the active phase of ulcerative colitis," Digestive Diseases and Sciences, 1997, vol. 42, No. 1, pp. 2356-2366.
Stadnicki et al., "Activation of the Kallikrein-Kinin System in Indomethacin-Induced Entercolitis in Genetically Susceptible Rats," J. Invest. Med., 44:299A (1996).
Stadnicki et al.. "Selective Plasma Kallikrein Inhibitor Attenuates Acute Intestinal Inflammation in Lewis Rat." Dig. Dis. Sci., 41:912-920 (1996).
Stewart, J.; Young, J., "Solid-Phase Peptide Synthesis", W.H. Freeman Co, 1989.
Strom et al., Therapeutic Immunology, Austen et al. (Ed.), Blackwell Science, Cambridge MA, 1996; pp. 451-456.
Stultz et al., "Structural analysis based on state-space modeling," Protein Sci., 1993, vol. 2, pp. 305-314.
Sunkureddi et al., "Clinical signs of gout," Hospital Physician, 2006, pp. 39-41.
Supplemental European Search Report and Search Opinion from European Application No. 3791557.6 dated Oct. 19, 2007.
Supplemental European Search Report from EP App. No. 04786615.7 dated Jan. 20, 2009.
Supplemental Final Office Action on U.S. Appl. No. 11/930,018 dated Mar. 18, 2010, 13 pages.
Supplementary European Search Report and European Search Opinion for European Application No. 05799587.0 dated Nov. 28, 2012, 27 pages.
Supplementary European Search Report dated Jan. 19, 2009 from EP App. No. 04782687.0.
Supplementary European Search Report for EP Application No. 03757339.1, mail date Apr. 23, 2008, 3 pages.
Supplementary European Search Report from European Application No. 8798232 dated Feb. 1, 2012.
Supplementary European Search Report including the European Search Opinion from corresponding European Application No. EP06848187.8, dated Dec. 7, 2009.
Taby et al., "Inhibition of activated protein C by aprotinin and the uses of the insolubilized inhibitor for its purification," Thrombosis Research, 1990, vol. 59, pp. 27-35.
Taggart et al., "Inactivation of human-b-defensins 2 and 3 by elastolytic cathepsins1 ," The Journal of Immunology, 2003, vol. 170, pp. 931-937.
Takahashi, et al., "Production of humanized Fab fragment against human high affinity IgE receptor in Pichia pastoris" Biosci Biotechnol Biochem 64(10):2138-44 (2000).
Tamura, et al., "Focal cerebral ischemia in the rat: 1. Description of technique and early neuropathological consequences following middle cerebral artery occlusion" J Cereb Blood Flow Metab 1: 53-60 (1981).
The Merck Index: pp. 145, 263, 427, 428, 1183, and 1184, (1989).
Tian et al., "Synthesis of optically pure Cα-methyl-arginine," Int. J. Peptide Protein Res., 40: 119-126 (1992).
Travis et al., "Pulmonary perspective: potential problems in designing elastase inhibitors for therapy," Am. Rev. Respir. Dig., 1991, vol. 143, pp. 1412-1415.
Tremblay et al., "Anti-inflammatory activity of neutrophil elastase inhibitors," Current Opinion in Investigational Drugs, 2003, vol. 4, No. 5, pp. 556-565.
Tschesche et al., "Semisynthetic engineering of proteinase inhibitor homologues," Biochim. Biophys. Acta, 1987, vol. 913, pp. 97-101 (1987).
Uebel,"Die behandlung con kniegelenksarthrosen mit trasylol," Langenbacks Arch. Chir., vol. 325, pp. 356-358 (1969). English Abstract Only.
Urlaub et al., "Isolation of Chinese hamster cell mutants deficient in dihydrofolate reductase activity", Proc. Natl. Acad. Sci. USA 77:4216-4220 (1980).
van der Logt et al., "Intron-Exon Organization of the Human Gene Coding for the Lipoprotein-Associated Coagulation Inhibitor: The Factor Xa Dependent Inhibitor of the Extrinsic Pathway of Coagulation," Biochem., 30: 1571-1577 ( 1991).
van Dijl et al., "Signal peptidase I of Bacillus subtilis: patterns of conserved amino acids in prokaryotic and eukaryotic type I signal peptidases," EMBO J., 11:2819-2828 (1992).
Varadi and Patthy, "Location of Plasminogen-Binding Sites in Human Fibrin(ogen)," Biochem., 22:2440-2446 (1983).
Varadi and Patthy, "Segment of Fibrinogen is in a Region Essential for Plasminogen Binding by Fibrin Fragment E," Biochem., 23:2108-2112 (1984).
Vedvick, et al., "High-Level Secretion of Biologically Active Aprotinin from the Yeast Pichia Pastoris," J. Ind. Microbiol., 7:197-201 (1991).
Veronese, "Peptide and protein PEGylation: a review of problems and solutions," Biomaterials, Mar. 1, 2001, vol. 22, No. 5, pp. 405-417.
Vidal et al., "Making sense of antisense," European Journal of Cancer, 2005, vol. 41, pp. 2812-2818.
Viswanathan M. et al., "Engineered protein protease inhibitors", Current Enzyme Inhibition, Jan. 1, 2009, pp. 87-98, vol. 5, No. 2, Betham Science Publishers Ltd., Hilversum, NL.
Volpe-Junior et al., "Augmented plasma and tissue kallikrein like activity in synovial fluid of patients with inflammatory articular diseases," Inflamm. Res., 1996, vol. 45, pp. 198-202.
Wade et al., "Solid-Phase Synthesis of α-Human Atrial Natriuretic Factor: Comparison of the Boc-Polystyrene and Fmoc-Polyamide Methods," Biopolymers, 25:S21-37 (1986).
Wagner et al., "High Level Expression, Purification, and Characterization of the Kunitz-Type Protease Inhibitor Domain of Protease Nexin-2/Amyloid β-Protein Precursor," Biochem. Biophys. Res. Comm., 186:1138-1145 (1992).
Wang et al., "Monitoring of heparin-induced anticoagulation with kaolin-activated clotting time in cardiac surgical patients treated with aprotinin," Anesthesiology, vol. 77, pp. 1080-1084 (1992).
Wark P.A., "DX-890 (Dyax)", iDrugs, 5, pp. 586-589, Jun. 2002.
Wellington et al., "Tranexamic Acid: A review of its use in the management of menorrhagia", Drugs, vol. 63, No. 13, pp. 1417-1433, 2003.
Wells. "Addivity of Mutational Effects in Proteins". Biochemistry, vol. 29 (37), pp. 8509-8517 (1990).
Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).
Wilson, et al., "The Calculation and Synthesis of a Template Molecule," Tetrahedron, 49:3655-3663 (1993).
Wood, Alastair, J.J, "Hemostatic Drugs" New England Journal of Medicine, Drug Therapy, vol. 339, No. 4, pp. 245-253 (1998).
Worthy et al., "Current status review kallikreins and kinins: mediators in inflammatory joint disease," Int. J. Exp, 1990.
Worthy, K. et al., "Kallikreins and Kinins: Mediators in Inflammatory Joint Disease?", International Review of Experimental Pathology, pp. 587-601, vol. 71, No. 4, Blackwell Scientific, Oxford GB (Aug. 1, 1990).
Written Opinion from International Application No. PCT/US05/34335 dated Jul. 21, 2008.
Written Opinion from International Application No. PCT/US11/20377 dated Jun. 28, 2011.
Written Opinion from International Application No. PCT/US2008/074061 dated Dec. 29, 2008.
Wun et al., "Cloning and Characterization of a cDNA Coding for the Lipoprotein-associated Coagulation Inhibitor Shows that it Consists of Three Tandem Kunitz-type Inhibitory Domains," J. Biol. Chem., 263:6001-6004 (1988).
XP_376532.2 (GI:51465288): "Predicted: KIAA0408", GenBank Record created on Aug. 19, 2004, GenBank [online] Bethesda, MD USA: United States National Library of Medicine, retrieved from internet using <URL:http://www. ncbi.nlm.nih.gov/protein/XP _376532.2?report=genpepl > GenBank Accession No. XP_376532.2 (GI:51465288).

(56) References Cited

OTHER PUBLICATIONS

Xu et al., "The crystal structure of bikunin from the inter-a-inhibitor complex: a serine protease inhibitor with two Kumit2 domains," J. Mol. Biol. Mar. 13, 1998, vol. 276, No. 5, pp. 955-966.
Feener, Plasma kallikrein and diabetic macular edema. Curr Diab Rep. Aug. 2010;10(4):270-5.
Phipps et al., Plasma kallikrein mediates angiotensin II type 1 receptor-stimulated retinal vascular permeability. Hypertension. Feb. 2009;53(2):175-81. Epub Jan. 5, 2009.
PCT/EP2007/002216, May 15, 2008, International Search Report and Written Opinion.
PCT/EP2007/002216, Sep. 1, 2008, International Preliminary Report on Patentability.
PCT/US2005/034335, Mar. 3, 2009, International Preliminary Report on Patentability.
PCT/US2004/028257, Jun. 6, 2006, International Preliminary Report on Patentability.
Boyd et al., Correlation of increased vascular endothelial growth factor with neovascularization and permeability in ischemic central vein occlusion. Arch Ophthalmol. Dec. 2002;120(12):1644-50.
Frumento et al., Stroke after cardiac surgery: a retrospective analysis of the effect of aprotinin dosing regimens. Ann Thorac Surg. Feb. 2003;75(2):479-83; discussion 483-4.
Nambu et al., Angiopoietin 1 inhibits ocular neovascularization and breakdown of the blood-retinal barrier. Gene Ther. May 2004;11(10):865-73.
Roos et al., Antifibrinolytic therapy for aneurysmal subarachnoid haemorrhage. Cochrane Database Syst Rev. 2003;(2):CD001245. Review. Update in: Cochrane Database Syst Rev. 2013;8:CD001245.
U.S. Appl. No. 11/860,853, filed Sep. 25, 2007.
U.S. Appl. No. 15/175,644, filed Jun. 7, 2016.
U.S. Appl. No. 11/930,700, filed Oct. 31, 2007.

5AOX1 →　　　　　　　　　　　　　　　　　　　　　　　　　　　　　EstB I

CG ACT TTT AAC GAC AAC TTG AGA AGA TCA AAA AAC AAC TAA TTA TTC GAA

ACG　　ATG AGA TTC CCA TCT ATC TTC ACT GCT GTT TTG TTC GCT GCT
　　　　 M   R   F   P   S   I   F   T   A   V   L   F   A   A

TCC TCT GCT TTG GCT GCT CCA GTT AAC ACC ACT ACT GAA GAC GAG ACT
 S   S   A   L   A   A   P   V   N   T   T   T   E   D   E   T

GCT CAA ATT CCT GCT GAG GCT GTC ATC GGT TAC TCT GAC TTG GAA GGT
 A   Q   I   P   A   E   A   V   I   G   Y   S   D   L   E   G

GAC TTC GAC GTC GCT GTT TTG CCA TTC TCT AAC TCT ACT AAC AAC GGT
 D   F   D   V   A   V   L   P   F   S   N   S   T   N   N   G

TTG TTG TTC ATC AAC ACT ACC ATC GCT TCT ATC GCT GCT AAG GAG GAA
 L   L   F   I   N   T   T   I   A   S   I   A   A   K   E   E

GGT GTT TCC CTC GAG AAG AGA | GAG GCT ATG CAC TCT TTC TGT GCT TTC
 G   V   S   L   E   K   R  |  E   A   M   H   S   F   C   A   F

AAG GCT GAC GAC GGT CCG TGC AGA GCT GCT CAC CCA AGA TGG TTC TTC
 K   A   D   D   G   P   C   R   A   A   H   P   R   W   F   F

AAC ATC TTC ACG CGT CAA TGC GAG GAG TTC ATC TAC GGT GGT TGT GAG
 N   I   F   T   R   Q   C   E   E   F   I   Y   G   G   C   E

GGT AAC CAA AAC AGA TTC GAG TCT CTA GAG GAG TGT AAG AAG ATG TGT
 G   N   Q   N   R   F   E   S   L   E   E   C   K   K   M   C

EcoR I
ACT AGA GAC | TAG TAA GAA TTC GCC TTA GAC ATG ACT GTT CCT CAG TTC
 T   R   D  |  *   *                                       ◄------
　　　　　　　　　　　　　　　　　　　　　　　　　　　　　　　　　　　　3'AOX1

AAG TTG GGC ACT TAC GAG AAG
　　　　　3'AOX1

FIG. 2

```
SEQ ID 2:(amino acids 3-60)----MHSF AFKA-DDGP RAAHPRNFFNIFTRQ EEFTYGG
SEQ ID 4:                    ----MHSF AFKA-DDGP KANHLRFFFNIFTRQ EEFSYGG
SEQ ID 5:                    ----MHSF AFKA-DDGH KANHQRFFFNIFTRQ EEFTYGG
SEQ ID 6:                    ----MHSF AFKA-DDGH KANHQRFFFNIFTRQ EQFTYGG
SEQ ID 7:                    ----MHSF AFKA-DDGH KASLPRFFFNIFTRQ EEFIYGG
SEQ ID 8:                    ----MHSF AFKA-DDGH KANHQRFFFNIFTRQ EEFSYGG
SEQ ID 9:                    ----MHSF AFKA-DDGH KGAHLRFFFNIFTRQ EEFIYGG
SEQ ID 10:                   ----MHSF AFKA-DDGR KGAHLRFFFNIFTRQ EEFIYGG
SEQ ID 11:                   ----MHSF AFKA-DGGR RGAHPRWFFNIFTRQ EEFSYGG
SEQ ID 12:                   ----MHSF AFKA-DDGP RAAHPRWFFNIFTRQ EEFSYGG
SEQ ID 13:                   ----MHSF AFKA-DVGR RGAHPRWFFNIFTRQ EEFSYGG
SEQ ID 14:                   ----MHSF AFKA-DVGR RGAQPRFFFNIFTRQ EEFSYGG
SEQ ID 15:                   ----MHSF AFKA-DDGS RAAHLRWFFNIFTRQ EEFSYGG
SEQ ID 16:                   ----MHSF AFKA-EGGS RAAHQRWFFNIFTRQ EEFSYGG
SEQ ID 17:                   ----MHSF AFKA-DDGP RGAHLRFFFNIFTRQ EEFSYGG
SEQ ID 18:                   ----MHSF AFKA-DDGH RGALPRWFFNIFTRQ EEFSYGG
SEQ ID 19:                   ----MHSF AFKA-DSGN RGNLPRFFFNIFTRQ EEFSYGG
SEQ ID 20:                   ----MHSF AFKA-DSGR RGNHQRFFFNIFTRQ EEFSYGG
SEQ ID 21:                   ----MHSF AFKA-DGGR RAIQPRWFFNIFTRQ EEFSYGG
SEQ ID 22:                   ----MHSF AFKA-DDGR RGAHPRWFFNIFTRQ EEFSYGG
BPTI(SEQ ID 29):             ----RPDF LEPP-YTGP KARIIRYFYNAKAGL QTFVYGG
ITI-D1(SEQ ID 30):           ----KEDS QLGY-SAGP MGMTSRYFYNGTSMA ETFQYGG
ITI-D2(SEQ ID 31):           ----TVAA NLPI-VRGP RAFIQLWAFDAVKGK VLFPYGG
LACI-D1(SEQ ID 32):          ----MHSF AFKA-DDGP KAIMKRFFFNIFTRQ EEFIYGG
LACI-D2(SEQ ID 33):          ----KPDF FLEE-DPGI RGYITRYFYNNQTKQ ERFKYGG
LACI-D3(SEQ ID 34):          ----GPSW LTPA-DRGL RANENRFYYNSVIGK RPFKYSG
HKI B9(SEQ ID 35):           ----LPNV AFPM-EKGP QTYMTRWFFNFETGE ELFAYGG
C-3(SEQ ID 36):              ----ETDI KLPK-DEGT RDFILKWYYDPNTKS ARFWYGG
TFPI-2 D1(SEQ ID 37):        ----NAEI LLPL-DYGP RALLLRYYYDRYTQS RQFLYGG
TFPI-2 D2(SEQ ID 38):        ----VPKV RLQVSVDDQ EGSTEKYFFNLSSMT EKFFSGG
TFPI-2 D3(SEQ ID 39):        ----IPSF YSPK-DEGL SANVTRYYFNPRYRT DAFTYTG
APP-I(SEQ ID 40):            ---RNREV SEQA-ETGP RAMISRWYFDVTEGK APFFYGG
EpiNE7(SEQ ID 41):           ----RPDF LEPP-YTGP VAMFPRYFYNAKAGL QTFVYGG
BITI-E7-141(SEQ ID 42):      ----RPDF QLGY-SAGP VAMFPRYFYNGTSMA QTFVYGG
MUTT26A(SEQ ID 43):          ----RPDF QLGY-SAGP VAMFPRYFYNGASMA QTFVYGG
MUTQE(SEQ ID 44):            ----RPDF QLGY-SAGP VAMFPRYFYNGTSMA ETFVYGG
MUT1619(SEQ ID 45):          ----RPDF QLGY-SAGP VGMFSRYFYNGTSMA QTFVYGG
EPI-HNE-1(SEQ ID 46):        EAEARPDF LEPP-YTGP IAFFPRYFYNAKAGL QTFVYGG
EPI-HNE-2(SEQ ID 47):        ------AA NLPI-VRGP IAFFPRWAFDAVKGK VLFPYGG
EPI-HNE-3(SEQ ID 48):        ------AA NLPI-VRGP IAFFPRWAFDAVKGK VLFPYGG
EPI-HNE-4(SEQ ID 49):        ------EA NLPI-VRGP IAFFPRWAFDAVKGK VLFPYGG
DPI14 KR(SEQ ID 50):         --EAVREV SEQA-ETGP IAFFPRWYFDVTEGK APFFYGG
DPI24 KR(SEQ ID 51):         --EANAEI LLPL-DYGP IAFFPRYYYDRYTQS RQFLYGG
DPI68 KR(SEQ ID 52):         --EAKPDF FLEE-DPGI IGFFPRYFYNNQAKQ ERFVYGG
DPI84 KR(SEQ ID 53):         --EAETDI KLPK-DEGT IAFFPRWYYDPNTKS ARFVYGG
```

FIG. 3A

```
SEQ ID  2: (cont.)            EGNQ--NRFESLEE KKM TRD
SEQ ID  4: (cont.)            GGNQ--NRFESLEE KKM TRD
SEQ ID  5: (cont.)            GGNQ--NRFESLEE KKM TRD
SEQ ID  6: (cont.)            AGNQ--NRFESLEE KKM TRD
SEQ ID  7: (cont.)            GGNQ--NRFESLEE KKM TRD
SEQ ID  8: (cont.)            GGNQ--NRFESLEE KKM TRD
SEQ ID  9: (cont.)            EGNQ--NRFESLEE KKM TRD
SEQ ID 10: (cont.)            EGNQ--NRFESLEE KKM TRD
SEQ ID 11: (cont.)            GGNQ--NRFESLEE KKM TRD
SEQ ID 12: (cont.)            GGNQ--NRFESLEE KKM TRD
SEQ ID 13: (cont.)            GGNQ--NRFESLEE KKM TRD
SEQ ID 14: (cont.)            GGNQ--NRFESLEE KKM TRD
SEQ ID 15: (cont.)            GGNQ--NRFESLEE KKM TRD
SEQ ID 16: (cont.)            GGNQ--NRFESLEE KKM TRD
SEQ ID 17: (cont.)            GGNQ--NRFESLEE KKM TRD
SEQ ID 18: (cont.)            GGNQ--NRFESLEE KKM TRD
SEQ ID 19: (cont.)            GGNQ--NRFESLEE KKM TRD
SEQ ID 20: (cont.)            GGNQ--NRFESLEE KKM TRD
SEQ ID 21: (cont.)            GGNQ--NRFESLEE KKM TRD
SEQ ID 22: (cont.)            GGNQ--NRFESLEE KKM TRD
BPTI(SEQ ID 29): (cont.)      RAKR--NNFKSAED MRT GGA
ITI-D1(SEQ ID 30): (cont.)    MGNG--NNFVTEKE LQT RTV
ITI-D2(SEQ ID 31): (cont.)    QGNG--NKFYSEKE REY GVP
LACI-D1(SEQ ID 32): (cont.)   EGNQ--NRFESLEE KKM TRD
LACI-D2(SEQ ID 33): (cont.)   LGNM--NNFETLEE KNI EDG
LACI-D3(SEQ ID 34): (cont.)   GGNE--NNFTSKQE LRA KKG
HKI B9(SEQ ID 35): (cont.)    GGNS--NNFLRKEK EKF KFT
C-3(SEQ ID 36): (cont.)       GGNE--NKFGSQKE EKV APV
TFPI-2 D1(SEQ ID 37): (cont.) EGNA--NNFYTWEA DDA WRI
TFPI-2 D2(SEQ ID 38): (cont.) HRNRIENRFPDEAT MGF APK
TFPI-2 D3(SEQ ID 39): (cont.) GGND--NNFVSRED KRA AKA
APP-I(SEQ ID 40): (cont.)     GGNR--NNFDTEEY MAV GSA
EpiNE7(SEQ ID 41): (cont.)    MGNG--NNFKSAED MRT GGA
BITI-E7-141(SEQ ID 42): (cont.) MGNG--NNFVTEKD LQT RGA
MUTT26A(SEQ ID 43): (cont.)   MGNG--NNFVTEKD LQT RGA
MUTQE(SEQ ID 44): (cont.)     MGNG--NNFVTEKD LQT RGA
MUT1619(SEQ ID 45): (cont.)   MGNG--NNFVTEKD LQT RGA
EPI-HNE-1(SEQ ID 46): (cont.) MGNG--NNFKSAED MRT GGA
EPI-HNE-2(SEQ ID 47): (cont.) QGNG--NKFYSEKE REY GVP
EPI-HNE-3(SEQ ID 48): (cont.) QGNG--NKFYSEKE REY GVP
EPI-HNE-4(SEQ ID 49): (cont.) QGNG--NKFYSEKE REY GVP
DPI14 KR(SEQ ID 50): (cont.)  GGNR--NNFDTEEY MAV GSA
DPI24 KR(SEQ ID 51): (cont.)  EGNA--NNFYTWEA DDA WRI
DPI68 KR(SEQ ID 52): (cont.)  LGNM--NNFETLEE KNI EDG
DPI84 KR(SEQ ID 53): (cont.)  GGNE--NKFGSQKE EKV APV
```

FIG. 3B

KALLIKREIN INHIBITORS AND ANTI-THROMBOLYTIC AGENTS AND USES THEREOF

CROSS-REFERENCE TO RELATED APPLICATIONS

This application is a divisional of U.S. patent application Ser. No. 13/458,086, filed Apr. 27, 2012, which is a continuation of U.S. patent application Ser. No. 11/804,388, filed May 18, 2007, now U.S. Pat. No. 8,188,045, which is a divisional application of U.S. patent application Ser. No. 11/125,639, filed May 9, 2005, now U.S. Pat. No. 7,235,530, which is a continuation-in-part of U.S. patent application Ser. No. 10/953,902, filed Sep. 27, 2004, now U.S. Pat. No. 7,153,829, the entire contents of which are incorporated herein by reference.

TECHNICAL FIELD

This invention is generally in the field of invasive surgical procedures associated with contact activation of complement components and the coagulation/fibrinolysis systems. More specifically, the invention provides methods, kits and compositions utilizing a combination of a non-naturally occurring kallikrein inhibitor and an anti-thrombolytic agent, e.g., an anti-fibrinolytic agent, to reduce or prevent blood loss, e.g., perioperative blood loss, and/or injury associated with various ischemias, e.g., in patients subjected to invasive surgical procedures. For example, the invention provides methods, kits and compositions for reducing blood loss associated with procedures requiring cardiopulmonary bypass.

BACKGROUND

Owing to the many advances in medicine a number of highly invasive surgical procedures are carried out each day that result in blood loss, or place patients at a high risk for blood loss. Such patients must be carefully monitored to restore and maintain normal blood supply and hemostasis, and they may need blood transfusions. Surgical procedures that involve blood loss include those involving extra-corporeal circulation methods such as cardiopulmonary bypass (CPB). In such methods, a patient's heart is stopped and the circulation, oxygenation, and maintenance of blood volume are carried out artificially using an extra-corporeal circuit and a synthetic membrane oxygenator. These techniques are commonly used during cardiac surgery. Additionally, it is apparent that surgery involving extensive trauma to bone, such as the sternal split necessary in coronary artery bypass grafting (CABG) or hip replacement procedures, is also associated with activation of the contact activation system (CAS), which can result in a variety of disruptions in the blood and vasculature.

Atherosclerotic coronary artery disease (CAD) causes a narrowing of the lumen of one or several of the coronary arteries; this limits the flow of blood to the myocardium (i.e., the heart muscle) and can cause angina, heart failure, and myocardial infarcts. In the end stage of coronary artery atherosclerosis, the coronary circulation can be almost completely occluded, causing life threatening angina or heart failure, with a very high mortality. CABG procedures may be required to bridge the occluded blood vessel and restore blood to the heart; these are potentially life saving. CABG procedures are among the most invasive of surgeries in which one or more healthy veins or arteries are implanted to provide a "bypass" around the occluded area of the diseased vessel.

The number of CABG procedures performed in the United States in 1998 was approximately 500,000. CABG procedures carry with them a small but important perioperative risk, but they are very successful in providing patients with immediate relief from the mortality and morbidity of atherosclerotic cardiovascular disease. Despite these very encouraging results, repeat CABG procedures are not uncommon, as indicated by a clear increase in the number of patients who eventually undergo second and even third procedures; the perioperative mortality and morbidity seen in primary CABG procedures is increased in these re-do procedures.

There have been improvements in minimally invasive surgical techniques for uncomplicated CAD. However, nearly all CABG procedures performed for valvular and/or congenital heart disease, heart transplantation, and major aortic procedures, are still carried out on patients supported by CPB. In CPB, large cannulae are inserted into the great vessels of a patient to permit mechanical pumping and oxygenation of the blood using a membrane oxygenator. The blood is returned to the patient without flowing through the lungs, which are hypoperfused during this procedure. The heart is stopped using a cardioplegic solution, the patient cooled to help prevent brain damage, and the peripheral circulating volume increased by an extracorporeal circuit, i.e., the CPB circuit, which requires "priming" with donor blood and saline mixtures are used to fill the extracorporeal circuit. CPB has been extensively used in a variety of procedures performed for nearly half a century with successful outcomes. The interaction between artificial surfaces, blood cells, blood proteins, damaged vascular endothelium, and extravascular tissues, such as bone, disturbs hemostasis and frequently activates the CAS, which, as noted above, can result in a variety of disruptions in the blood and vasculature. Such disruption leads to excess perioperative bleeding, which then requires immediate blood transfusion. A consequence of circulating whole blood through an extracorporeal circuit in CPB may also include the systemic inflammatory response (SIR), which is initiated by contact activation of the coagulation and complement systems. Indeed, much of the morbidity and mortality associated with seemingly mechanically successful CPB surgical procedures is the result of the effects of activating coagulation, fibrinolysis, or complement systems. Such activation may damage the pulmonary system, leading to adult respiratory distress syndrome (ARDS), impairment of kidney and splanchnic circulation, and induction of a general coagulopathy leading to blood loss and the need for transfusions. In addition to the dangers of perioperative blood loss, additional pathologies associated with SIR include neurocognitive deficits, stroke, renal failure, acute myocardial infarct, and cardiac tissue damage.

Blood transfusions also present a significant risk of infection and elevate the cost of CABG or other similar procedures that require CPB. In the absence of any pharmacological intervention, three to seven units of blood must typically be expended on a patient, even with excellent surgical techniques. Accordingly, there is considerable incentive for the development of new and improved treatments to reduce or prevent perioperative bleeding and SIR in patients subjected to CPB and CABG procedures.

SUMMARY

The disclosure is based, at least in part, on the discovery that a combination of a non-naturally occurring kallikrein inhibitor, e.g., a Kunitz domain kallikrein inhibitor polypeptide, and an anti-thrombolytic agent, e.g., an anti-fibrinolytic agent, can be administered to a subject to eliminate or reduce blood loss, e.g., perioperative blood loss, as well as injury associated with ischemia (including ischemia associated with perioperative blood loss and cerebral ischemia), the onset of systemic inflammatory response, and/or reperfusion injury, e.g., reperfusion injury associated with cerebral ischemia or a focal brain ischemia. In one embodiment, the treatment can reduce or eliminate blood loss by one or more of: reducing or eliminating bleeding, capillary leakage and alterations in body fluid balance. The treatment can be in patients subjected to invasive surgical procedures such as, e.g., cardiothoratic surgery (e.g., cardiopulmonary bypass), orthopedic surgery (e.g., hip or knee replacement or fracture), hepatectomy, nephrectomy. The invasive surgical procedure can involve the use of extracorporeal circulation or dialysis. Preferably, the treatment is more effective because of the combined administration. For example, the anti-thrombolytic agent is more effective, e.g., an equivalent effect is seen with less of the anti-thrombolytic agent, the anti-thrombolytic treatment reduces symptoms to a greater extent than would be seen if the anti-thrombolytic treatment were administered in the absence of the non-naturally occurring kallikrein inhibitor, and/or an unwanted side effect associated with the anti-thrombolytic agent is seen less than would be seen if the anti-thrombolytic agent was administered in the absence of the non-naturally occurring kallikrein inhibitor, or the analogous situation is seen with the non-naturally occurring kallikrein inhibitor.

Accordingly, the disclosure features methods, compositions and kits that include a non-naturally occurring kallikrein inhibitor, e.g., a plasma kallikrein inhibitor, and an anti-thrombolytic agent, to eliminate or reduce blood loss and/or injury associated with ischemias. Preferably, the anti-thrombolytic agent is an anti-fibrinolytic agent, e.g., an anti-fibrinolytic agent described herein. Anti-fibrinolytic agents can be one or more of: tranexamic acid (Cyklokapron™), epsilon amino caproic acid (Amicar™), aprotinin (Trasyol™), Desmopressin (DDAVP), and pirfenidone.

In one aspect, the disclosure features a method for preventing or reducing blood loss in a patient that includes administering to the patient a non-naturally occurring inhibitor of kallikrein, e.g., a plasma kallikrein, in combination with an anti-thrombolytic agent, e.g., an anti-fibrinolytic agent. Typically, the patient is a human patient. The combination of the inhibitor of kallikrein and the anti-thrombolytic agent can be administered in an amount effective to prevent or reduce blood loss (e.g., prevent or reduce one or more of: bleeding, capillary leakage and alterations in body fluid balance). In a particular embodiment, the blood loss is perioperative blood loss is due to a surgical procedure performed on the patient. The surgical procedure can be, e.g., a cardiothoracic surgery, (e.g., cardiopulmonary bypass or coronary artery bypass grafting); orthopedic surgery (e.g., hip or knee replacement or bone fracture); hepatectomy; nephrectomy; procedures that utilize extracorporeal circulation or dialysis; and any other procedure which can result in perioperative blood loss. The inhibitor and/or the anti-thrombolytic agent can be administered before, during, or after the procedure. In one embodiment, the method reduces the amount or need for a transfusion before, during or after the procedure.

In another aspect, the disclosure features a kit for preventing or reducing blood loss, e.g., perioperative blood loss due to a surgical procedure performed on the patient. The kit can include a non-naturally occurring inhibitor of kallikrein, e.g., plasma kallikrein, and instructions for administering the inhibitor in combination with an anti-thrombolytic agent, e.g., an anti-fibrinolytic agent. In one embodiment, the instructions provide a dosing regimen, dosing schedule, and/or route of administration of the inhibitor that differs from the dosing regimen, dosing schedule and/or route of administration for the inhibitor in the absence of the anti-thrombolytic agent. In one embodiment, the kit further includes an anti-thrombolytic agent, e.g., an anti-fibrinolytic agent.

In another aspect, the disclosure features a method for preventing or reducing injury associated with ischemia in a patient that includes administering to the patient a non-naturally occurring inhibitor of kallikrein, e.g., a plasma kallikrein, in combination with an anti-thrombolytic agent, e.g., an anti-fibrinolytic agent. Typically, the patient is a human patient. The combination of the inhibitor of kallikrein and the anti-thrombolytic agent can be administered in an amount effective to prevent or reduce an injury associated with ischemia in the patient. In a particular embodiment, the ischemia is at least partially due to blood loss, e.g., perioperative blood loss due to a surgical procedure performed on the patient. The surgical procedure can be, e.g., a cardiothoracic surgery, (e.g., cardiopulmonary bypass or coronary artery bypass grafting); orthopedic surgery (e.g., hip or knee replacement or bone fracture); hepatectomy; nephrectomy; procedures that utilize extracorporeal circulation or dialysis; and any other procedure which can result in perioperative blood loss. The inhibitor and/or the anti-thrombolytic agent can be administered before, during, or after the procedure.

In another aspect, the disclosure features a kit for preventing or reducing injury associated with ischemia in a patient, e.g., ischemia at least partially due to blood loss, e.g., perioperative blood loss due to a surgical procedure performed on the patient. The kit can include a non-naturally occurring inhibitor of kallikrein, e.g., plasma kallikrein, and instructions for administering the inhibitor in combination with an anti-thrombolytic agent, e.g., an anti-fibrinolytic agent. In one embodiment, the instructions provide a dosing regimen, dosing schedule, and/or route of administration of the inhibitor that differs from the dosing regimen, dosing schedule and/or route of administration for the inhibitor in the absence of the anti-thrombolytic agent. In one embodiment, the kit further includes an anti-thrombolytic agent, e.g., an anti-fibrinolytic agent.

In another aspect, the disclosure features a method for preventing or reducing a systemic inflammatory response, e.g., a response associated with a surgical procedure in a patient or its onset. The method includes: administering to the patient a non-naturally occurring inhibitor of kallikrein, e.g., plasma kallikrein, in combination with an anti-thrombolytic agent, e.g., an anti-fibrinolytic agent. Typically, the patient is a human patient. The inhibitor and/or the anti-thrombolytic agent can be administered before, during, or after surgery. In one embodiment, the surgical procedure is a cardiothoracic surgery, (e.g., cardiopulmonary bypass or coronary artery bypass grafting); orthopedic surgery (e.g., hip or knee replacement or bone fracture); hepatectomy; nephrectomy; a procedure that utilize extracorporeal circulation or dialysis; and any other procedure which can result in perioperative blood loss.

In another aspect, the disclosure features a kit for preventing or reducing systemic inflammatory response, e.g., a response associated with a surgical procedure in a patient or its onset. The kit can include a non-naturally occurring inhibitor of kallikrein, e.g., plasma kallikrein, and instructions for administering the inhibitor in combination with an anti-thrombolytic agent, e.g., an anti-fibrinolytic agent. In one embodiment, the instructions provide a dosing regimen, dosing schedule, and/or route of administration of the inhibitor that differs from the dosing regimen, dosing schedule and/or route of administration for the inhibitor in the absence of the anti-thrombolytic agent. In one embodiment, the kit further includes an anti-thrombolytic agent, e.g., an anti-fibrinolytic agent.

In another aspect, the disclosure features a method for treating a brain or central nervous system (CNS) injury. The method can be used to prevent or reduce adverse effects of cerebral ischemia, e.g., stroke, and/or reperfusion injury, e.g., reperfusion injury associated with cerebral ischemia, in a patient including administering to the patient a non-naturally occurring inhibitor of kallikrein, e.g., a plasma kallikrein, in combination with an anti-thrombolytic agent, e.g., an anti-fibrinolytic agent. In one embodiment, the cerebral ischemia is stroke, e.g., embolism-, thrombus- or hemorrhage-associated stroke. The method can include administering the inhibitor and/or the anti-thrombolytic agent, before, during, or after the ischemia, e.g., at the time of reperfusion or at a time between 1-12 hours after an ischemic event, e.g., between 1-5 hours after such an event.

In another aspect, the disclosure features a kit for treating a brain or central nervous system (CNS) injury, e.g., to prevent or reduce adverse effects of cerebral ischemia, e.g., stroke, and/or reperfusion injury, e.g., reperfusion injury associated with cerebral ischemia. In one embodiment, the cerebral ischemia is stroke, e.g., embolism-, thrombus- or hemorrhage-associated stroke. The kit can include a non-naturally occurring inhibitor of kallikrein, e.g., plasma kallikrein, and instructions for administering the inhibitor in combination with an anti-thrombolytic agent, e.g., an anti-fibrinolytic agent. In one embodiment, the instructions provide a dosing regimen, dosing schedule, and/or route of administration of the inhibitor that differs from the dosing regimen, dosing schedule and/or route of administration for the inhibitor in the absence of the anti-thrombolytic agent. In one embodiment, the kit further includes an anti-thrombolytic agent, e.g., an anti-fibrinolytic agent.

The disclosure also features a composition that includes a non-naturally occurring inhibitor of kallikrein, e.g., a plasma kallikrein, and an anti-thrombolytic agent, e.g., an anti-fibrinolytic agent. The composition can further include a pharmaceutically acceptable carrier, stabilizer and/or excipient.

The non-naturally occurring kallikrein inhibitor used in any disclosed method, kit or composition can have one or more of the characteristics described below.

The kallikrein inhibitor can have a Ki for kallikrein, e.g., plasma kallikrein, of less than 50 nM, 40 nM, 30 nM, 20 nM, 5 nM, 1 nM, 500 pM, 100 pM, 50 pM, e.g., about 44 pM. The kallikrein inhibitor can preferentially inhibit plasma kallikrein at least 100, 200, 500, or 1000 more than another kallikrein, e.g., human urine kallikrein, or another protease, e.g., plasmin or thrombin.

In one embodiment, the kallikrein inhibitor is an agent that can cross the blood-brain barrier.

In one embodiment, the kallikrein inhibitor includes a polypeptide that includes a Kunitz domain such as the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO:1).

The framework of the Kunitz domain can be human or can differ from a human Kunitz domain framework by fewer than six, five, four, three, or two amino acids. For example, the framework of the Kunitz domain can be the framework of one of the Kunitz domains of human lipoprotein-associated coagulation inhibitor (LACI) protein, e.g., the first second or third Kunitz domain. LACI is also known as "Tissue Factor Pathway Inhibitor" or "TFPI". Typically, the polypeptide differs from BPTI and/or one or more of the LACI Kunitz domains by at least one, two, three, or four amino acids, e.g., at least one, two or three amino acids in the binding loops and/or at least two, three, four, or six amino acids in the framework region. For example, the polypeptide can include a non-naturally occurring Kunitz domain that is derived from a naturally occurring Kunitz domain, e.g., a human Kunitz domain. In one embodiment, an inhibitor that includes a Kunitz domain binds to plasma kallikrein with an affinity that is at least 10, 100, or 500 fold better than BPTI and/or LACI.

In one embodiment, the polypeptide that inhibits kallikrein is not immunogenic on second use.

In one embodiment, the polypeptide that inhibits kallikrein can have one or more of the following features: Xaa1, Xaa2, Xaa3, Xaa4, Xaa56, Xaa57 or Xaa58 are each individually an amino acid or absent; Xaa10 is an amino acid selected from the group consisting of: Asp and Glu; Xaa11 is an amino acid selected from the group consisting of: Asp, Gly, Ser, Val, Asn, Ile, Ala and Thr; Xaa13 is an amino acid selected from the group consisting of: Arg, His, Pro, Asn, Ser, Thr, Ala, Gly, Lys and Gln; Xaa15 is an amino acid selected from the group consisting of: Arg, Lys, Ala, Ser, Gly, Met, Asn and Gln; Xaa16 is an amino acid selected from the group consisting of: Ala, Gly, Ser, Asp and Asn; Xaa17 is an amino acid selected from the group consisting of: Ala, Asn, Ser, Ile, Gly, Val, Gln and Thr; Xaa18 is an amino acid selected from the group consisting of: His, Leu, Gln and Ala; Xaa19 is an amino acid selected from the group consisting of: Pro, Gln, Leu, Asn and Ile; Xaa21 is an amino acid selected from the group consisting of: Trp, Phe, Tyr, His and Ile; Xaa22 is an amino acid selected from the group consisting of: Tyr and Phe; Xaa23 is an amino acid selected from the group consisting of: Tyr and Phe; Xaa31 is an amino acid selected from the group consisting of: Glu, Asp, Gln, Asn, Ser, Ala, Val, Leu, Ile and Thr; Xaa32 is an amino acid selected from the group consisting of: Glu, Gln, Asp Asn, Pro, Thr, Leu, Ser, Ala, Gly and Val; Xaa34 is an amino acid selected from the group consisting of: Thr, Ile, Ser, Val, Ala, Asn, Gly and Leu; Xaa35 is an amino acid selected from the group consisting of: Tyr, Trp and Phe; Xaa39 is an amino acid selected from the group consisting of: Glu, Gly, Ala, Ser and Asp; Xaa40 is an amino acid selected from the group consisting of: Gly and Ala; Xaa43 is an amino acid selected from the group consisting of: Asn and Gly; Xaa45 is an amino acid selected from the group consisting of: Phe and Tyr; and wherein the polypeptide inhibits kallikrein.

In a particular embodiment, individual amino acid positions of a kallikrein inhibitor that includes the amino acid sequence of SEQ ID NO:1 has one or more of the following: Xaa10 is Asp, Xaa11 is Asp, Xaa13 is Pro, Xaa15 is Arg, Xaa16 is Ala, Xaa17 is Ala, Xaa18 is His, Xaa19 is Pro, Xaa21 is Trp, Xaa31 is Glu, Xaa32 is Glu, Xaa34 is Ile, Xaa35 is Tyr, Xaa39 is Glu.

The polypeptide that inhibits kallikrein can include (or consist of) the following amino acid sequence: Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2), or a fragment thereof, e.g., a fragment that binds and inhibits kallikrein. For example, the polypeptide can have fewer than 80, 70, 65, 60, 58, 55 or 52 amino acids.

The polypeptide that inhibits kallikrein can include (or consist of) a polypeptide described in U.S. Pat. No. 5,786,328, the contents of which are incorporated by reference.

Methods, kits and compositions described herein can include an inhibitor that comprises a non-naturally occurring, Kunitz domain polypeptide having any of the amino acid sequences described herein and an additional flanking sequence of one to six amino acids at the amino and/or carboxy terminal end domains. Such additional amino acids may be artifacts of expressing a particular non-naturally occurring kallikrein inhibitor polypeptide or Kunitz domain polypeptide in any of a variety of recombinant expression vector systems, such as used in yeast, bacteria, mammalian cell lines, insect cells, and the like. Preferably, such additional amino acids at the amino and/or carboxy termini of a non-naturally occurring Kunitz domain described herein do not diminish the affinity for kallikrein or kallikrein inhibition activity of the domain or a polypeptide comprising the domain.

The inhibitor polypeptide can include a non-naturally occurring Kunitz domain polypeptide having an amino acid sequence of SEQ ID NO:1 and an amino terminal flanking sequence as the result of producing the polypeptide as a recombinant protein in yeast. An example of a particularly preferred yeast recombinant expression system comprises fusing a nucleotide coding sequence for a non-naturally occurring Kunitz domain of SEQ ID NO:1 to a nucleotide sequence encoding the matα Prepro peptide leader sequence of *Saccharomyces cerevisiae* and expressing the recombinant coding sequence in the yeast *Pichia pastoris*. The resulting expressed fusion protein comprises an amino acid sequence of SEQ ID NO:1 and an amino terminal flanking dipeptide, Glu-Ala. A particularly preferred species of an inhibitor polypeptide of the invention produced in a yeast expression system has the amino acid sequence of SEQ ID NO:2:

inhibit kallikrein. For example, the mixture can include one or more modified polypeptides that inhibit kallikrein and that include a polymer moiety such as a polyethylene glycol moiety and one or more unmodified polypeptides that inhibit kallikrein and do not include a polymer moiety. In one embodiment, approximately 10%, 20%, 30%, 40%, 50%, 60%, 70%, 80%, 90% or all of the polypeptides that inhibit kallikrein in the mixture are modified.

The kallikrein inhibitor polypeptides useful in the methods, compositions and kits may be any of the non-naturally occurring Kunitz domain polypeptides described herein or larger polypeptides comprising any such Kunitz domains, provided the kallikrein inhibitor polypeptides bind and inhibit kallikrein as determined in standard assays.

The anti-thrombolytic agent used in any disclosed method, kit or composition can be an anti-fibrinolytic agent. Examples of anti-fibrinolytic agents include: tranexamic acid (Cyklokapron™), epsilon amino caproic acid (Amicar™), aprotinin (Trasyol™), Desmopressin (DDAVP), pirfenidone, and combinations thereof. In one embodiment, the anti-thrombolytic agent is an anti-fibrinolytic agent selected from epsilon amino caproic acid (Amicar™), aprotinin (Trasyol™), and combinations thereof.

The methods described herein can include administering an effective amount of the combination treatment. Such an amount can be an amount sufficient to produce an improvement detectable to one skilled in the art, to ameliorate at least one symptom, or to modulate (e.g., improve) at least one physiological parameter, e.g., to a statistically significant degree.

Preferred compositions, e.g., used in any method or kit described herein, may further comprise one or more pharmaceutically acceptable buffers, carriers, and excipients, which may provide a desirable feature to the composition including, but not limited to, enhanced administration of the composition to a patient, enhanced circulating half-life of the inhibitor and/or anti-thrombolytic agent, enhanced compatibility of the composition with patient blood chemistry, enhanced storage of the composition, and/or enhanced efficacy of the composition upon administration to a patient.

Preferred methods described herein are useful for preventing or reducing perioperative blood loss and/or SIR in a patient subjected to a surgical procedure such as a surgical procedure that requires extra-corporeal circulation (e.g., (SEQ ID NO: 2)
Glu Ala Met His Ser Phe Cys Ala Phe Lys Ala Asp Asp Gly Pro Cys Arg Ala Ala His Pro Arg Trp Phe Phe Asn Be Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp.

In one embodiment, the polypeptide that inhibits kallikrein is modified, e.g., to include one or more moieties, e.g., one or more moieties that extend half life of the polypeptide, e.g., a polymer moiety or a plurality of polymer moieties, e.g., as described in U.S. Ser. No. 10/931,153, filed Aug. 30, 2004. For example, the polypeptide can include a plurality of polyethylene glycol moieties, e.g., one on an N-terminal amine and one attached to each lysine of the polypeptide. The polyethylene glycol moieties can be less than 10, 8, 7, or 6 kDa in average molecular weight. In other embodiments, the moiety can be, e.g., serum albumin, e.g., human serum albumin. Other exemplary modifications include a label, e.g., a radioactive or MRI-detectable label. In some embodiments, the polypeptide is part of a mixture that includes modified and unmodified polypeptides that cardiopulmonary bypass (CPB)) or dialysis. Particularly preferred are methods of the invention for preventing or reducing perioperative blood loss and/or SIR in a patient subjected to a surgical procedure comprising administering to the patient of a kallikrein inhibitor polypeptide described herein, in combination with an anti-thrombolytic agent, e.g., an anti-fibrinolytic agent, wherein the surgical procedure requires cardiopulmonary bypass (CPB) and the surgical procedure is a coronary artery bypass graft (CABG) procedure.

Methods described herein may be carried out on a patient before, during, and/or after the surgical procedure. Particularly preferred is the use of the methods before and during a surgical procedure, especially in the case of CABG procedures to prevent perioperative blood loss by activation of the contact activation system and the onset of SIR.

In another embodiment, the invention provides nucleic acid molecules comprising nucleotide sequences coding for a non-naturally occurring Kunitz domain or kallikrein inhibitor polypeptide described herein. Such nucleic acid molecules may be any of a variety of nucleic acid molecules including, but not limited to, a recombinant phage genome, a recombinant mammalian viral vector, a recombinant insect viral vector, a yeast mini chromosome, and a plasmid. Preferred plasmid molecules of the invention include but are not limited to yeast expression plasmids, bacterial expression plasmids, and mammalian expression plasmids. Nucleic acid molecules useful in the invention may comprise a specific nucleotide sequence described herein or a degenerate form thereof.

Particularly preferred nucleic acid molecules of the invention include a nucleic acid molecule comprising a nucleotide sequence as shown in FIG. 2 encoding a fusion protein comprising a matα Prepro signal peptide fused to a heretofore undisclosed kallikrein inhibitor polypeptide, nucleic acid molecules comprising the nucleotide sequence encoding the kallikrein inhibitor polypeptide having an amino acid of SEQ ID NO:2, and nucleic acid molecules comprising a nucleotide sequence encoding a kallikrein inhibitor polypeptide having an amino acid sequence of amino acids 3-60 of SEQ ID NO:2.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 2 shows a portion of a DNA and corresponding deduced amino acid for an exemplary kallikrein inhibitor polypeptide in plasmid pPIC-K503. The inserted DNA encodes the matα Prepro signal peptide of *Saccharomyces cerevisiae* (underlined) fused in frame to the amino terminus of the PEP-1 polypeptide having the amino acid sequence enclosed by the boxed area. The amino acid sequence of the PEP-1 polypeptide shown in the boxed region is SEQ ID NO:2, and the corresponding nucleotide coding sequence is SEQ ID NO:3. The dashed arrows indicate the location and direction of two PCR primer sequences in AOX regions that were used to produce sequencing templates. DNA sequence for the entire nucleotide sequence of the figure includes the structural coding sequence for the fusion protein and is designated SEQ ID NO:27. The double underlined portion of the sequence indicates a diagnostic probe sequence. BstB I and EcoR I indicate locations of their respective palindromic, hexameric, restriction endonuclease sites in the sequence. Asterisks denote translational stop codons. See text for details.

FIGS. 3A and 3B show an alignment of exemplary amino acid sequences, the native LACI sequence from which these variants were derived (SEQ ID NO:32), and other known Kunitz domains (SEQ ID NOS:29-31 and 33-53). Cysteine residues are highlighted.

DETAILED DESCRIPTION

Figure 1:
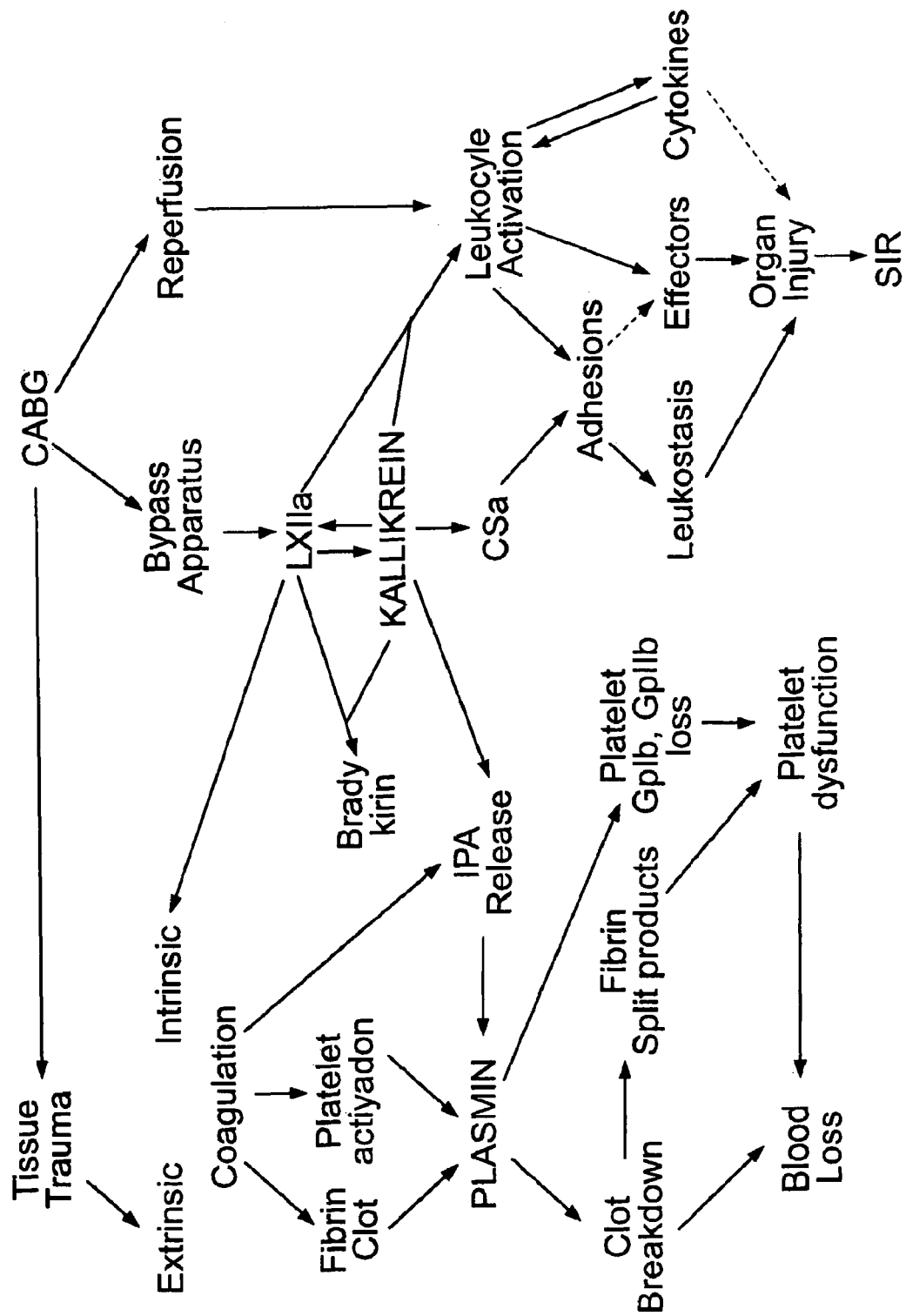
FIG. 1 is a simplified diagram of major multiple pathways and related events involved in the contact activation system and systemic inflammatory response (SIR) that may arise in a patient subjected to soft and bone tissue trauma such as that associated with a coronary artery bypass grafting (CABG) procedure, especially when the CABG procedure involves extra-corporeal blood circulation, such as cardiopulmonary bypass (Bypass Apparatus). Arrows indicate activation from one component or event to another component or event in the cascade. Arrows in both directions indicate activating effects of components or events in both directions. Broken arrows indicate likely participation of one component or event in the activation of another component or event. Abbreviations: "tPA", tissue plasminogen activator; "C5a", a protein component of the complement system; "fXIIa", activator protein of prekallikrein to form active kallikrein; "Extrinsic", extrinsic coagulation system; "Intrinsic", intrinsic coagulation system.

The invention is based on the discovery that the use of a group of kallikrein inhibitor (KI) polypeptides that bind to and inhibit plasma kallikrein with a specificity, in combination with an anti-thrombolytic agent, e.g., an anti-fibrinolytic agent, provides improved methods of preventing or reducing blood loss, e.g., perioperative blood loss, e.g., in patients undergoing surgical procedures. The methods can also reduce or prevent injury associated with various ischemias and/or a systemic inflammatory response (SIR) in patients undergoing surgical procedures. Surgical procedures can include, e.g., a cardiothoracic surgery, (e.g., cardiopulmonary bypass (CPB) or coronary artery bypass grafting (CABG)); orthopedic surgery (e.g., hip or knee replacement or bone fracture); hepatectomy; nephrectomy; procedures that utilize extracorporeal circulation or dialysis; and any other procedure which can result in perioperative blood loss. "Blood loss" as used herein refers restoring blood supply and/or hemostasis, maintaining blood supply and/or hemostasis, and/or reducing the amount or need for a transfusion. For example, the methods, kits and compositions described herein can be used to reduce or prevent bleeding, capillary leakage and/or alterations in body fluid balance. Administered "in combination", as used herein, means that two (or more) different treatments are delivered to the subject while the subject is at risk for blood loss or during the course of the blood loss, e.g., the two or more treatments are delivered after the subject has been determined to be at risk for the disorder and before the disorder has been prevented, cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the anti-thrombolytic agent is more effective, e.g., an equivalent effect is seen with less of the anti-thrombolytic agent, the anti-thrombolytic agent reduces symptoms to a greater extent than would be seen if the anti-thrombolytic agent were administered in the absence of the kallikrein inhibitor, and/or a side effect associated with the anti-thrombolytic agent is seen to a lesser extent than if the anti-thrombolytic agent were administered in the absence of the kallikrein inhibitor, or the analogous situation is seen with the kallikrein inhibitor. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The combination treatment can be used to prevent or treat disorders associated with blood loss or blood fluidity. For example, the combination of a kallikrein inhibitor and an anti-thrombolytic agent can be used to treat or prevent perioperative blood loss, a systemic inflammatory response (SIR) induced by kallikrein (especially, for example, in patients undergoing surgical procedures and particularly surgical procedures involving cardiothoracic surgery, e.g., cardiopulmonary bypass (CPB), such as a coronary artery bypass graft (CABG) procedures as well as in patients with other disorders), cerebral ischemia and/or reperfusion injury associated with ischemia, e.g., cerebral ischemia.

Further examples of applications of the combination treatment include pediatric cardiac surgery, lung transplantation, total hip replacement and orthotopic liver transplantation, and to reduce or prevent perioperative stroke during CABG, extracorporeal membrane oxygenation (ECMO) and cerebrovascular accidents (CVA) during these procedures. The combination treatment can also be used for stroke, e.g., embolism, thrombus and/or hemorrhage associated stroke and for reperfusion injury associated with stroke.

Cardiothoracic surgery is surgery of the chest area, most commonly the heart and lungs. Typical diseases treated by cardiothoracic surgery include coronary artery disease, tumors and cancers of the lung, esophagus and chest wall, heart vessel and valve abnormalities, and birth defects involving the chest or heart. Where cardiothoracic surgery is utilized for treatment, the risk of blood loss (and, e.g., surgery-induced ischemia) and the onset of a systemic inflammatory response (SIR) is incurred. Surgery-induced SIR can result in severe organ dysfunction (systemic inflammatory response syndrome; SIRS).

Kunitz Domains

A number of useful inhibitors of kallikrein include a Kunitz domain.

As used herein, a "Kunitz domain" is a polypeptide domain having at least 51 amino acids and containing at least two, and preferably three, disulfides. The domain is folded such that the first and sixth cysteines, the second and fourth, and the third and fifth cysteines form disulfide bonds (e.g., in a Kunitz domain having 58 amino acids, cysteines can be present at positions corresponding to amino acids 5, 14, 30, 38, 51, and 55, according to the number of the BPTI homologous sequences provided below, and disulfides can form between the cysteines at position 5 and 55, 14 and 38, and 30 and 51), or, if two disulfides are present, they can form between a corresponding subset of cysteines thereof. The spacing between respective cysteines can be within 7, 5, 4, 3, 2, 1 or 0 amino acids of the following spacing between positions corresponding to: 5 to 55, 14 to 38, and 30 to 51, according to the numbering of the BPTI sequence provided below. The BPTI sequence can be used as a reference to refer to specific positions in any generic Kunitz domain. Comparison of a Kunitz domain of interest to BPTI can be performed by identifying the best fit alignment in which the number of aligned cysteines in maximized.

The 3D structure (at high resolution) of the Kunitz domain of BPTI is known. One of the X-ray structures is deposited in the Brookhaven Protein Data Bank as "6PTI". The 3D structure of some BPTI homologues (Eigenbrot et al., (1990) Protein Engineering, 3(7):591-598; Hynes et al., (1990) Biochemistry, 29:10018-10022) are known. At least eighty one Kunitz domain sequences are known. Known human homologues include three Kunitz domains of LACI (Wun et al., (1988) J. Biol. Chem. 263(13):6001-6004; Girard et al., (1989) Nature, 338:518-20; Novotny et al, (1989) J. Biol. Chem., 264(31):18832-18837) two Kunitz domains of Inter-α-Trypsin Inhibitor, APP-I (Kido et al., (1988) J. Biol. Chem., 263(34):18104-18107), a Kunitz domain from collagen, three Kunitz domains of TFPI-2 (Sprecher et al., (1994) PNAS USA, 91:3353-3357), the Kunitz domains of hepatocyte growth factor activator inhibitor type 1, the Kunitz domains of Hepatocyte growth factor activator inhibitor type 2, the Kunitz domains described in U.S. Patent Publication No.: 20040152633. LACI is a human serum phosphoglycoprotein with a molecular weight of 39 kDa (amino acid sequence in Table 1) containing three Kunitz domains.

TABLE 1

Exemplary Natural Kunitz Domains

```
LACI:          1 MIYTMKKVHA LWASVCLLLN LAPAPLNAds eedeehtiit dtelpplklM
(SEQ ID       51 HSFCAFKADD GPCKAIMKRF FFNIFTRQCE EFIYGGCEGN QNRFESLEEC
NO. 54)      101 KKMCTRDnan riikttlqqe kpdfCfleed pqiCrqyitr yfynnqtkqC
             151 erfkyggClg nmnnfetlee CkniCedgpn gfqvdnygtq lnavnnsltp
             201 qstkvpslfe fhgpswCltp adrglCrane nrfyynsvig kCrpfkysgC
             251 ggnennftsk geClraCkkg fiqriskggl iktkrkrkkq rvkiayeeif
             301 vknm
             The signal sequence (1-28) is uppercase and underscored
             LACI-K1 (50-107) is uppercase
             LACI-K2 (121-178) is underscored
             LACI-K3 (211-270) is bold BPTI             1         2          3          4          5
(SEQ ID      12345678901234567890123456789012345678901234567890123456789012345678
NO: 55)      RPDFCLEPPYTGPCKARIIRYFYNAKAGLCQTFVYGGCRAKRNNFKSAEDCMRTCGGA
```

The Kunitz domains above are referred to as LACI-K1 (residues 50 to 107), LACI-K2 (residues 121 to 178), and LACI-K3 (213 to 270). The cDNA sequence of LACI is reported in Wun et al. (J. Biol. Chem., 1988, 263(13):6001-6004). Girard et al. (Nature, 1989, 338:518-20) reports mutational studies in which the P1 residues of each of the three Kunitz domains were altered. LACI-K1 inhibits Factor VIIa (F.VIIa) when F.VIIa is complexed to tissue factor and LACI-K2 inhibits Factor Xa.

Proteins containing exemplary Kunitz domains include the following, with SWISS-PROT Accession Numbers in parentheses:

A4_HUMAN (P05067), A4_MACFA (P53601), A4_MACMU (P29216),
A4_MOUSE (P12023), A4_RAT (P08592), A4_SAISC (Q95241),
AMBP_PLEPL (P36992), APP2_HUMAN (Q06481), APP2_RAT (P15943),
AXP1_ANTAF (P81547), AXP2_ANTAF (P81548), BPT1_BOVIN (P00974),
BPT2_BOVIN (P04815), CA17_HUMAN (Q02388), CA36_CHICK (P15989),
CA36_HUMAN (P12111), CRPT_BOOMI (P81162), ELAC_MACEU (O62845),
ELAC_TRIVU (Q29143), EPPI_HUMAN (O95925), EPPI_MOUSE (Q9DA01),
HTIB_MANSE (P26227), IBP_CARCR (P00993), IBPC_BOVIN (P00976),
IBPI_TACTR (P16044), IBPS_BOVIN (P00975), ICS3_BOMMO (P07481),
IMAP_DROFU (P11424), IP52_ANESU (P10280), ISC1_BOMMO (P10831),
ISC2_BOMMO (P10832), ISH1_STOHE (P31713), ISH2_STOHE (P81129),
ISIK_HELPO (P00994), ISP2_GALME (P81906), IVB1_BUNFA (P25660),
IVB1_BUNMU (P00987), IVB1_VIPAA (P00991), IVB2_BUNMU (P00989),
IVB2_DABRU (P00990), IVB2_HEMHA (P00985), IVB2_NAJNI (P00986),
IVB3_VIPAA (P00992), IVBB_DENPO (P00983), IVBC_NAJNA (P19859),
IVBC_OPHHA (P82966), IVBE_DENPO (P00984), IVBI_DENAN (P00980),
IVBI_DENPO (P00979), IVBK_DENAN (P00982), IVBK_DENPO (P00981),
IVBT_ERIMA (P24541), IVBT_NAJNA (P20229), MCPI_MELCP (P82968),
SBPI_SARBU (P26228), SPT3_HUMAN (P49223), TKD1_BOVIN (Q28201),
TKD1_SHEEP (Q29428), TXCA_DENAN (P81658), UPTI_PIG (Q29100),
AMBP_BOVIN (P00978), AMBP_HUMAN (P02760), AMBP_MERUN (Q62577),
AMBP_MESAU (Q60559), AMBP_MOUSE (Q07456), AMBP_PIG (P04366),
AMBP_RAT (Q64240), IATR_HORSE (P04365), IATR_SHEEP (P13371),
SPT1_HUMAN (O43278), SPT1_MOUSE (Q9R097), SPT2_HUMAN (O43291),
SPT2_MOUSE (Q9WU03), TFP2_HUMAN (P48307), TFP2_MOUSE (O35536),
TFPI_HUMAN (P10646), TFPI_MACMU (Q28864), TFPI_MOUSE (O54819),
TFPI_RABIT (P19761), TFPI_RAT (Q02445), YN81_CAEEL (Q03610)

A variety of methods can be used to identify a Kunitz domain from a sequence database. For example, a known amino acid sequence of a Kunitz domain, a consensus sequence, or a motif (e.g., the ProSite Motif) can be searched against the GenBank sequence databases (National Center for Biotechnology Information, National Institutes of Health, Bethesda Md.), e.g., using BLAST; against Pfam database of HMMs (Hidden Markov Models) (e.g., using default parameters for Pfam searching; against the SMART database; or against the Propom database. For example, the Pfam Accession Number PF00014 of Pfam Release 9 provides numerous Kunitz domains and an HMM for identify Kunitz domains. A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314. The SMART database (Simple Modular Architecture Research Tool, EMBL, Heidelberg, Del.) of HMMs as described in Schultz et al. (1998), *Proc. Natl. Acad. Sci. USA* 95:5857 and Schultz et al. (2000) *Nucl. Acids Res* 28:231. The SMART database contains domains identified by profiling with the hidden Markov models of the HMMer2 search program (R. Durbin et al. (1998) *Biological sequence analysis: probabilistic models of proteins and nucleic acids.* Cambridge University Press). The database also is annotated and monitored. The Propom protein domain database consists of an automatic compilation of homologous domains (Corpet et al. (1999), *Nucl. Acids Res.* 27:263-267). Current versions of Propom are built using recursive PSI-BLAST searches (Altschul et al. (1997) *Nucleic Acids Res.* 25:3389-3402; Gouzy et al. (1999) *Computers and Chemistry* 23:333-340.) of the SWISS-PROT 38 and TREMBL protein databases. The database automatically generates a consensus sequence for each domain. Prosite lists the Kunitz domain as a motif and identifies proteins that include a Kunitz domain. See, e.g., Falquet et al. Nucleic Acids Res. 30:235-238 (2002).

Kunitz domains interact with target protease using, primarily, amino acids in two loop regions ("binding loops"). The first loop region is between about residues corresponding to amino acids 13-20 of BPTI. The second loop region is between about residues corresponding to amino acids 31-39 of BPTI. An exemplary library of Kunitz domains varies one or more amino acid positions in the first and/or second loop regions. Particularly useful positions to vary, when screening for Kunitz domains that interact with kallikrein or when selecting for improved affinity variants, include: positions 13, 15, 16, 17, 18, 19, 31, 32, 34, and 39 with respect to the sequence of BPTI. At least some of these positions are expected to be in close contact with the target protease. It is also useful to vary other positions, e.g., positions that are adjacent to the aforementioned positions in the three-dimensional structure.

The "framework region" of a Kunitz domain is defined as those residues that are a part of the Kunitz domain, but specifically excluding residues in the first and second binding loops regions, i.e., about residues corresponding to amino acids 13-20 of BPTI and 31-39 of BPTI. Conversely, residues that are not in the binding loop may tolerate a wider range of amino acid substitution (e.g., conservative and/or non-conservative substitutions).

In one embodiment, these Kunitz domains are variant forms of the looped structure including Kunitz domain 1 of human lipoprotein-associated coagulation inhibitor (LACI) protein. LACI contains three internal, well-defined, peptide loop structures that are paradigm Kunitz domains (Girard, T. et al., 1989. Nature, 338:518-520). Variants of Kunitz domain 1 of LACI described herein have been screened, isolated and bind kallikrein with enhanced affinity and specificity (see, for example, U.S. Pat. Nos. 5,795,865 and 6,057,287, incorporated herein by reference). These methods can also be applied to other Kunitz domain frameworks to obtain other Kunitz domains that interact with kallikrein, e.g., plasma kallikrein. Useful modulators of kallikrein function typically bind and/or inhibit kallikrein, as determined using kallikrein binding and inhibition assays.

An exemplary polypeptide that includes a Kunitz domain that inhibits kallikrein has the amino acid sequence defined by amino acids 3-60 of SEQ ID NO:2.

An exemplary polypeptide includes the amino acid sequence:

```
                                                           (SEQ ID NO: 1)
    Xaa1 Xaa2 Xaa3 Xaa4 Cys Xaa6 Xaa7 Xaa8 Xaa9 Xaa10 Xaa11 Gly Xaa13 Cys

Xaa15 Xaa16 Xaa17 Xaa18 Xaa19 Xaa20 Xaa21 Xaa22 Xaa23 Xaa24 Xaa25 Xaa26

Xaa27 Xaa28 Xaa29 Cys Xaa31 Xaa32 Phe Xaa34 Xaa35 Gly Gly Cys Xaa39 Xaa40

Xaa41 Xaa42 Xaa43 Xaa44 Xaa45 Xaa46 Xaa47 Xaa48 Xaa49 Xaa50 Cys Xaa52 Xaa53

Xaa54 Cys Xaa56 Xaa57 Xaa58
```

"Xaa" refers to a position in a peptide chain that can be any of a number of different amino acids. In a first example, Xaa can by any amino acid except cysteine. In another example, one or more of the following apply: Xaa10 can be Asp or Glu; Xaa11 can be Asp, Gly, Ser, Val, Asn, Ile, Ala or Thr; Xaa13 can be Pro, Arg, His, Asn, Ser, Thr, Ala, Gly, Lys or Gln; Xaa15 can be Arg, Lys, Ala, Ser, Gly, Met, Asn or Gln; Xaa16 can be Ala, Gly, Ser, Asp or Asn; Xaa17 can be Ala, Asn, Ser, Ile, Gly, Val, Gln or Thr; Xaa18 can be His, Leu, Gln or Ala; Xaa19 can be Pro, Gln, Leu, Asn or Ile; Xaa21 can be Trp, Phe, Tyr, His or Ile; Xaa31 can be Glu, Asp, Gln, Asn, Ser, Ala, Val, Leu, Ile or Thr; Xaa32 can be Glu, Gln, Asp Asn, Pro, Thr, Leu, Ser, Ala, Gly or Val; Xaa34 can be Ile, Thr, Ser, Val, Ala, Asn, Gly or Leu; Xaa35 can be Tyr, Trp or Phe; Xaa39 can be Glu, Gly, Ala, Ser or Asp. Amino acids Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 can be any amino acid.

Additionally, each of the first four and at last three amino acids of SEQ ID NO:1 can optionally be present or absent and can be any amino acid, if present, e.g., any non-cysteine amino acid.

In one embodiment, the polypeptide has a sequence with one or more of the following properties: Xaa11 can be Asp, Gly, Ser or Val; Xaa13 can be Pro, Arg, His or Asn; Xaa15 can be Arg or Lys; Xaa16 can be Ala or Gly; Xaa17 can be Ala, Asn, Ser or Ile; Xaa18 can be His, Leu or Gln; Xaa19 can be Pro, Gln or Leu; Xaa21 can be Trp or Phe; Xaa31 is Glu; Xaa32 can be Glu or Gln; Xaa34 can be Ile, Thr or Ser; Xaa35 is Tyr; and Xaa39 can be Glu, Gly or Ala.

An exemplary polypeptide can include the following amino acids: Xaa10 is Asp; Xaa11 is Asp; Xaa13 can be Pro or Arg; Xaa15 is Arg; Xaa16 can be Ala or Gly; Xaa17 is Ala; Xaa18 is His; Xaa19 is Pro; Xaa21 is Trp; Xaa31 is Glu; Xaa32 is Glu; Xaa34 can be Ile or Ser; Xaa35 is Tyr; and Xaa39 is Gly.

It is also possible to use portions of the polypeptides described herein. For example, polypeptides could include binding domains for specific kallikrein epitopes. For example, the binding loops of Kunitz domains can by cyclized and used in isolation or can be grafted onto another domain, e.g., a framework of another Kunitz domain. It is also possible to remove one, two, three, or four amino acids from the N-terminus of an amino acid sequence described herein, and/or one, two, three, four, or five amino acids from the C-terminus of an amino acid sequence described herein.

Examples of sequences encompassed by SEQ ID NO:1 are described by the following (where not indicated, "Xaa" refers to any amino acid, any non-cysteine amino acid or any amino acid from the same set of amino acids that are allowed for SEQ ID NO:1):

```
                                                           (SEQ ID NO: 56)
    Met His Ser Phe Cys Ala Phe Lys Ala Xaa10 Xaa11 Gly Xaa13 Cys Xaa15

Xaa16 Xaa17 Xaa18 Xaa19 Arg Xaa21 Phe Phe Asn Ile Phe Thr Arg Gln Cys Xaa31

Xaa32 Phe Xaa34 Xaa35 Gly Gly Cys Xaa39 Gly Asn Gln Asn Arg Phe Glu Ser Leu Glu

Glu Cys Lys Lys Met Cys Thr Arg Asp.

(amino acids 3-60 of SEQ ID NO: 2)
    Met His Ser Phe Cys Ala Phe Lys Ala Asp Asp Gly Pro Cys Arg Ala Ala His Pro Arg Trp Phe Phe Asn Ile Phe Thr Arg Gln Cys Glu Glu Phe Ile Tyr Gly Gly Cys Glu Gly Asn Gln Asn Arg Phe Glu Ser Leu Glu Glu Cys Lys Lys Met Cys Thr Arg Asp, (SEQ ID NO: 4)
    Met His Ser Phe Cys Ala Phe Lys Ala Asp Asp Gly Pro Cys Lys Ala Asn His Leu Arg Phe Phe Asn Ile Phe Thr Arg Gln Cys Glu Glu Phe Ser Tyr Gly Gly Cys Gly Gly Asn Gln Asn Arg Phe Glu Ser Leu Glu Glu Cys Lys Lys Met Cys Thr Arg Asp, (SEQ ID NO: 5)
    Met His Ser Phe Cys Ala Phe Lys Ala Asp Asp Gly His Cys Lys Ala Asn His Gln Arg Phe Phe Asn Ile Phe Thr Arg Gln Cys Glu Glu Phe Thr Tyr Gly Gly Cys Gly Gly Asn Gln Asn Arg Phe Glu Ser Leu Glu Glu Cys Lys Lys Met Cys Thr Arg Asp,
```

-continued (SEQ ID NO: 6)
Met His Ser Phe Cys Ala Phe Lys Ala Asp Asp Gly His Cys Lys Ala Asn His Gln
Arg Phe Phe Phe Asn Ile Phe Thr Arg Gln Cys Glu Gln Phe Thr Tyr Gly Gly Cys Ala
Gly Asn Gln Asn Arg Phe Glu Ser Leu Glu Glu Cys Lys Lys Met Cys Thr Arg Asp, (SEQ ID NO: 7)
Met His Ser Phe Cys Ala Phe Lys Ala Asp Asp Gly His Cys Lys Ala Ser Leu Pro
Arg Phe Phe Phe Asn Ile Phe Thr Arg Gln Cys Glu Glu Phe Ile Tyr Gly Gly Cys Gly Gly
Asn Gln Asn Arg Phe Glu Ser Leu Glu Glu Cys Lys Lys Met Cys Thr Arg Asp, (SEQ ID NO: 8)
Met His Ser Phe Cys Ala Phe Lys Ala Asp Asp Gly His Cys Lys Ala Asn His Gln
Arg Phe Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 9)
Met His Ser Phe Cys Ala Phe Lys Ala Asp Asp Gly His Cys Lys Gly Ala His Leu
Arg Phe Phe Phe Asn Ile Phe Thr Arg Gln Cys Glu Glu Phe Ile Tyr Gly Gly Cys Glu Gly
Asn Gln Asn Arg Phe Glu Ser Leu Glu Glu Cys Lys Lys Met Cys Thr Arg Asp, (SEQ ID NO: 10)
Met His Ser Phe Cys Ala Phe Lys Ala Asp Asp Gly Arg Cys Lys Gly Ala His Leu
Arg Phe Phe Phe Asn Ile Phe Thr Arg Gln Cys Glu Glu Phe Be Tyr Gly Gly Cys Glu Gly
Asn Gln Asn Arg Phe Glu Ser Leu Glu Glu Cys Lys Lys Met Cys Thr Arg Asp, (SEQ ID NO: 11)
Met His Ser Phe Cys Ala Phe Lys Ala Asp Gly Gly Arg Cys Arg Gly Ala His Pro
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 12)
Met His Ser Phe Cys Ala Phe Lys Ala Asp Asp Gly Pro Cys Arg Ala Ala His Pro
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 13)
Met His Ser Phe Cys Ala Phe Lys Ala Asp Val Gly Arg Cys Arg Gly Ala His Pro
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 14)
Met His Ser Phe Cys Ala Phe Lys Ala Asp Val Gly Arg Cys Arg Gly Ala Gln Pro
Arg Phe Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 15)
Met His Ser Phe Cys Ala Phe Lys Ala Asp Asp Gly Ser Cys Arg Ala Ala His Leu
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 16)
Met His Ser Phe Cys Ala Phe Lys Ala Glu Gly Gly Ser Cys Arg Ala Ala His Gln
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, -continued (SEQ ID NO: 17)
Met His Ser Phe Cys Ala Phe Lys Ala Asp Asp Gly Pro Cys Arg Gly Ala His Leu
Arg Phe Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 18)
Met His Ser Phe Cys Ala Phe Lys Ala Asp Asp Gly His Cys Arg Gly Ala Leu Pro
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 19)
Met His Ser Phe Cys Ala Phe Lys Ala Asp Ser Gly Asn Cys Arg Gly Asn Leu Pro
Arg Phe Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 20)
Met His Ser Phe Cys Ala Phe Lys Ala Asp Ser Gly Arg Cys Arg Gly Asn His Gln
Arg Phe Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 21)
Met His Ser Phe Cys Ala Phe Lys Ala Asp Gly Gly Arg Cys Arg Ala Ile Gln Pro
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp, (SEQ ID NO: 22)
Met His Ser Phe Cys Ala Phe Lys Ala Asp Asp Gly Arg Cys Arg Gly Ala His Pro
Arg Trp Phe Phe Asn Ile Phe Thr Arg Gln Cys Glu Glu Phe Ser Tyr Gly Gly Cys Gly
Gly Asn Gln Asn Arg Phe Glu Ser Leu Glu Glu Cys Lys Lys Met Cys Thr Arg Asp.

Additional examples of sequence include those that differ by at least one amino acid, but fewer than seven, six, five, four, three, or two amino acids differences relative to an amino acid sequence described herein, e.g., an amino acid sequence provided above. In one embodiment, fewer than three, two, or one differences are in one of the binding loops. For example, the first binding loop may have no differences relative to an amino acid sequence described herein, e.g., an amino acid sequence provided above. In another example, neither the first nor the second binding loop differs from an amino acid sequence described herein, e.g., an amino acid sequence provided above.

FIGS. 3A and 3B provides an amino acid sequence alignment of these sequences, the native LACI sequence from which these variants were derived (SEQ ID NO:32), and other known Kunitz domains (SEQ ID NOS: 29-31 and 33-53). Still others polypeptides that inhibit kallikrein include an about 58-amino acid sequence of amino acids 3-60 of SEQ ID NO:2 or the PEP-1 polypeptide having the 60-amino acid sequence of SEQ ID NO:2. The term "PEP-1" and "DX-88" as used herein refer to the 60-amino acid sequence of SEQ ID NO:2. A nucleotide sequence encoding the amino acid sequence of SEQ ID NO:2 is provided in SEQ ID NO:3 (see, e.g., nucleotides 309-488 in FIG. 2). It is understood that based on the known genetic code, degenerate forms of the nucleotide sequence of SEQ ID NO:3 can be obtained by simply substituting one or more of the known degenerate codons for each amino acid encoded by the nucleotide sequence. Nucleotides 7-180 of SEQ ID NO:3, and degenerate forms thereof, encode the non-naturally occurring Kunitz domain polypeptide that includes the 58-amino acid sequence of amino acids 3-60 of SEQ ID NO:2, a related sequence, or a functional fragment thereof.

In one embodiment, the polypeptide is other than aprotinin, e.g., differs from aprotinin, by at least one, two, three, five, ten, or fifteen amino acids.

Polypeptides described herein can be made synthetically using any standard polypeptide synthesis protocol and equipment. For example, the stepwise synthesis of a polypeptide can be carried out by the removal of an amino (N) terminal-protecting group from an initial (i.e., carboxy-terminal) amino acid, and coupling thereto of the carboxyl end of the next amino acid in the sequence of the polypeptide. This amino acid is also suitably protected. The carboxyl group of the incoming amino acid can be activated to react with the N-terminus of the bound amino acid by formation into a reactive group such as formation into a carbodiimide, a symmetric acid anhydride, or an "active ester" group such as hydroxybenzotriazole or pentafluorophenyl esters. Preferred solid-phase peptide synthesis methods include the BOC method, which utilizes tert-butyloxycarbonyl as the I-amino protecting group, and the FMOC method, which utilizes 9-fluorenylmethloxycarbonyl to protect the alpha-amino of the amino acid residues. Both methods are well known to those of skill in the art (Stewart, J. and Young, J., Solid-Phase Peptide Synthesis (W. H. Freeman Co., San Francisco 1989); Merrifield, J., 1963. Am. Chem. Soc., 85:2149-2154; Bodanszky, M. and Bodanszky, A., The Practice of Peptide Synthesis (Springer-Verlag, New York 1984)). If desired, additional amino- and/or carboxy-terminal amino acids can be designed into the amino acid sequence and added during polypeptide synthesis.

Polypeptides can also be produced using recombinant technology. Recombinant methods can employ any of a number of cells and corresponding expression vectors, including but not limited to bacterial expression vectors, yeast expression vectors, baculovirus expression vectors, mammalian viral expression vectors, and the like. A polypeptide described herein can be produced by a transgenic animal, e.g., in the mammary gland of a transgenic animal. In some cases, it could be necessary or advantageous to fuse the coding sequence for a polypeptide that inhibits kallikrein (e.g., a polypeptide that includes a Kunitz domain) to another coding sequence in an expression vector to form a fusion polypeptide that is readily expressed in a host cell. Part or all of the additional sequence can be removed, e.g., by protease digestion.

An exemplary recombinant expression system for producing a polypeptide that inhibits kallikrein (e.g., a polypeptide that includes a Kunitz domain) is a yeast expression vector, which permits a nucleic acid sequence encoding the amino acid sequence for the inhibitor polypeptide to be linked in the same reading frame with a nucleotide sequence encoding the MATα prepro leader peptide sequence of Saccharomyces cerevisiae, which in turn is under the control of an operable yeast promoter. The resulting recombinant yeast expression plasmid can be transformed by standard methods into the cells of an appropriate, compatible yeast host, which cells are able to express the recombinant protein from the recombinant yeast expression vector. Preferably, a host yeast cell transformed with such a recombinant expression vector is also able to process the fusion protein to provide an active inhibitor polypeptide. An other exemplary yeast host for producing recombinant polypeptides is Pichia pastoris.

As noted above, polypeptides that inhibit kallikrein can include a Kunitz domain polypeptide described herein. Some polypeptides can include an additional flanking sequence, preferably of one to six amino acids in length, at the amino and/or carboxy-terminal end, provided such additional amino acids do not significantly diminish kallikrein binding affinity or kallikrein inhibition activity so as to preclude use in the methods and compositions described herein. Such additional amino acids can be deliberately added to express a polypeptide in a particular recombinant host cell or can be added to provide an additional function, e.g., to provide a linker to another molecule or to provide an affinity moiety that facilitates purification of the polypeptide. Preferably, the additional amino acid(s) do not include cysteine, which could interfere with the disulfide bonds of the Kunitz domain.

An exemplary Kunitz domain polypeptide includes the amino acid sequence of residues 3-60 of SEQ ID NO:2. When expressed and processed in a yeast fusion protein expression system (e.g., based on the integrating expression plasmid pHIL-D2), such a Kunitz domain polypeptide retains an additional amino terminal Glu-Ala dipeptide from the fusion with the MATalpha-prepro leader peptide sequence of S. cerevisiae. When secreted from the yeast host cell, most of the leader peptide is processed from the fusion protein to yield a functional polypeptide (referred to herein as "PEP-1") having the amino acid sequence of SEQ ID NO:2 (see boxed region in FIG. 2).

In one embodiment, an inhibitor of kallikrein, e.g., a polypeptide inhibitor, has a binding affinity for kallikrein that is on the order of 1000 times higher than that of aprotinin, which is currently approved for use in CABG procedures to reduce blood loss. The surprisingly high binding affinities of such kallikrein inhibitors combined with their high degree of specificity for kallikrein to the exclusion of other molecular targets (see Table 1, below) provide for particularly useful inhibitors. However, inhibitors with lesser affinity or specificity also have their applications.

A typical Kunitz domain, e.g., that includes, SEQ ID NO:1, contains a number of invariant positions, e.g., positions corresponding to position 5, 14, 30, 33, 38, 45, 51 and 55 in the BPTI numbering scheme are cysteine. The spacing between these positions may vary to the extent allowable within the Kunitz domain fold, e.g., such that three disulfide bonds are formed. Other positions such as, for example, positions 6, 7, 8, 9, 20, 24, 25, 26, 27, 28, 29, 41, 42, 44, 46, 47, 48, 49, 50, 52, 53 and 54, or positions corresponding to those positions, can be any amino acid (including non-genetically encoded occurring amino acids). In a particularly preferred embodiment, one or more amino acids correspond to that of a native sequence (e.g., SEQ ID NO:32, see FIG. 3). In another embodiment, at least one variable position is different from that of the native sequence. In yet another preferred embodiment, the amino acids can each be individually or collectively substituted by a conservative or non-conservative amino acid substitution.

Conservative amino acid substitutions replace an amino acid with another amino acid of similar chemical nature and may have no affect on protein function. Non-conservative amino acid substitutions replace an amino acid with another amino acid of dissimilar chemical structure. Examples of conserved amino acid substitutions include, for example, Asn→Gln, Arg→Lys and Ser→Thr. In a preferred embodiment, 1, 2, 3, 4, 5, 6, 7, 8, 9, 10, 11, 12, 13, 14, 15, 16, 17, 18, 19, 20 and/or 21 of these amino acids can be independently or collectively, in any combination, selected to correspond to the corresponding position of SEQ ID NO:2.

Other positions, for example, positions 10, 11, 13, 15, 16, 17, 18, 19, 21, 22, 23, 31, 32, 34, 35, 39, 40, 43 and 45, or positions corresponding to those positions can be any of a selected set of amino acids. For example, SEQ ID NO:1 defines a set of possible sequences. Each member of this set contains, for example, a cysteine at positions 5, 14, 30, 51 and 55, and any one of a specific set of amino acids at positions 10, 11, 13, 15, 16, 17, 18, 19, 21, 22, 23, 31, 32, 34, 35, 39, 40, 43 and 45, or positions corresponding to those positions. In a preferred embodiment, 1, 2, 3, 4, 5, 6, 7, 8, 9, 10, 11, 12, 13, 14, 15, 16, 17, 18 and/or 19 of these amino acids can be independently or collectively, in any combination, selected to correspond to the corresponding position of SEQ ID NO:2. The polypeptide preferably has at least 80%, 85%, 90%, 95, 97, 98, or 99% identity to SEQ ID NO:2.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), J. Mol. Biol. 48:444-453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation) are a Blossum 62 scoring matrix with a gap penalty of 12, a gap extend penalty of 4, and a frameshift gap penalty of 5.

Useful polypeptides can also be encoded by a nucleic acid that hybridizes to a nucleic acid that encodes a polypeptide described herein. The nucleic acids can hybridize under medium, high, or very high stringency conditions. As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, 1% SDS at 65° C.

Modifications

It is possible to modify polypeptides that inhibit a Kunitz domain in a variety of ways. For example, the polypeptides can be attached to one or more polyethylene glycol moieties to stabilize the compound or prolong retention times, e.g., by at least 2, 4, 5, 8, 10, 15, 20, 50, 100, 500 or 1000 fold.

A polypeptide that inhibits kallikrein can be associated with (e.g., conjugated to) a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. A plurality of polymer moieties can be attached to one polypeptide, e.g., at least two, three, or four such moieties, e.g., having an average molecular weight of about 2,000 to 7,000 Daltons.

For example, the polypeptide can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Other compounds can also be attached to the same polymer, e.g., a cytotoxin, a label, or another targeting agent or an unrelated agent. Mono-activated, alkoxy-terminated polyalkylene oxides (PAO's), e.g., monomethoxy-terminated polyethylene glycols (mPEG's); $C_{1-4}$ alkyl-terminated polymers; and bis-activated polyethylene oxides (glycols) can be used for crosslinking. See, e.g., U.S. Pat. No. 5,951,974.

Anti-Thrombolytic Agents

Anti-thrombolytic agents are agents that reduce or prevent dissolution of a blood clot, stabilize a blood clot, increase clotting and/or prevent abnormal amounts of blood loss such as hemorrhaging by maintaining, stabilizing or increasing a blood clot. Preferably, the anti-thrombolytic agent is an anti-fibrinolytic agent. Anti-fibrinolytic agents are agents that prevent or reduce the dissolution or breakdown of fibrin. Examples of anti-fibrinolytic agents include tranexamic acid (Cyklokapron™), epsilon amino caproic acid (Amicar™), aprotinin (Trasyol™), Desmopressin (DDAVP), pirfenidone, and combinations thereof. The anti-fibrinolytic activity of an agent may be determined by any in vitro clot lysis activity known in the art, such as the purified clot lysis assay described by Carlson, et al., *Anal. Biochem.* 168, 428-435 (1988) and its modified form described by Bennett, W. F. et al., 1991, supra, the entire contents of which are hereby incorporated by reference.

Methods and Compositions

The kallikrein inhibitors and the anti-thrombolytic agents described herein can be used in methods for preventing or reducing blood loss, e.g., perioperative blood loss; methods for preventing or reducing injury associated with ischemia (e.g., reperfusion injury associated with ischemia); and/or a systemic inflammatory response (SIR) in a patient, especially associated with surgery. The surgery can be, e.g., a cardiothoracic surgery, (e.g., cardiopulmonary bypass or coronary artery bypass grafting); orthopedic surgery (e.g., hip or knee replacement or bone fracture); liver surgery; kidney surgery; procedures that utilize extracorporeal circulation or dialysis; and any other procedure which can result in perioperative blood loss. The method includes administering a non-naturally occurring inhibitor of kallikrein, e.g., plasma kallikrein, in combination with an anti-thrombolytic agent, e.g., an anti-fibrinolytic agent.

In one embodiment, a method for treatment includes administration of a non-naturally occurring polypeptide comprising a Kunitz domain as the inhibitor of kallikrein. One embodiment of the method uses a polypeptide containing an amino acid sequence of SEQ ID NO:1 that has an affinity for kallikrein that is approximately 30-fold or more higher than that of a broad range serine protease, e.g., aprotinin, which is isolated from bovine lung and currently approved for use in CABG procedures (TRASYLOL™, Bayer Corporation Pharmaceutical Division, West Haven, Conn.).

Patients subjected to any of a number of surgical procedures, especially those involving extra-corporeal circulation, e.g., cardiothoracic surgery, such as, for example, CPB, and/or bone trauma, such as sternal split or hip replacement, are at risk for perioperative blood loss and inflammation. Contact of a patient's blood with the cut surfaces of bone or of CPB equipment is sufficient to activate one or several undesirable cascade responses, including a contact activation system (CAS), which can lead to extensive perioperative blood loss requiring immediate blood transfusion, as well as a systemic inflammatory response (SIR), which, in turn, can result in permanent damage to tissues and organs. While not desiring to be limited to any particular mechanism or theory, it appears that the blood loss that occurs associated with cardiothoracic surgery, e.g., CPB, as in a CABG procedure, probably results from extensive capillary leakage, which can result in significant loss of blood that must be replaced by immediate blood transfusion.

The combination treatment described herein can be used to prevent or reduce perioperative blood loss as well as various ischemias and SIR in a patient subjected to a surgical procedure, and especially wherein the surgical procedure requires extra-corporeal circulation, e.g., cardiothoracic surgery, such as, for example, CPB. The combination treatment can be particularly useful for preventing or reducing perioperative blood loss and/or SIR in a patient subjected to a CABG procedure requiring CPB or other cardiac surgery. Further, the combination treatment described herein can be used to prevent or reduce cerebral ischemia (such as stroke) and/or reperfusion injury associated with cerebral ischemia (e.g., stroke).

Exemplary compositions for medical use comprise a kallikrein inhibitor described herein, an anti-thrombolytic agent described herein or both a kallikrein inhibitor described herein and an anti-thrombolytic agent described herein. Such compositions can further include one or more pharmaceutically acceptable buffers, carriers, and excipients, which can provide a desirable feature to the composition including, but not limited to, enhanced administration of the composition to a patient, enhanced circulating half-life of the inhibitor and/or anti-thrombolytic agent, enhanced compatibility of the inhibitor and/or anti-thrombolytic agent with patient blood chemistry, enhanced storage of the composition, and/or enhanced delivery and/or efficacy of the inhibitor and/or anti-thrombolytic agent upon administration to a patient. In addition to a kallikrein inhibitor and/or anti-thrombolytic agent described herein, compositions can further include one or more other pharmaceutically active compounds that provide an additional prophylactic or therapeutic benefit to a patient, e.g., a patient of an invasive surgical procedure or a patent otherwise at risk for, having or previously had cerebral ischemia and/or reperfusion injury associated with cerebral ischemia. For example, the compositions can include another compound described herein.

Perioperative Blood Loss and Reduced Heart Bloodflow

Due to the many advances in medicine, a number of highly invasive surgical procedures are carried out each day that result in blood loss, or place patients at a high risk for blood loss. Such patients are generally carefully monitored to restore and maintain normal blood supply and hemostasis, and they may need blood transfusions. Surgical procedures that involve blood loss include those involving extra-corporeal circulation methods such as cardiothoracic surgery, e.g., CPB. In such methods, a patient's heart is stopped and the circulation, oxygenation, and maintenance of blood volume are carried out artificially using an extra-corporeal circuit and a synthetic membrane oxygenator. These techniques are commonly used during cardiac surgery. Additionally, it is apparent that surgery involving extensive trauma to bone, such as the sternal split necessary in CABG or hip replacement procedures, is also associated with activation of the CAS, which can result in a variety of disruptions in the blood and vasculature.

Atherosclerotic coronary artery disease (CAD) causes a narrowing of the lumen of one or several of the coronary arteries; this limits the flow of blood to the myocardium (i.e., the heart muscle) and can cause angina, heart failure, and myocardial infarcts. In the end stage of coronary artery atherosclerosis, the coronary circulation can be almost completely occluded, causing life threatening angina or heart failure, with a very high mortality. CABG procedures may be required to bridge the occluded blood vessel and restore blood to the heart; these are potentially life saving. CABG procedures are among the most invasive of surgeries in which one or more healthy veins or arteries are implanted to provide a "bypass" around the occluded area of the diseased vessel. CABG procedures carry with them a small but important perioperative risk, but they are very successful in providing patients with immediate relief from the mortality and morbidity of atherosclerotic cardiovascular disease. Despite these very encouraging results, repeat CABG procedures are frequently necessary, as indicated by an increase in the number of patients who eventually undergo second and even third procedures; the perioperative mortality and morbidity seen in primary CABG procedures is increased in these re-do procedures.

There have been improvements in minimally invasive surgical techniques for uncomplicated CAD. However, nearly all CABG procedures performed for valvular and/or congenital heart disease, heart transplantation, and major aortic procedures, are still carried out on patients supported by CPB. In CPB, large cannulae are inserted into the great vessels of a patient to permit mechanical pumping and oxygenation of the blood using a membrane oxygenator. The blood is returned to the patient without flowing through the lungs, which are hypoperfused during this procedure. The heart is stopped using a cardioplegic solution, the patient cooled to help prevent brain damage, and the peripheral circulating volume increased by an extracorporeal circuit, i.e., the CPB circuit, which requires "priming" with donor blood and saline mixtures are used to fill the extracorporeal circuit. CPB has been extensively used in a variety of procedures performed for nearly half a century with successful outcomes. The interaction between artificial surfaces, blood cells, blood proteins, damaged vascular endothelium, and extravascular tissues, such as bone, disturbs hemostasis and frequently activates the CAS, which, as noted above, can result in a variety of disruptions in the blood and vasculature. Such disruption leads to excess perioperative bleeding, which then requires immediate blood transfusion. A consequence of circulating whole blood through an extracorporeal circuit in CPB can also include the systemic inflammatory response (SIR), which is initiated by contact activation of the coagulation and complement systems. Indeed, much of the morbidity and mortality associated with seemingly mechanically successful CPB surgical procedures is the result of the effects of activating coagulation, fibrinolysis, or complement systems. Such activation can damage the pulmonary system, leading to adult respiratory distress syndrome (ARDS), impairment of kidney and splanchnic circulation, and induction of a general coagulopathy leading to blood loss and the need for transfusions. In addition to the dangers of perioperative blood loss, additional pathologies associated with SIR include neurocognitive deficits, stroke, renal failure, acute myocardial infarct, and cardiac tissue damage.

Blood transfusions also present a significant risk of infection and elevate the cost of CABG or other similar procedures that require CPB. In the absence of any pharmacological intervention, three to seven units of blood must typically be expended on a patient, even with excellent surgical techniques. Accordingly, there is considerable incentive for the development of new and improved pharmacologically effective compounds and treatment protocols to reduce or prevent perioperative bleeding and SIR in patients subjected to CPB and CABG procedures. Use of the inhibitors described herein in combination with various anti-thrombolytic agents (e.g., anti-fibrinolytic agents) can improve these various treatments and lead to reduction and/or amelioration of the undesirable symptoms that can occur.

Cerebral Ischemia and Reperfusion Injury

The methods described herein are useful for reducing or preventing cerebral ischemia as well as reperfusion injury associated with cerebral ischemia. A "cerebral ischemic attack" or "cerebral ischemia" is an ischemic condition in which blood supply to the brain is blocked. This interruption in the blood supply to the brain may result from a variety of causes including, but not limited to, an intrinsic blockage or occlusion of the blood vessel itself, a remotely originated source of occlusion, decreased perfusion pressure or increased blood viscosity resulting in decreased cerebral blood flow, or ruptured or leaky blood vessels in the subarachnoid space or intracerebral tissue. Cerebral ischemia may result in either transient or permanent deficits and the seriousness of the neurological damage in a patient who has experienced cerebral ischemia depends on the intensity and duration of the ischemia event. A transient ischemia attack (TIA) is one in which the blood flow to the brain is briefly interrupted and causes temporary neurological deficits. Symptoms of TIA include numbness of weakness of face or limbs, loss of ability to speak clearly and/or understand the speech of others, a loss of vision or dimness of vision and dizziness. Permanent cerebral ischemia attacks, also called strokes, are caused by a longer interruption in blood flow to the brain resulting from an embolism, a thrombus or bleeding in the brain (e.g., a hemorrhage). The term "thromboembolic stroke" or "thromboembolism" is used herein to refer to a stroke caused by either a thrombosis or an embolism. A stroke causes a loss of neurons typically resulting in a neurological deficit that may improve but does not entirely resolve. The combination treatments described herein are useful in preventing or reducing stroke including embolic-, thrombolic-, thromboembolic- and hemorrhage-associated strokes. Strokes can be caused by a variety of causes. One category includes perioperative strokes that can be associated with thrombus or embolism formation.

In stroke patients, there is a core of the neurological deficit marked by total ischemia and/or tissue necrosis. This area is normally surrounded by ischemic tissue, referred to as the ischemic penumbra, that receives collateral circulation. Ischemia in the penumbra does not always result in irreversible damage. In some cases, restoration of blood flow (reperfusion) into the penumbra may prevent total ischemia and necrosis in this area. However, reperfusion has also been associated with injury to the tissue surrounding the core. Once blood flow is returned, blood cells such as neutrophils, attack the damaged tissue which can cause additional inflammation and/or damage. Reperfusion injury is associated with an influx of neutrophils into the affected tissue and subsequent activation of the neutrophils. Neutrophils can release lytic enzymes that directly induce tissue damage and proinflammatory mediators such as cytokines that amplify local inflammatory reaction. The influx of neutrophils to a site of ischemic damage can also plug capillaries and cause vasoconstriction. It has been found that kallikrein plays a role in neutrophil chemotaxis, neutrophil activation and reperfusion injury. Thus, the kallikrein inhibitors described herein can be used to prevent or reduce reperfusion injury, e.g., by reducing or preventing one or more of: 1) neutrophil infiltration, 2) neutrophil activation; 3) cytokine release; 4) elastase release; and 5) vasodilation. For example, a kallikrein inhibitor can be used to inhibit bradykinin and Factor XII. The kallikrein inhibitors can be used in combination with one or more anti-thrombolytic agent, e.g., one or more anti-thrombolytic agent described herein.

Administration

A kallikrein inhibitor and/or anti-thrombolytic agent can be administered to a patient before, during, and/or after an event that causes or is associated with blood loss, e.g., a surgical procedure, or an ischemic event, e.g., a cerebral ischemic attack, in a pharmaceutically acceptable composition or in connection with another disorder or event described herein. The patient is generally a human, but may also be a non-human mammal. Human patients include adults, e.g., patients between ages 19-25, 26-40, 41-55, 56-75, and 76 and older, and pediatric patients, e.g., patients between ages 0-2, 3-6, 7-12, and 13-18.

The term "pharmaceutically acceptable" composition refers to a non-toxic carrier or excipient that may be administered to a patient, together with a kallikrein inhibitor and/or anti-thrombolytic agent described herein. The carrier or excipient is chosen to be compatible with the biological or pharmacological activity of the composition. The inhibitors and/or anti-thrombolytic agents described herein can be administered locally or systemically by any suitable means for delivery of an inhibitory amount of the inhibitor and/or anti-thrombolytic agent to a patient including but not limited to systemic administrations such as, for example, intravenous and inhalation. Parenteral administration is particularly preferred.

For parenteral administration, the kallikrein inhibitor and/or the anti-thrombolytic agent can be injected intravenously, intramuscularly, intraperitoneally, or subcutaneously. Intravenous administration is preferred. Typically, compositions for intravenous administration are solutions in sterile isotonic aqueous buffer. Other pharmaceutically acceptable carriers include, but are not limited to, sterile water, saline solution, and buffered saline (including buffers like phosphate or acetate), alcohol, vegetable oils, polyethylene glycols, gelatin, lactose, amylose, magnesium stearate, talc, silicic acid, paraffin, etc. Where necessary, the composition can also include a solubilizing agent and a local anaesthetic such as lidocaine to ease pain at the site of the injection, preservatives, stabilizers, wetting agents, emulsifiers, salts, lubricants, etc. as long as they do not react deleteriously with the active compounds. Similarly, the composition can comprise conventional excipients, e.g., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline can be provided so that the ingredients can be mixed prior to administration.

In one embodiment, the kallikrein inhibitor and/or anti-thrombolytic agent is administered to a patient as an intravenous infusion according to any approved procedure. For example, a non-naturally occurring kallikrein inhibitor described herein and an anti-thrombolytic agent (e.g., an anti-fibrinolytic agent) can be administered to a patient subjected to a CABG procedure at the times similar to those currently used in approved protocols for administering aprotinin and in an amount necessary to provide a patient with a required number or concentration of kallikrein inhibitory units (KIU). In another embodiment, each of the non-naturally occurring kallikrein inhibitor and the anti-thrombolytic agent, e.g., anti-fibrinolytic agent, is administered in an amount necessary to provide a patient with a required number or concentration of kallikrein inhibitory units (KIU).

A kallikrein inhibitor and/or anti-thrombolytic agent described herein can also be administered to a patient in the immediate postoperative period, when bleeding abnormalities can occur as a consequence of downstream effects of SIR. For example, in a procedure involving CPB, an inhibitor and/or anti-thrombolytic agent described herein can be administered to a patient as an initial loading dose, e.g., an effective amount over the course of a convenient time, such as 10 minutes, prior to induction of anesthesia. Then, at induction of anesthesia, a second dose of the inhibitor and/or anti-thrombolytic agent can be injected into the CPB priming fluid ("pump prime volume"). The patient can then be placed on a continuous and controlled intravenous infusion dose for the duration of the surgical procedure, and after the procedure if indicated.

In other embodiments, a kallikrein inhibitor and/or anti-thrombolytic agent can be administered after an ischemic event, e.g., after a stroke, e.g., 5, 10, 15, 30, 45 minutes, 1, 2, 3, 5, 10, 15, 20 hours or more after a stroke. Preferably, the inhibitor and/or anti-thrombolytic agent is administered within 12 to 60 hours, e.g., within 24 to 48 hours, after a stroke. In some embodiments, a kallikrein inhibitor and/or anti-thrombolytic agent is administered after an ischemic event, e.g., after a stroke, but prior to reperfusion of the damaged tissue. In other embodiments, a kallikrein inhibitor and/or anti-thrombolytic agent is administered during reperfusion or after reperfusion has begun. In yet another embodiment, a kallikrein inhibitor and/or anti-thrombolytic agent is administered after reperfusion has occurred. An "effective" amount in this context is an amount sufficient to reduce one or more symptoms associated with cerebral ischemia and/or reperfusion injury associated with cerebral ischemia which otherwise would have occurred in a subject experiencing a cerebral ischemia and/or reperfusion injury associated with cerebral ischemia absent the treatment. Several physiological parameters may be used to assess stroke and reperfusion injury associated with stroke including infarct size, regional cerebral blood flow, intracranial pressure, anterograde amnesia, retrograde amnesia, dementia, cognitive function and/or emotion, and cerebral edema, for example, as compared to pretreatment patient parameters, untreated stroke patients or stroke patients treated with the other therapeutic agent but not the combination with the inhibitor (e.g., the Kunitz domain polypeptide or other compound described herein) or visa versa.

Parameters that can be evaluated for determining a dose of the kallikrein inhibitor, the anti-thrombolytic agent, or both are described below with regards to DX-88 (a non-naturally occurring kallikrein inhibitor) and aprotinin (an anti-fibrinolytic agent). By determining information regarding, for example, the KIU and binding specificity, an appropriate dose of each of the kallikrein inhibitor and the anti-thrombolytic agent can be determined for the desired therapeutic or prophylactic effect.

With respect to an implementation in which DX-88 or a DX-88-related inhibitor is used, the affinity constant (Ki) of DX-88 is at least about 1000 times greater than aprotinin for kallikrein inhibition. Accordingly, a dose of DX-88 or an inhibitor of similar affinity can be, e.g., at least about 5, 10, 15, 20, 30, 50, 100, 500 or 1000 times lower than aprotinin on a mole per mole basis. The dose could also be modulated as a function of the amount of kallikrein activated during an event (e.g., CPB), the specificity of the DX-88-kallikrein interaction in vivo, the concentration of kallikrein eliciting SIRS, and pharmacological distribution. In one aspect, the dose of DX-88 or an inhibitor of similar affinity administered in combination with an anti-fibrinolytic agent such as aprotinin can be adjusted such that the KIU for the combination is the same as it would be if only DX-88 or only aprotinin were administered. In other embodiments, each of DX-88 (or an inhibitor of similar affinity) and the anti-fibrinolytic agent, e.g., aprotinin, is administered at a dose the same or similar to that given in the absence of the other agent. Similar adjustments can be made for other anti-thrombolytic agents, e.g., anti-fibrinolytic agents, described herein.

The total amount of circulating prekallikrein in plasma is reported to be approximately 500 nM to 600 nM. Silverberg, M. et al., "The Contact System and Its Disorders," in Blood: Principles and Practice of Hematology, Handin, R. et al., eds, J B Lippincott Co., Philadelphia, 1995). If all prekallikrein is activated, about 520 nmoles/L of DX-88 can be used to inhibit kallikrein in a stoichiometric manner. An individual having 5 L of plasma would require a dose of 2.6 micromoles DX-88, or approximately 18 mg based on the molecular weight of DX-88 of 7,054 Daltons. This was calculated as follows: the $K_i$ of DX88 is 0.044 nM. When it is desired to have a concentration of plasma kallikrein (PK) of, e.g., 1 nM, the formula $K_i$=0.044 nM=[DX88]×[PK]/

[DX88-PK]=[DX88]×1 nm/499 nM, indicates that the concentration of free DX-88 is 22.0 nM. Thus, the total amount of DX-88 needed would be 499+22 or 521 nM. The dose can be reduced proportionally if not all of the prekallikrein is activated or if a portion of the kallikrein is deactivated by an endogenous inhibitor, e.g., C1 esterase inhibitor (C1INH). Thus, in certain embodiments, about 5, 10, 15, 20, 30, 40, 60, 80, 120, 250, 500, 600, 700, 800, 1000 mg of DX-88 can be administered to a subject, e.g., over a twenty-four hour period. In other embodiments, less than 5, 10, 15, 20, 30, 40, 60, 80, 120, 250, 500, 600, 700, 80, 1000 mg of DX-88 can be administered, e.g., over a twenty-four hour period, such that the combination of DX-88 with an anti-thrombolytic agent has a similar (or better) effect on one or more symptom of the disorder than if DX-88 were administered alone.

As the concentration of active kallikrein may have to rise above a certain level to contribute to increased fluid and blood loss post-operatively, in many cases, it is not necessary to inactivate all active kallikrein. DX-88 would be expected to be effective at a significantly lower dose compared to aprotinin on the basis of its higher affinity for kallikrein. Using the same calculations described above, if all prekallikrein is activated, about 15,469 nmoles/L of aprotinin can be used to inhibit kallikrein in a stoichiometric manner. Therefore, an individual having 5 L of plasma would require a dose of 77.5 micromoles aprotinin, or approximately 542 mg.

DX-88 also has greater specificity for kallikrein inhibition compared to aprotinin in vitro. Therefore, proteases other than kallikrein that are inhibited by aprotinin may lower the effective concentration of the inhibitor, thereby increasing the amount of aprotinin needed for a therapeutic effect and leading to unwanted side effects.

Currently there are two regimens approved in the United States for administering aprotinin to a patient undergoing a CABG procedure (see, product label and insert for TRASYLOL™, Bayer Corporation Pharmaceutical Division, West Haven, Conn., the contents of which are incorporated herein).

Several considerations regarding dosing with a polypeptide inhibitor of kallikrein can be illustrated by way of example with the representative DX-88 polypeptide.

Table 1, below, provides a comparison of the affinity (Ki,app) of the DX-88 polypeptide for kallikrein and eleven other known plasma proteases.

TABLE 1

| Protease Substrate | DX-88 $K_i$, app (pM) | Aprotinin $K_i$, app (pM) |
| --- | --- | --- |
| human plasma kallikrein | 44 | $3.0 \times 10^4$ |
| human urine kallikrein | $>1 \times 10^8$ | $4.0 \times 10^3$ |
| porcine pancreatic kallikrein | $2.7 \times 10^7$ | 550 |
| human C1r, activated | $>2.0 \times 10^8$ | $>1.0 \times 10^7$ |
| human C1s, activated | $>2.0 \times 10^7$ | $>1.0 \times 10^8$ |
| human plasma factor XIa | $1.0 \times 10^4$ | ND |
| human plasma factor XIIa | $>2.0 \times 10^7$ | $>1.0 \times 10^8$ |
| human plasmin | $1.4 \times 10^5$ | 894 |
| human pancreatic trypsin | $>2 \times 10^7$ | ND |
| human pancreatic chymotrypsin | $>2.0 \times 10^7$ | $7.3 \times 10^5$ |
| human neutrophil elastase | $>2.0 \times 10^7$ | $1.7 \times 10^6$ |
| human plasma thrombin | $>2.0 \times 10^7$ | $>1.0 \times 10^8$ |

ND = not determined

Clearly, the DX-88 polypeptide is highly specific for human plasma kallikrein. Furthermore, the affinity ($K_i$,app) of DX-88 for kallikrein is 700 times higher than the affinity of aprotinin for kallikrein: the $K_i$,app of DX-88 for kallikrein is about 44 pM (Table 1), whereas the $K_i$,app of aprotinin for kallikrein is 30,000 pM. Thus, a dose of DX-88 could be lower than that used for aprotinin on a per mole basis. Using this information, the dose of each of DX-88 and aprotinin can be determined.

Consideration of several other factors may provide a more accurate estimation of the dose of DX-88 required in practice. Such factors include the amount of kallikrein activated during CPB in a particular patient, the concentration of kallikrein required to elicit an SIR, the bioavailability and pharmacological distribution of DX-88 in a patient and the effect of C1 esterase inhibitor on endogenous plasma kallikrein inhibition. Nevertheless, use of a polypeptide that includes a Kunitz domain that inhibits kallikrein in doses currently approved for the use of aprotinin is still expected to provide significant improvements over the current use of the less specific, lower affinity, bovine aprotinin. Accordingly, lower doses, e.g., at least half, or a tenth of the approved aprotinin dose may be used for a kallikrein inhibitor which inhibits kallikrein at least 2, 5, 10, 20, 30, 50 or 100 fold better than aprotinin.

Another factor to consider is the threshold concentration of kallikrein required to induce a SIR in a patient. If the concentration of active kallikrein must be maintained below, e.g., 1 nM, then owing to its high affinity for kallikrein, DX-88 offers a significant advantage over aprotinin in the amount of protein that would be required to inhibit SIR.

In some embodiment, the kallikrein inhibitor polypeptide is administered in a dose of about 1-500 mg/m$^2$, preferably about 1-250 mg/m$^2$, 1-100 mg/m$^2$. For example, a kallikrein inhibitor polypeptide, e.g., a kallikrein inhibitor polypeptide described herein, can be administered to a subject at risk for cerebral ischemia, suffering from cerebral ischemia, or who has suffered a cerebral ischemic attack at a dose of 1-100 mg/m$^2$. In other embodiments, the dose of the kallikrein inhibitor polypeptide can be less than the doses provided above. For example, the dose of the kallikrein inhibitor can be reduced, such that the combination of the kallikrein inhibitor polypeptide and the anti-thrombolytic agent, give the same or a similar effect as the kallikrein inhibitor polypeptide given at a higher dose.

Suggested dosage regimens for other anti-thrombolytic agents, e.g., anti-fibrinolytic agents, are known. In some embodiments, the suggested dose of the anti-thrombolytic agent, e.g., anti-fibrinolytic agent, can be adjusted such that the combination treatment has, e.g., the same (or better) therapeutic effect than the anti-thrombolytic agent, e.g., anti-fibrinolytic agent given at its suggested dose. Current dosing regimens for epsilon amino caproic acid (Amicar™) are as follows: in adult patients, epsilon amino caproic acid is administered is given at 4 to 5 grams in the first hour and then at 1-1.25 grams/hour, three to four times a day. The current dosing regimen for tranexamic acid (Cyklokapron™) is 10 mg/kg every 6-8 hours for 7 to 10 days.

The kallikrein inhibitor can be administered before, concurrently with, or after the administration of the anti-thrombolytic agent.

The methods described herein can further include administration of another agent or agents other than the kallikrein inhibitor and the anti-thrombolytic agent. For example, an anti-coagulation agent or anti-platelet agent can also be administered to the patient.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, hirudin, bivalirudin, and other direct thrombin inhibitors, and indandione derivatives.

Anti-platelet agents inhibit platelet aggregation and are often used to prevent thromboembolic stroke in patients who have experienced a transient ischemic attack or stroke. Anti-platelet agents include, but are not limited to, aspirin, thienopyridine derivatives such as ticlopidine and clopidogrel, dipyridamole and sulfinpyrazone, as well as RGD mimetics.

The kallikrein inhibitor polypeptides are non-naturally occurring, and can be, e.g., produced synthetically or recombinantly, as noted above, thereby avoiding potential contamination of transmissible diseases that can arise during isolation of a protein from a natural animal source, such as in the case of aprotinin, which is isolated from bovine lung. Increasingly important to administrative and public acceptance of a treatment or pharmaceutical composition comprising a polypeptide is the avoidance of possible contamination with and transmission to human patients of various pathological agents. Of particular interest for the safety of proteins isolated from a bovine tissue is the elimination of the possible risk of exposure to viral mediated diseases, bacterial mediated diseases, and, especially, transmissible bovine spongiform encephalopathies.

As variants of the Kunitz domain 1 of the human LACI protein, fewer side effects are expected from administering the kallikrein inhibitor polypeptides to patients than for aprotinin, which is a bovine protein that is documented to cause anaphylactic and anaphylactoid responses in patients, especially in repeat administrations, such as second time CABG procedures. Additionally, the highly specific binding of the kallikrein inhibitor polypeptides described herein to kallikrein can limit or eliminate the thrombotic tendencies observed with aprotinin, and/or reduce the problems observed with graft patency following CABG procedures.

In some embodiments, the kallikrein inhibitor polypeptide is administered in combination with aprotinin, and one or more side effect associated with aprotinin is reduced or eliminated. One or more side effect of aprotinin that can be reduced or prevented by a combination treatment with a non-naturally occurring kallikrein inhibitor include, but are not limited to: hypersensitivity and pseudo-allergic reactions; itching; rash; sweating; urticaria; skin eruptions; pallor or cyanosis; dyspnoea; nausea; drop in blood pressure; tachycardia or bradycardia; airway obstruction; severe hypotension and anaphylactic shock; renal dysfunction; kidney failure; increase risk of graft closure; increased risk of myocardial infarction.

In other embodiments, the kallikrein inhibitor polypeptide is administered in combination with one or more of epsilon amino caproic acid and/or tranexamic acid and, e.g., one or more side effect associated with administration epsilon amino caproic acid and/or tranexamic acid is reduced or eliminated. One or more side effect of epsilon amino caproic acid and/or tranexamic acid that can be reduced or prevented by a combination treatment with a non-naturally occurring kallikrein inhibitor include, but are not limited to: blood clots; headache; loss of coordination; pains in chest, groin, or legs, especially the calves; shortness of breath; slurred speech; vision changes; weakness or numbness in arm or leg; ringing or buzzing in ears; skin rash; slow or irregular heart beat; stomach cramps; swelling of face, feet or lower legs; unusual tiredness; weight gain; decrease in amount of urine in patient; diarrhea, nausea or vomiting; seizures; and hallucination.

Devices and Kits

Pharmaceutical compositions that include the kallikrein inhibitor and/or the anti-thrombolytic agent (e.g., the anti-fibrinolytic agent) can be administered with a medical device. The device can designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include a non-naturally occurring kallikrein inhibitor and/or an anti-thrombolytic agent, and can be configured to deliver one or more unit doses of the agent or agents.

For example, the pharmaceutical composition can be administered with a device disclosed in U.S. Pat. No. 4,447,233, which discloses a medication infusion pump for delivering medication at a precise infusion rate; and U.S. Pat. No. 4,447,224, which discloses a variable flow implantable infusion apparatus for continuous drug delivery. Many other devices, implants, delivery systems, and modules are also known.

A non-naturally occurring kallikrein inhibitor and/or anti-thrombolytic agent can be provided in a kit. In one embodiment, the kit includes (a) a container that contains a composition that includes a non-naturally occurring kallikrein inhibitor, and optionally (b) informational material. The informational material can be descriptive, instructional, marketing or other material that relates to the methods described herein and/or the use of the agents for therapeutic benefit. In an embodiment, the kit includes also includes an anti-thrombolytic agent. For example, the kit includes a first container that contains a composition that includes the non-naturally occurring kallikrein inhibitor, and a second container that includes the anti-thrombolytic agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the non-naturally occurring kallikrein inhibitor, e.g., in a suitable dose, dosage form, or mode of administration (e.g., a dose, dosage form, or mode of administration described herein), to treat a subject who has or is at risk for blood loss, injury associated with ischemia (e.g., ischemia associated with perioperative blood loss, cerebral ischemia, reperfusion injury, e.g., reperfusion injury associated with cerebral ischemia or a focal brain ischemia), and/or the onset of systemic inflammatory response, e.g., in patients subjected to invasive surgical procedures, especially procedures requiring cardiopulmonary bypass. In one embodiment, the instructions provide a dosing regimen, dosing schedule, and/or route of administration of the kallikrein inhibitor that differs from the dosing regimen, dosing schedule and/or route of administration for the kallikrein inhibitor in the absence of the anti-thrombolytic agent, e.g., a dosing regimen described herein. The information can be provided in a variety of formats, include printed text, computer readable material, video recording, or audio recording, or a information that provides a link or address to substantive material.

In addition to the non-naturally occurring kallikrein inhibitor and/or anti-thrombolytic agent, the composition in the kit can include other ingredients, such as a solvent or buffer, a stabilizer, or a preservative. The non-naturally occurring kallikrein inhibitor and/or anti-thrombolytic agent can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the non-naturally occurring kallikrein inhibitor and the anti-thrombolytic agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

A number of embodiments of the invention have been described. Nevertheless, it will be understood that various modifications may be made without departing from the spirit and scope of the invention. Accordingly, other embodiments are within the scope of the following claims.

What is claimed is:

1. A method for inhibiting or reducing the onset of systemic inflammatory response associated with a surgical procedure in a patient comprising administering to the patient a non-naturally occurring kallikrein inhibitor polypeptide in combination with an anti-thrombolytic agent, wherein the polypeptide comprises the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO: 1),
 wherein Xaa1, Xaa2, Xaa3, Xaa4, Xaa56, Xaa57 or Xaa58 are each individually an amino acid or absent;
 Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 are each any amino acid;
 Xaa10 is Asp;
 Xaa11 is Asp;
 Xaa13 is Pro;
 Xaa15 is Arg;
 Xaa16 is Ala;
 Xaa17 is Ala;
 Xaa18 is His;
 Xaa19 is Pro;
 Xaa21 is Trp;
 Xaa22 is an amino acid selected from the group consisting of: Tyr and Phe;
 Xaa23 is an amino acid selected from the group consisting of: Tyr and Phe;
 Xaa31 is Glu;
 Xaa32 is Glu;
 Xaa34 is Ile;
 Xaa35 is Tyr;
 Xaa39 is Glu;
 Xaa40 is an amino acid selected from the group consisting of: Gly and Ala;
 Xaa43 is an amino acid selected from the group consisting of: Asn and Gly;
 Xaa45 is an amino acid selected from the group consisting of: Phe and Tyr;
 and wherein the polypeptide inhibits kallikrein.

2. The method of claim 1, wherein the surgical procedure is a cardiothoracic surgery.

3. The method of claim 2, wherein the cardiothoracic surgery is cardiopulmonary bypass or coronary artery bypass grafting.

4. The method of claim 1, wherein the polypeptide comprises: Met His Ser Phe Cys Ala Phe Lys Ala Asp Asp Gly Pro Cys Arg Ala Ala His Pro Arg Trp Phe Phe Asn Be Phe Thr Arg Gln Cys Glu Glu Phe Be Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2).

5. The method of claim 4, wherein the polypeptide further comprises a Glu-Ala sequence prior to the Met residue.

6. The method of claim 1, wherein the anti-thrombolytic agent is an antifibrinolytic agent.

7. The method of claim 6, wherein the anti-fibrinolytic agent is selected from the group consisting of: tranexamic acid, epsilon amino caproic acid, aprotinin, desmopressin, pirfenidone, and combinations thereof.

8. A method for inhibiting or reducing cerebral ischemia or reperfusion injury in a patient comprising administering to the patient a non-naturally occurring kallikrein inhibitor polypeptide in combination with an anti-thrombolytic agent, wherein the polypeptide comprises the amino acid sequence: Xaa1 Xaa2 Xaa3 Xaa4 Cys Xaa6 Xaa7 Xaa8 Xaa9 Xaa10 Xaa11 Gly Xaa13 Cys Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Cys Xaa31 Xaa32 Phe Xaa34 Xaa35 Gly Gly Cys Xaa39 Xaa40 Xaa41 Xaa42 Xaa43 Xaa44 Xaa45 Xaa46 Xaa47 Xaa48 Xaa49 Xaa50 Cys Xaa52 Xaa53 Xaa54 Cys Xaa56 Xaa57 Xaa58 (SEQ ID NO: 1), wherein Xaa1, Xaa2, Xaa3, Xaa4, Xaa56, Xaa57 or Xaa58 are each individually an amino acid or absent;
 Xaa6, Xaa7, Xaa8, Xaa9, Xaa20, Xaa24, Xaa25, Xaa26, Xaa27, Xaa28, Xaa29, Xaa41, Xaa42, Xaa44, Xaa46, Xaa47, Xaa48, Xaa49, Xaa50, Xaa52, Xaa53 and Xaa54 are each any amino acid;
 Xaa10 is Asp;
 Xaa11 is Asp;
 Xaa13 is Pro;
 Xaa15 is Arg;
 Xaa16 is Ala;
 Xaa17 is Ala;
 Xaa18 is His;
 Xaa19 is Pro;
 Xaa21 is Trp;
 Xaa22 is an amino acid selected from the group consisting of: Tyr and Phe;
 Xaa23 is an amino acid selected from the group consisting of: Tyr and Phe;
 Xaa31 is Glu;
 Xaa32 is Glu;
 Xaa34 is Ile;
 Xaa35 is Tyr;
 Xaa39 is Glu;
 Xaa40 is an amino acid selected from the group consisting of: Gly and Ala;
 Xaa43 is an amino acid selected from the group consisting of: Asn and Gly;
 Xaa45 is an amino acid selected from the group consisting of: Phe and Tyr;
 and wherein the polypeptide inhibits kallikrein.

9. The method of claim 8, wherein the polypeptide comprises: Met His Ser Phe Cys Ala Phe Lys Ala Asp Asp Gly Pro Cys Arg Ala Ala His Pro Arg Trp Phe Phe Asn Be Phe Thr Arg Gln Cys Glu Glu Phe Be Tyr Gly Gly Cys Glu Gly Asn Gln Asn Arg Phe Glu Ser Leu Glu Glu Cys Lys Lys Met Cys Thr Arg Asp (amino acids 3-60 of SEQ ID NO:2).

10. The method of claim 9, wherein the polypeptide further comprises a Glu-Ala sequence prior to the Met residue.

11. The method of claim 9, wherein the anti-thrombolytic agent is an antifibrinolytic agent.

12. The method of claim 11, wherein the anti-fibrinolytic agent is selected from the group consisting of: tranexamic acid, epsilon amino caproic acid, aprotinin, desmopressin, pirfenidone, and combinations thereof.

* * * * *

```
                         SEQUENCE LISTING

<160> NUMBER OF SEQ ID NOS: 56

<210> SEQ ID NO 1
<211> LENGTH: 58
<212> TYPE: PRT
<213> ORGANISM: Artificial Sequence
<220> FEATURE:
<223> OTHER INFORMATION: Polypeptide Inhibiting Kallikrein
<220> FEATURE:
<221> NAME/KEY: VARIANT
<222> LOCATION: 1, 2, 3, 4, 6, 7, 8, 9, 20, 24, 25, 26, 27, 28, 29, 41,
      42, 44, 46, 47, 48, 49, 50, 52, 53, 54, 56, 57, 58
<223> OTHER INFORMATION: Xaa = any amino acid
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Lys, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
```

```
<222> LOCATION: 22
<223> OTHER INFORMATION: Xaa = Tyr or Phe
<220> FEATURE:
<221> NAME/KEY: VARIANT
<222> LOCATION: 23
<223> OTHER INFORMATION: Xaa = Tyr or Phe
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
      Ile or Thr
<220> FEATURE:
<221> NAME/KEY: VARIANT
<222> LOCATION: 32
<223> OTHER INFORMATION: Xaa = Glu, Gln, Asp, Asn, Pro, Thr, Leu, Ser,
      Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp
<220> FEATURE:
<221> NAME/KEY: VARIANT
<222> LOCATION: 40
<223> OTHER INFORMATION: Xaa = Gly, Ala,
<220> FEATURE:
<221> NAME/KEY: VARIANT
<222> LOCATION: 43
<223> OTHER INFORMATION: Xaa = Asn, Gly
<220> FEATURE:
<221> NAME/KEY: VARIANT
<222> LOCATION: 45
<223> OTHER INFORMATION: Xaa = Phe, Tyr

<400> SEQUENCE: 1

Xaa Xaa Xaa Xaa Cys Xaa Xaa Xaa Xaa Xaa Gly Xaa Cys Xaa Xaa
 1               5                  10                  15

Xaa Xaa Xaa Xaa Xaa Xaa Xaa Xaa Xaa Xaa Xaa Xaa Cys Xaa Xaa
             20                  25                  30

Phe Xaa Xaa Gly Gly Cys Xaa Xaa Xaa Xaa Xaa Xaa Xaa Xaa Xaa
             35                  40                  45

Xaa Xaa Cys Xaa Xaa Xaa Cys Xaa Xaa Xaa
             50                  55

<210> SEQ ID NO 2
<211> LENGTH: 60
<212> TYPE: PRT
<213> ORGANISM: Artificial
<220> FEATURE:
<223> OTHER INFORMATION: Artificial Kunitz Domain

<400> SEQUENCE: 2

Glu Ala Met His Ser Phe Cys Ala Phe Lys Ala Asp Asp Gly Pro Cys
 1               5                  10                  15

Arg Ala Ala His Pro Arg Trp Phe Phe Asn Ile Phe Thr Arg Gln Cys
             20                  25                  30

Glu Glu Phe Ile Tyr Gly Gly Cys Glu Gly Asn Gln Asn Arg Phe Glu
             35                  40                  45

Ser Leu Glu Glu Cys Lys Lys Met Cys Thr Arg Asp
             50                  55                  60

<210> SEQ ID NO 3
```

-continued

```
<211> LENGTH: 180
<212> TYPE: DNA
<213> ORGANISM: Artificial
<220> FEATURE:
<223> OTHER INFORMATION: Artificial Kunitz Domain coding sequence

<400> SEQUENCE: 3
gaggctatgc actctttctg tgctttcaag gctgacgacg gtccgtgcag agctgctcac      60
ccaagatggt tcttcaacat cttcacgcgt caatgcgagg agttcatcta cggtggttgt     120
gagggtaacc aaaacagatt cgagtctcta gaggagtgta agaagatgtg tactagagac    180

<210> SEQ ID NO 4
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 4

Met His Ser Phe Cys Ala Phe Lys Ala Asp Asp Gly Pro Cys Lys Ala
 1               5                  10                  15

Asn His Leu Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 5
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 5

Met His Ser Phe Cys Ala Phe Lys Ala Asp Asp Gly His Cys Lys Ala
 1               5                  10                  15

Asn His Gln Arg Phe Phe Phe Asn Ile Phe Thr Arg Gln Cys Glu Glu
            20                  25                  30

Phe Thr Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 6
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 6

Met His Ser Phe Cys Ala Phe Lys Ala Asp Asp Gly His Cys Lys Ala
 1               5                  10                  15

Asn His Gln Arg Phe Phe Phe Asn Ile Phe Thr Arg Gln Cys Glu Gln
            20                  25                  30

Phe Thr Tyr Gly Gly Cys Ala Gly Asn Gln Asn Arg Phe Glu Ser Leu
        35                  40                  45

Glu Glu Cys Lys Lys Met Cys Thr Arg Asp
    50                  55
```

```
<210> SEQ ID NO 7
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 7

Met His Ser Phe Cys Ala Phe Lys Ala Asp Asp Gly His Cys Lys Ala
  1               5                   10                  15

Ser Leu Pro Arg Phe Phe Asn Ile Phe Thr Arg Gln Cys Glu Glu
             20                  25                  30

Phe Ile Tyr Gly Gly Cys Gly Gly Asn Gln Asn Arg Phe Glu Ser Leu
             35                  40                  45

Glu Glu Cys Lys Lys Met Cys Thr Arg Asp
     50                  55

<210> SEQ ID NO 8
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 8

Met His Ser Phe Cys Ala Phe Lys Ala Asp Asp Gly His Cys Lys Ala
  1               5                   10                  15

Asn His Gln Arg Phe Phe Asn Ile Phe Thr Arg Gln Cys Glu Glu
             20                  25                  30

Phe Ser Tyr Gly Gly Cys Gly Gly Asn Gln Asn Arg Phe Glu Ser Leu
             35                  40                  45

Glu Glu Cys Lys Lys Met Cys Thr Arg Asp
     50                  55

<210> SEQ ID NO 9
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 9

Met His Ser Phe Cys Ala Phe Lys Ala Asp Asp Gly His Cys Lys Gly
  1               5                   10                  15

Ala His Leu Arg Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
             35                  40                  45

Glu Glu Cys Lys Lys Met Cys Thr Arg Asp
     50                  55

<210> SEQ ID NO 10
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 10

Met His Ser Phe Cys Ala Phe Lys Ala Asp Asp Gly Arg Cys Lys Gly
  1               5                   10                  15
```

Ala His Leu Arg Phe Phe Asn Ile Phe Thr Arg Gln Cys Glu Glu
            20                  25                  30

Phe Ile Tyr Gly Gly Cys Glu Gly Asn Gln Asn Arg Phe Glu Ser Leu
        35                  40                  45

Glu Glu Cys Lys Lys Met Cys Thr Arg Asp
    50                  55

<210> SEQ ID NO 11
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 11

Met His Ser Phe Cys Ala Phe Lys Ala Asp Gly Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 12
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 12

Met His Ser Phe Cys Ala Phe Lys Ala Asp Asp Gly Pro Cys Arg Ala
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 13
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 13

Met His Ser Phe Cys Ala Phe Lys Ala Asp Val Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 14
<211> LENGTH: 58

```
<212> TYPE: PRT
<213> ORGANISM: Artificial Sequence
<220> FEATURE:
<223> OTHER INFORMATION: Synthetically generated peptide

<400> SEQUENCE: 14

Met His Ser Phe Cys Ala Phe Lys Ala Asp Val Gly Arg Cys Arg Gly
1               5                   10                  15

Ala Gln Pro Arg Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 15
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 15

Met His Ser Phe Cys Ala Phe Lys Ala Asp Asp Gly Ser Cys Arg Ala
1               5                   10                  15

Ala His Leu Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 16
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 16

Met His Ser Phe Cys Ala Phe Lys Ala Glu Gly Gly Ser Cys Arg Ala
1               5                   10                  15

Ala His Gln Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 17
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 17

Met His Ser Phe Cys Ala Phe Lys Ala Asp Asp Gly Pro Cys Arg Gly
1               5                   10                  15

Ala His Leu Arg Phe Phe Phe Asn Ile Phe Thr Arg Gln Cys Glu Glu
            20                  25                  30
```

```
Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 18
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 18

Met His Ser Phe Cys Ala Phe Lys Ala Asp Asp Gly His Cys Arg Gly
1               5                   10                  15

Ala Leu Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 19
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 19

Met His Ser Phe Cys Ala Phe Lys Ala Asp Ser Gly Asn Cys Arg Gly
1               5                   10                  15

Asn Leu Pro Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 20
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 20

Met His Ser Phe Cys Ala Phe Lys Ala Asp Ser Gly Arg Cys Arg Gly
1               5                   10                  15

Asn His Gln Arg Phe Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 21
<211> LENGTH: 58
<212> TYPE: PRT
<213> ORGANISM: Artificial Sequence
<220> FEATURE:
<223> OTHER INFORMATION: Synthetically generated peptide
```

<400> SEQUENCE: 21

Met His Ser Phe Cys Ala Phe Lys Ala Asp Gly Gly Arg Cys Arg Ala
1               5                   10                  15

Ile Gln Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 22
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 22

Met His Ser Phe Cys Ala Phe Lys Ala Asp Asp Gly Arg Cys Arg Gly
1               5                   10                  15

Ala His Pro Arg Trp Phe Phe Asn Ile Phe Thr Arg Gln Cys Glu Glu
            20                  25                  30

Phe Ser Tyr Gly Gly Cys Gly Gly Asn Gln Asn Arg Phe Glu Ser Leu
        35                  40                  45

Glu Glu Cys Lys Lys Met Cys Thr Arg Asp
    50                  55

<210> SEQ ID NO 23
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 23 ttcgaa                                                                    6

<210> SEQ ID NO 24
<211> LENGTH: 8
<212> TYPE: DNA
<213> ORGANISM: Artificial Sequence
<220> FEATURE:
<223> OTHER INFORMATION: Modified Cloning Site

<400> SEQUENCE: 24 ttcgcgaa                                                                  8

<210> SEQ ID NO 25
<211> LENGTH: 6
<212> TYPE: DNA
<213> ORGANISM: Artificial Sequence
<220> FEATURE:
<223> OTHER INFORMATION: Modified Cloning Site

<400> SEQUENCE: 25 gacgtc                                                                    6

<210> SEQ ID NO 26
<211> LENGTH: 10
<212> TYPE: DNA
<213> ORGANISM: Artificial Sequence
<220> FEATURE:

<223> OTHER INFORMATION: Modified Cloning Site

<400> SEQUENCE: 26
gacgtacgtc                                                                  10

<210> SEQ ID NO 27
<211> LENGTH: 548
<212> TYPE: DNA
<213> ORGANISM: Artificial Sequence
<220> FEATURE:
<223> OTHER INFORMATION: Nucleotide Sequence of Fusion Protein

<400> SEQUENCE: 27 cgactttta cgacaacttg agaagatcaa aaacaacta attattcgaa acgatgagat        60
tcccatctat cttcactgct gttttgttcg ctgcttcctc tgctttggct gctccagtta       120
acaccactac tgaagacgag actgctcaaa ttcctgctga ggctgtcatc ggttactctg       180
acttggaagg tgacttcgac gtcgctgttt tgccattctc taactctact aacaacggtt       240
tgttgttcat caacactacc atcgcttcta tcgctgctaa ggaggaaggt gtttccctcg       300
agaagagaga ggctatgcac tctttctgtg ctttcaaggc tgacgacggt ccgtgcagag       360
ctgctcaccc aagatggttc ttcaacatct tcacgcgtca atgcgaggag ttcatctacg       420
gtggttgtga gggtaaccaa aacagattcg agtctctaga ggagtgtaag aagatgtgta       480
ctagagacta gtaagaattc gccttagaca tgactgttcc tcagttcaag ttgggcactt       540
acgagaag                                                              548

<210> SEQ ID NO 28
<211> LENGTH: 145
<212> TYPE: PRT
<213> ORGANISM: Artificial Sequence
<220> FEATURE:
<223> OTHER INFORMATION: Fusion Protein

<400> SEQUENCE: 28

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Met His Ser Phe Cys Ala Phe Lys Ala
                85                  90                  95

Asp Asp Gly Pro Cys Arg Ala Ala His Pro Arg Trp Phe Phe Asn Ile
            100                 105                 110

Phe Thr Arg Gln Cys Glu Glu Phe Ile Tyr Gly Gly Cys Glu Gly Asn
        115                 120                 125

Gln Asn Arg Phe Glu Ser Leu Glu Glu Cys Lys Lys Met Cys Thr Arg
    130                 135                 140

Asp
145

<210> SEQ ID NO 29
<211> LENGTH: 58

-continued

```
<212> TYPE: PRT
<213> ORGANISM: Bos taurus

<400> SEQUENCE: 29

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
     50                  55

<210> SEQ ID NO 30
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 30

Lys Glu Asp Ser Cys Gln Leu Gly Tyr Ser Ala Gly Pro Cys Met Gly
 1               5                  10                  15

Met Thr Ser Arg Tyr Phe Tyr Asn Gly Thr Ser Met Ala Cys Glu Thr
             20                  25                  30

Phe Gln Tyr Gly Gly Cys Met Gly Asn Gly Asn Asn Phe Val Thr Glu
         35                  40                  45

Lys Glu Cys Leu Gln Thr Cys Arg Thr Val
     50                  55

<210> SEQ ID NO 31
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 31

Thr Val Ala Ala Cys Asn Leu Pro Ile Val Arg Gly Pro Cys Arg Ala
 1               5                  10                  15

Phe Ile Gln Leu Trp Ala Phe Asp Ala Val Lys Gly Lys Cys Val Leu
             20                  25                  30

Phe Pro Tyr Gly Gly Cys Gln Gly Asn Gly Asn Lys Phe Tyr Ser Glu
         35                  40                  45

Lys Glu Cys Arg Glu Tyr Cys Gly Val Pro
     50                  55

<210> SEQ ID NO 32
<211> LENGTH: 58
<212> TYPE: PRT
<213> ORGANISM: Homo sapiens

<400> SEQUENCE: 32

Met His Ser Phe Cys Ala Phe Lys Ala Asp Asp Gly Pro Cys Lys Ala
 1               5                  10                  15

Ile Met Lys Arg Phe Phe Phe Asn Ile Phe Thr Arg Gln Cys Glu Glu
             20                  25                  30

Phe Ile Tyr Gly Gly Cys Glu Gly Asn Gln Asn Arg Phe Glu Ser Leu
         35                  40                  45

Glu Glu Cys Lys Lys Met Cys Thr Arg Asp
```

<210> SEQ ID NO 33
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 33

Lys Pro Asp Phe Cys Phe Leu Glu Glu Asp Pro Gly Ile Cys Arg Gly
 1               5                  10                  15

Tyr Ile Thr Arg Tyr Phe Tyr Asn Asn Gln Thr Lys Gln Cys Glu Arg
             20                  25                  30

Phe Lys Tyr Gly Gly Cys Leu Gly Asn Met Asn Asn Phe Glu Thr Leu
         35                  40                  45

Glu Glu Cys Lys Asn Ile Cys Glu Asp Gly
     50                  55

<210> SEQ ID NO 34
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 34

Gly Pro Ser Trp Cys Leu Thr Pro Ala Asp Arg Gly Leu Cys Arg Ala
 1               5                  10                  15

Asn Glu Asn Arg Phe Tyr Tyr Asn Ser Val Ile Gly Lys Cys Arg Pro
             20                  25                  30

Phe Lys Tyr Ser Gly Cys Gly Gly Asn Glu Asn Asn Phe Thr Ser Lys
         35                  40                  45

Gln Glu Cys Leu Arg Ala Cys Lys Lys Gly
     50                  55

<210> SEQ ID NO 35
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 35

Leu Pro Asn Val Cys Ala Phe Pro Met Glu Lys Gly Pro Cys Gln Thr
 1               5                  10                  15

Tyr Met Thr Arg Trp Phe Phe Asn Phe Glu Thr Gly Glu Cys Glu Leu
             20                  25                  30

Phe Ala Tyr Gly Gly Cys Gly Gly Asn Ser Asn Asn Phe Leu Arg Lys
         35                  40                  45

Glu Lys Cys Glu Lys Phe Cys Lys Phe Thr
     50                  55

<210> SEQ ID NO 36
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 36

Glu Thr Asp Ile Cys Lys Leu Pro Lys Asp Glu Gly Thr Cys Arg Asp

```
                1               5                   10                  15
            Phe Ile Leu Lys Trp Tyr Tyr Asp Pro Asn Thr Lys Ser Cys Ala Arg
                            20                  25                  30

Phe Trp Tyr Gly Gly Cys Gly Gly Asn Glu Asn Lys Phe Gly Ser Gln
                        35                  40                  45

Lys Glu Cys Glu Lys Val Cys Ala Pro Val
                        50                  55
```

<210> SEQ ID NO 37
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 37

```
            Asn Ala Glu Ile Cys Leu Leu Pro Leu Asp Tyr Gly Pro Cys Arg Ala
             1               5                   10                  15

Leu Leu Leu Arg Tyr Tyr Tyr Asp Arg Tyr Thr Gln Ser Cys Arg Gln
                            20                  25                  30

Phe Leu Tyr Gly Gly Cys Glu Gly Asn Ala Asn Asn Phe Tyr Thr Trp
                        35                  40                  45

Glu Ala Cys Asp Asp Ala Cys Trp Arg Ile
                        50                  55
```

<210> SEQ ID NO 38
<211> LENGTH: 61
<212> TYPE: PRT
<213> ORGANISM: Artificial Sequence
<220> FEATURE:
<223> OTHER INFORMATION: Synthetically generated peptide

<400> SEQUENCE: 38

```
            Val Pro Lys Val Cys Arg Leu Gln Val Ser Val Asp Asp Gln Cys Glu
             1               5                   10                  15

Gly Ser Thr Glu Lys Tyr Phe Phe Asn Leu Ser Ser Met Thr Cys Glu
                            20                  25                  30

Lys Phe Phe Ser Gly Gly Cys His Arg Asn Arg Ile Glu Asn Arg Phe
                        35                  40                  45

Pro Asp Glu Ala Thr Cys Met Gly Phe Cys Ala Pro Lys
                        50                  55                  60
```

<210> SEQ ID NO 39
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 39

```
            Ile Pro Ser Phe Cys Tyr Ser Pro Lys Asp Glu Gly Leu Cys Ser Ala
             1               5                   10                  15

Asn Val Thr Arg Tyr Tyr Phe Asn Pro Arg Tyr Arg Thr Cys Asp Ala
                            20                  25                  30

Phe Thr Tyr Thr Gly Cys Gly Gly Asn Asp Asn Asn Phe Val Ser Arg
                        35                  40                  45

Glu Asp Cys Lys Arg Ala Cys Ala Lys Ala
                        50                  55
```

<210> SEQ ID NO 40

```
<211> LENGTH: 59
<212> TYPE: PRT
<213> ORGANISM: Artificial Sequence
<220> FEATURE:
<223> OTHER INFORMATION: Synthetically generated peptide

<400> SEQUENCE: 40

Arg Asn Arg Glu Val Cys Ser Glu Gln Ala Glu Thr Gly Pro Cys Arg
1               5                   10                  15

Ala Met Ile Ser Arg Trp Tyr Phe Asp Val Thr Glu Gly Lys Cys Ala
            20                  25                  30

Pro Phe Phe Tyr Gly Gly Cys Gly Gly Asn Arg Asn Asn Phe Asp Thr
        35                  40                  45

Glu Glu Tyr Cys Met Ala Val Cys Gly Ser Ala
    50                  55

<210> SEQ ID NO 41
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 41

Arg Pro Asp Phe Cys Leu Glu Pro Pro Tyr Thr Gly Pro Cys Val Ala
1               5                   10                  15

Met Phe Pro Arg Tyr Phe Tyr Asn Ala Lys Ala Gly Leu Cys Gln Thr
            20                  25                  30

Phe Val Tyr Gly Gly Cys Met Gly Asn Gly Asn Asn Phe Lys Ser Ala
        35                  40                  45

Glu Asp Cys Met Arg Thr Cys Gly Gly Ala
    50                  55

<210> SEQ ID NO 42
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 42

Arg Pro Asp Phe Cys Gln Leu Gly Tyr Ser Ala Gly Pro Cys Val Ala
1               5                   10                  15

Met Phe Pro Arg Tyr Phe Tyr Asn Gly Thr Ser Met Ala Cys Gln Thr
            20                  25                  30

Phe Val Tyr Gly Gly Cys Met Gly Asn Gly Asn Asn Phe Val Thr Glu
        35                  40                  45

Lys Asp Cys Leu Gln Thr Cys Arg Gly Ala
    50                  55

<210> SEQ ID NO 43
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 43

Arg Pro Asp Phe Cys Gln Leu Gly Tyr Ser Ala Gly Pro Cys Val Ala
1               5                   10                  15

Met Phe Pro Arg Tyr Phe Tyr Asn Gly Ala Ser Met Ala Cys Gln Thr
            20                  25                  30
```

```
Phe Val Tyr Gly Gly Cys Met Gly Asn Gly Asn Asn Phe Val Thr Glu
        35                  40                  45
Lys Asp Cys Leu Gln Thr Cys Arg Gly Ala
    50                  55
```

<210> SEQ ID NO 44
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 44

```
Arg Pro Asp Phe Cys Gln Leu Gly Tyr Ser Ala Gly Pro Cys Val Ala
1               5                   10                  15
Met Phe Pro Arg Tyr Phe Tyr Asn Gly Thr Ser Met Ala Cys Glu Thr
                20                  25                  30
Phe Val Tyr Gly Gly Cys Met Gly Asn Gly Asn Asn Phe Val Thr Glu
        35                  40                  45
Lys Asp Cys Leu Gln Thr Cys Arg Gly Ala
    50                  55
```

<210> SEQ ID NO 45
<211> LENGTH: 58
<212> TYPE: PRT
<213> ORGANISM: Artificial Sequence
<220> FEATURE:
<223> OTHER INFORMATION: Synthetically generated peptide

<400> SEQUENCE: 45

```
Arg Pro Asp Phe Cys Gln Leu Gly Tyr Ser Ala Gly Pro Cys Val Gly
1               5                   10                  15
Met Phe Ser Arg Tyr Phe Tyr Asn Gly Thr Ser Met Ala Cys Gln Thr
                20                  25                  30
Phe Val Tyr Gly Gly Cys Met Gly Asn Gly Asn Asn Phe Val Thr Glu
        35                  40                  45
Lys Asp Cys Leu Gln Thr Cys Arg Gly Ala
    50                  55
```

<210> SEQ ID NO 46
<211> LENGTH: 62
<212> TYPE: PRT
<213> ORGANISM: Artificial Sequence
<220> FEATURE:
<223> OTHER INFORMATION: Synthetically generated peptide

<400> SEQUENCE: 46

```
Glu Ala Glu Ala Arg Pro Asp Phe Cys Leu Glu Pro Pro Tyr Thr Gly
1               5                   10                  15
Pro Cys Ile Ala Phe Phe Pro Arg Tyr Phe Tyr Asn Ala Lys Ala Gly
                20                  25                  30
Leu Cys Gln Thr Phe Val Tyr Gly Gly Cys Met Gly Asn Gly Asn Asn
        35                  40                  45
Phe Lys Ser Ala Glu Asp Cys Met Arg Thr Cys Gly Gly Ala
    50                  55                  60
```

<210> SEQ ID NO 47
<211> LENGTH: 56
<212> TYPE: PRT
<213> ORGANISM: Artificial Sequence
<220> FEATURE:

<223> OTHER INFORMATION: Synthetically generated peptide

<400> SEQUENCE: 47

Ala Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 48
<211> LENGTH: 56
<212> TYPE: PRT
<213> ORGANISM: Artificial Sequence
<220> FEATURE:
<223> OTHER INFORMATION: Synthetically generated peptide

<400> SEQUENCE: 48

Ala Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 49
<211> LENGTH: 56
<212> TYPE: PRT
<213> ORGANISM: Artificial Sequence
<220> FEATURE:
<223> OTHER INFORMATION: Synthetically generated peptide

<400> SEQUENCE: 49

Glu Ala Cys Asn Leu Pro Ile Val Arg Gly Pro Cys Ile Ala Phe Phe
1               5                   10                  15

Pro Arg Trp Ala Phe Asp Ala Val Lys Gly Lys Cys Val Leu Phe Pro
            20                  25                  30

Tyr Gly Gly Cys Gln Gly Asn Gly Asn Lys Phe Tyr Ser Glu Lys Glu
        35                  40                  45

Cys Arg Glu Tyr Cys Gly Val Pro
    50                  55

<210> SEQ ID NO 50
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 50

Glu Ala Val Arg Glu Val Cys Ser Glu Gln Ala Glu Thr Gly Pro Cys
1               5                   10                  15

Ile Ala Phe Phe Pro Arg Trp Tyr Phe Asp Val Thr Glu Gly Lys Cys
            20                  25                  30

Ala Pro Phe Phe Tyr Gly Gly Cys Gly Gly Asn Arg Asn Asn Phe Asp
        35                  40                  45

```
Thr Glu Glu Tyr Cys Met Ala Val Cys Gly Ser Ala
    50                  55                  60

<210> SEQ ID NO 51
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 51

Glu Ala Asn Ala Glu Ile Cys Leu Leu Pro Leu Asp Tyr Gly Pro Cys
1               5                   10                  15

Ile Ala Phe Phe Pro Arg Tyr Tyr Tyr Asp Arg Tyr Thr Gln Ser Cys
            20                  25                  30

Arg Gln Phe Leu Tyr Gly Gly Cys Glu Gly Asn Ala Asn Asn Phe Tyr
        35                  40                  45

Thr Trp Glu Ala Cys Asp Asp Ala Cys Trp Arg Ile
    50                  55                  60

<210> SEQ ID NO 52
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 52

Glu Ala Lys Pro Asp Phe Cys Phe Leu Glu Glu Asp Pro Gly Ile Cys
1               5                   10                  15

Ile Gly Phe Phe Pro Arg Tyr Phe Tyr Asn Asn Gln Ala Lys Gln Cys
            20                  25                  30

Glu Arg Phe Val Tyr Gly Gly Cys Leu Gly Asn Met Asn Asn Phe Glu
        35                  40                  45

Thr Leu Glu Glu Cys Lys Asn Ile Cys Glu Asp Gly
    50                  55                  60

<210> SEQ ID NO 53
<211> LENGTH: 60
<212> TYPE: PRT
<213> ORGANISM: Artificial Sequence
<220> FEATURE:
<223> OTHER INFORMATION: Synthetically generated peptide

<400> SEQUENCE: 53

Glu Ala Glu Thr Asp Ile Cys Lys Leu Pro Lys Asp Glu Gly Thr Cys
1               5                   10                  15

Ile Ala Phe Phe Pro Arg Trp Tyr Tyr Asp Pro Asn Thr Lys Ser Cys
            20                  25                  30

Ala Arg Phe Val Tyr Gly Gly Cys Gly Gly Asn Glu Asn Lys Phe Gly
        35                  40                  45

Ser Gln Lys Glu Cys Glu Lys Val Cys Ala Pro Val
    50                  55                  60

<210> SEQ ID NO 54
<211> LENGTH: 304
<212> TYPE: PRT
<213> ORGANISM: Homo sapiens

<400> SEQUENCE: 54

Met Ile Tyr Thr Met Lys Lys Val His Ala Leu Trp Ala Ser Val Cys
1               5                   10                  15
```

```
Leu Leu Leu Asn Leu Ala Pro Ala Pro Leu Asn Ala Asp Ser Glu Glu
             20                  25                  30

Asp Glu Glu His Thr Ile Ile Thr Asp Thr Glu Leu Pro Leu Lys
         35                  40                  45

Leu Met His Ser Phe Cys Ala Phe Lys Ala Asp Asp Gly Pro Cys Lys
 50                  55                  60

Ala Ile Met Lys Arg Phe Phe Phe Asn Ile Phe Thr Arg Gln Cys Glu
 65                  70                  75                  80

Glu Phe Ile Tyr Gly Gly Cys Glu Gly Asn Gln Asn Arg Phe Glu Ser
                 85                  90                  95

Leu Glu Glu Cys Lys Lys Met Cys Thr Arg Asp Asn Ala Asn Arg Ile
             100                 105                 110

Ile Lys Thr Thr Leu Gln Gln Glu Lys Pro Asp Phe Cys Phe Leu Glu
         115                 120                 125

Glu Asp Pro Gly Ile Cys Arg Gly Tyr Ile Thr Arg Tyr Phe Tyr Asn
 130                 135                 140

Asn Gln Thr Lys Gln Cys Glu Arg Phe Lys Tyr Gly Gly Cys Leu Gly
145                 150                 155                 160

Asn Met Asn Asn Phe Glu Thr Leu Glu Glu Cys Lys Asn Ile Cys Glu
                 165                 170                 175

Asp Gly Pro Asn Gly Phe Gln Val Asp Asn Tyr Gly Thr Gln Leu Asn
             180                 185                 190

Ala Val Asn Asn Ser Leu Thr Pro Gln Ser Thr Lys Val Pro Ser Leu
         195                 200                 205

Phe Glu Phe His Gly Pro Ser Trp Cys Leu Thr Pro Ala Asp Arg Gly
 210                 215                 220

Leu Cys Arg Ala Asn Glu Asn Arg Phe Tyr Tyr Asn Ser Val Ile Gly
225                 230                 235                 240

Lys Cys Arg Pro Phe Lys Tyr Ser Gly Cys Gly Gly Asn Glu Asn Asn
                 245                 250                 255

Phe Thr Ser Lys Gln Glu Cys Leu Arg Ala Cys Lys Lys Gly Phe Ile
             260                 265                 270

Gln Arg Ile Ser Lys Gly Gly Leu Ile Lys Thr Lys Arg Lys Arg Lys
         275                 280                 285

Lys Gln Arg Val Lys Ile Ala Tyr Glu Glu Ile Phe Val Lys Asn Met
 290                 295                 300

<210> SEQ ID NO 55
<211> LENGTH: 58
<212> TYPE: PRT
<213> ORGANISM: Bos taurus

<400> SEQUENCE: 55

Arg Pro Asp Phe Cys Leu Glu Pro Pro Tyr Thr Gly Pro Cys Lys Ala
 1               5                  10                  15

Arg Ile Ile Arg Tyr Phe Tyr Asn Ala Lys Ala Gly Leu Cys Gln Thr
             20                  25                  30

Phe Val Tyr Gly Gly Cys Arg Ala Lys Arg Asn Asn Phe Lys Ser Ala
         35                  40                  45

Glu Asp Cys Met Arg Thr Cys Gly Gly Ala
 50                  55

<210> SEQ ID NO 56
<211> LENGTH: 58
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 10
<223> OTHER INFORMATION: Xaa = Asp or Glu
<220> FEATURE:
<221> NAME/KEY: VARIANT
<222> LOCATION: 11
<223> OTHER INFORMATION: Xaa = Asp, Gly, Ser, Val, Asn, Ile, Ala or Thr
<220> FEATURE:
<221> NAME/KEY: VARIANT
<222> LOCATION: 13
<223> OTHER INFORMATION: Xaa = Arg, His, Pro, Asn, Ser, Thr, Ala, Gly,
      Lys or Gln
<220> FEATURE:
<221> NAME/KEY: VARIANT
<222> LOCATION: 15
<223> OTHER INFORMATION: Xaa = Arg, Ala, Ser, Gly, Met, Asn or Gln
<220> FEATURE:
<221> NAME/KEY: VARIANT
<222> LOCATION: 16
<223> OTHER INFORMATION: Xaa = Ala, Gly, Ser, Asp or Asn
<220> FEATURE:
<221> NAME/KEY: VARIANT
<222> LOCATION: 17
<223> OTHER INFORMATION: Xaa = Ala, Asn, Ser, Ile, Gly, Val, Gln or Thr
<220> FEATURE:
<221> NAME/KEY: VARIANT
<222> LOCATION: 18
<223> OTHER INFORMATION: Xaa = His, Leu, Gln or Ala
<220> FEATURE:
<221> NAME/KEY: VARIANT
<222> LOCATION: 19
<223> OTHER INFORMATION: Xaa = Pro, Gln, Leu, Asn or Ile
<220> FEATURE:
<221> NAME/KEY: VARIANT
<222> LOCATION: 21
<223> OTHER INFORMATION: Xaa = Trp, Phe, Tyr, His or Ile
<220> FEATURE:
<221> NAME/KEY: VARIANT
<222> LOCATION: 31
<223> OTHER INFORMATION: Xaa = Glu, Asp, Gln, Asn, Ser, Ala, Val, Leu,
      Ile or Thr
<220> FEATURE:
<221> NAME/KEY: VARIANT
<222> LOCATION: 32
<223> OTHER INFORMATION: Xaa = Glu, Gln, Asp, Asn, Pro, Thr, Leu, Ser,
      Ala, Gly or Val
<220> FEATURE:
<221> NAME/KEY: VARIANT
<222> LOCATION: 34
<223> OTHER INFORMATION: Xaa = Thr, Ile, Ser, Val, Ala, Asn, Gly or Leu
<220> FEATURE:
<221> NAME/KEY: VARIANT
<222> LOCATION: 35
<223> OTHER INFORMATION: Xaa = Tyr, Trp or Phe
<220> FEATURE:
<221> NAME/KEY: VARIANT
<222> LOCATION: 39
<223> OTHER INFORMATION: Xaa = Glu, Gly, Ala, Ser or Asp

<400> SEQUENCE: 56

Met His Ser Phe Cys Ala Phe Lys Ala Xaa Xaa Gly Xaa Cys Xaa Xaa
  1               5                  10                  15

Xaa Xaa Xaa Arg Xaa Phe Phe Asn Ile Phe Thr Arg Gln Cys Xaa Xaa
             20                  25                  30

Phe Xaa Xaa Gly Gly Cys Xaa Gly Asn Gln Asn Arg Phe Glu Ser Leu
         35                  40                  45

Glu Glu Cys Lys Lys Met Cys Thr Arg Asp
 50                  55
```